(12) United States Patent
Cundy et al.

(10) Patent No.: US 8,952,006 B2
(45) Date of Patent: *Feb. 10, 2015

(54) MORPHOLINOALKYL FUMARATE COMPOUNDS, PHARMACEUTICAL COMPOSITIONS, AND METHODS OF USE

(71) Applicant: XenoPort, Inc., Santa Clara, CA (US)

(72) Inventors: Kenneth C. Cundy, Redwood City, CA (US); Suresh K. Manthati, Sunnyvale, CA (US); David J. Wustrow, Los Gatos, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,864

(22) Filed: Feb. 7, 2013

(65) Prior Publication Data

US 2013/0203753 A1 Aug. 8, 2013

Related U.S. Application Data

(60) Provisional application No. 61/595,835, filed on Feb. 7, 2012.

(51) Int. Cl.
| | | |
|---|---|---|
| *A61K 31/5377* | (2006.01) | |
| *A61K 31/5375* | (2006.01) | |
| *C07D 265/30* | (2006.01) | |
| *C07D 295/145* | (2006.01) | |
| *C07D 413/12* | (2006.01) | |
| *C07D 295/088* | (2006.01) | |

(52) U.S. Cl.
CPC .......... *C07D 295/088* (2013.01); *C07D 265/30* (2013.01)
USPC ..................... 514/231.8; 514/239.2; 544/111; 544/171

(58) Field of Classification Search
USPC ..................... 514/231.8, 239.2; 544/111, 171
See application file for complete search history.

(56) References Cited

U.S. PATENT DOCUMENTS

| | | |
|---|---|---|
| 6,277,882 B1 | 8/2001 | Joshi et al. |
| 6,355,676 B1 | 3/2002 | Joshi et al. |
| 6,359,003 B1 | 3/2002 | Joshi et al. |
| 6,436,992 B1 | 8/2002 | Joshi et al. |
| 6,509,376 B1 | 1/2003 | Joshi et al. |
| 6,858,750 B2 | 2/2005 | Joshi et al. |
| 7,157,423 B2 | 1/2007 | Joshi et al. |
| 7,638,118 B2 * | 12/2009 | Flachsmann et al. ........ 424/76.2 |
| 2006/0205659 A1 | 9/2006 | Joshi et al. |
| 2007/0027076 A1 | 2/2007 | Joshi et al. |
| 2008/0004344 A1 | 1/2008 | Nilsson et al. |
| 2008/0089896 A1 | 4/2008 | Wang et al. |
| 2008/0233185 A1 | 9/2008 | Joshi et al. |
| 2010/0048651 A1 | 2/2010 | Gangakhedkar et al. |

FOREIGN PATENT DOCUMENTS

| | | |
|---|---|---|
| GB | 1404989 A | 9/1975 |
| WO | WO 99/49858 | 10/1999 |
| WO | WO 02/055063 | 7/2002 |
| WO | WO 02/055066 | 7/2002 |
| WO | WO 03/087174 | 10/2003 |
| WO | WO 2005/023241 | 3/2005 |
| WO | WO 2005/027899 | 3/2005 |
| WO | WO 2006/037342 | 4/2006 |
| WO | WO 2006/122652 | 11/2006 |
| WO | WO 2007/042034 | 4/2007 |
| WO | 2010/022177 A2 | 2/2010 |
| WO | 2014/096425 A2 | 6/2014 |

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the internet, URL;http;//www.cnn/com/2003/HEALTH/conditions/09/24/alzheimers.drug.ap/index.html>.*
Atreya et al., NF-kB in inflammatory bowel disease, *J Intern Med* (2008), 263(6): 591-6.
Bardgett et al., NMDA receptor blockade and hippocampal neuronal loss impair fear conditioning and position habit reversal in C57B1/6 mice, *Brain Res Bull* (2003), 60: 131-142.
Barnes, Mediators of chronic obstructive pulmonary disease, *Pharm. Reviews* (2004), 56(4): 515-548.
Bertone, Prevalence of Gastric Ulcers in Elite, Heavy Use Western Performance Horses, *AAEP Proceedings* (2000), 46: 256-259.
Bhagavathula et al., 7-Chloro-5-(4-hydroxyphenyl)-1-methyl-3-(naphthalen-2-ylmethyl)-4,5-dihydro-1*H*-benzo[b][1.4]diazepin-2(3*H*)-one (Bz-423), Suppresses Keratinocyte proliferation and has antipsoriatic activity in the human skin-severe, combined immunodeficient mouse transplant model, *J Pharm. Exp. Ther.* (2008), 324(3): 938-947.
Blandini, et al., Glutamate and Parkinson's Disease, *Mol. Neurobiol.* (1996), 12: 73-94.
Boehncke, Animal Models of T Cell-Mediated Skin Diseases, Chapter 12: The Psoriasis SCID Mouse Model: A Tool for Drug Discovery?, *Ernst Schering Res Found Workshop 50*, Zollner et al., eds. New York: Springer (2005), p. 213-34. Print.

(Continued)

*Primary Examiner* — Rebecca Anderson
(74) *Attorney, Agent, or Firm* — Polsinelli PC

(57) ABSTRACT

Morpholinoalkyl fumarates, pharmaceutical compositions comprising the morpholinoalkyl fumarates, and methods of using morpholinoalkyl fumarates and pharmaceutical compositions for treating neurodegenerative, inflammatory, and autoimmune disorders including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis are disclosed.

29 Claims, 1 Drawing Sheet

(56) References Cited

OTHER PUBLICATIONS

Brewer et al., Fumaric acid esters in the management of severe psoriasis, *Clin. Exp. Dermatol.* (2007), 32: 246-49.
Büyükcoskun, Central Effects of Glucagon-like Peptide-1 on Cold Restraint Stress-induced Gastric Mucosal Lesions, *Turk J. Gastroenterol* (2007), 18(3): 150-156.
Büyükcoskun, Role of Intracerebroventricular Vasopressin in the Development of Stress-Induced Gastric Lesions in Rats, *Physiol. Res.* (1999), 48: 451-455.
Camandola et al., NF-κb as a therapeutic target in neurodegenerative diseases, *Expert Opin. Ther. Targets* (2007), 11(2): 123-132.
Cavarra et al., Effects of Cigarette Smoke in Mice with Different Levels of $\alpha_1$-Proteinase Inhibitor and Sensitivity to Oxidants, *Am J Respir Crit Care Med* (2001), 164: 886-890.
Cockcroft et al., Bronchial reactivity to inhaled histamine: a method and clinical survey, *Clin Allergy* (1977), 7: 235-243.
D'Acquisto et al., Inhibition of Nuclear Factor Kappa B(NF-kB): An Emerging Theme in Anti-Inflammatory Therapies, *Mol. Intervent.* (2002), 2(1): 22-35.
Eugster et al., Superantigen overcomes resistance of IL-6-deficient mice towards MOG-induced EAE by a TNFR1 controlled pathway, *Eur J Immunol* (2001), 31: 2302-2312.
Fits et al., Imiquimod-Induced Psoriasis-Like Skin Inflammation in Mice Is Mediated via the IL-23/IL-17 Axis, *J. Immunol.* (2009), 182: 5836-5845.
Gadad et al., Synthesis, spectral studies and anti-inflammatory activity of glycolamide esters of niflumic acid as potential prodrugs, *Arzneimittelforschung* (2002), 52(11): 817-21.
Gesser et al., Dimethylfumarate specifically inhibits the mitogen and stress-Activated kinases 1 and 2 (MSKI/2): possible role for its antipsoriatic effect, *J Investigative Dermatology* (2007), 127: 2129-2137.
Gurney et al., Motor neuron degeneration in mice that express a human cu, zn superoxide dismutase mutation, *Science* (1994), 264(5166): 1772-1775.
Hoefnagel et al., Long-term safety aspects of systemic therapy with fumaric acid esters in severe psoriasis, *Br J Dermatology* (2003), 149: 363-369.
Hsiao-Ashe, Learning and memory in transgenic mice modeling Alzheimer's disease, *Learn. Mem.* (2001), 8: 301-308.
Jurjus et al., Animal models of inflammatory bowel disease, *J Pharmaocol Toxicol Methods* (2004), 50: 81-92.
Lehmann et al., Fumaric acid esters are potent immunosuppressants: inhibition of acute and chronic rejection in rat kidney transplantation models by methyl hydrogen fumarate, *Arch Dermatol Res* (2002), 294: 399-404.
Lehmann et al., Dimethylfumarate induces immunosuppression via glutathione depletion and subsequent induction of heme oxygenase 1, *J Investigative Dermatology* (2007), 127: 835-845.
Loewe et al., Dimethylfumarate inhibits TNF-induced nuclear entry of NF-kB/p65 in human endothelial cells, *J Immunology* (2002), 168: 4781-4787.
Los et al., Nuevos Estered De Acidos Anilinonicotinicos Y N-Fenilantranilicos Sustituidos, *Il Farmaco—Ed. Sc.* (1980), 36(5): 372-85.
Mandhane, et al., Adenosine A2 receptors modulate haloperidol-induced catalepsy in rats, *Eur. J. Pharmacol* (1997), 328: 135-141.
Martin, Molecular basis of the neurodegenerative disorders, *N Engl J Med* (1999), 340: 1970-80.
Martorana et al., Roflumilast fully prevents emphysema in mice chronically exposed to cigarette smoke, *Am J Respir Crit Care Med* (2005), 172: 848-835.
Miller et al., Experimental Autoimmune Encephalomyelitis in the Mouse, *Current Protocols in Immunology* (2007), Supp. 78: 15.1.1-15.1.18.
Mrowietz et al., Dimethylfumarate for psoriasis: more than a dietary curiosity, *Trends Mol Med* (2005), 111(1): 43-48.
Mrowietz et al., Treatment of severe psoriasis with fumaric acid esters: scientific background and guidelines for therapeutic use, *Br J Dermatology* (1999), 141: 424-429.
Murakami et al., Suppression of dextran sodium sulfate-induced colitis in mice by zerumbone, a subtropical ginger sesquiterpene, and nimesulide: separately and in combination, *Biochemical Pharmacol* (2003), 66: 1253-1261.
Nielsen et al., Glycolamide Esters as biolabile prodrugs of carboxylic acid agents: synthesis, stability, bioconversion, and physiochemical properties, *J Pharm Sci* (1988), 77(4): 285-298.
Rowland et al., Amyotrophic lateral sclerosis, *N Engl J Med* (2001), 344: 1688-1700.
Schilling et al., Fumaric acid esters are effective in chronic experimental autoimmune encephalomyelitis and suppress macrophage infiltration, *Clin Experimental Immunology* (2006), 145: 101-107.
Schimrigk et al., Oral fumaric acid esters for the treatment of active multiple sclerosis: an open-label, baseline-controlled pilot study, *Eur J Neurology* (2006), 13: 604-610.
Tabruyn et al., NF-kB: a new player in angiostatic therapy, *Angiogenesis* (2008), 11: 101-106.
Talath et al., Synthesis, stability studies, anti-inflammatory activity and ulcerogenicity of Morpholinoalkyl ester prodrugs of niflumic acid, *Arzneimittelforschung* (2006), 56(11): 744-52.
Talath et al., Stability studies of some glycolamide ester prodrugs of niflumic acid in aqueous buffers and human plasma by HPLC with UV detection, *Arzneimittelforschung* (2006), 56(9): 631-9.
Tracey et al., Tumor necrosis factor antagonist mechanisms of action: a comprehensive review, *Pharmacology & Therapetuics* (2008), 117: 244-279.
Treumer et al., Dimethylfumarate Is a Potent Inducer of Apoptosis in Human T Cells, *J Invest Dermatol* (2003), 121: 1383-1388.
Van Schoor et al., Effect of inhaled fluticasone on bronchial responsiveness to neurokinin A in asthma, *Eur Respir J* (2002), 19: 997-1002.
Van Schoor et al., The effect of the NK2 tachykinin receptor antagonist SR 48968 (saredutant) on neurokinin A-induced bronchoconstriction in asthmatics, *Eur Respir J* (1998), 12: 17-23.
Vandermeeren et al., Dimethylfumarate is an inhibitor of cytokine-induced E-selectin, VCAM-1, and ICAM-1 expression in human endothelial cells, *Biochm Biophys Res Commun* (1997), 234: 19-23.
Villegas et al., A new flavonoid derivative, dosmalfate, attenuates the development of extra sulphate sodium-induced colitis in mice, *Int'l Immunopharmacol* (2003), 3: 1731-1741.
Virley, Developing therapeutics for the treatment of multiple sclerosis, *NeuroRx* (2005), 2(4): 638-649.
Wakkee et al., Drug evaluation: BG-12 an immunomodulatory Dimethylfumarate, *Current Opinion Investigational Drugs* (2007), 8(11): 955-962.
Whiteley et al., Models of Inflammation: Measuring Gastrointestinal Ulceration in the Rat, *Curr. Protocol. Pharm.* (1998): 10.2.1-10.2.4.
Wingerchuk, Multiple Sclerosis: Current Pathophysiological Concepts, *Lab Invest* (2001), 81: 263-281.
Yazdi et al., Fumaric acid esters, *Clinics Dermatology* (2008), 26: 522-526.
Yamada et al., "Synthesis and Polymerization of Unsaturated Dibasic Acid Derivatives," *Yuki Gosei Kagaku Kyokaishi* (1965), 23(2), 19 pages.

* cited by examiner

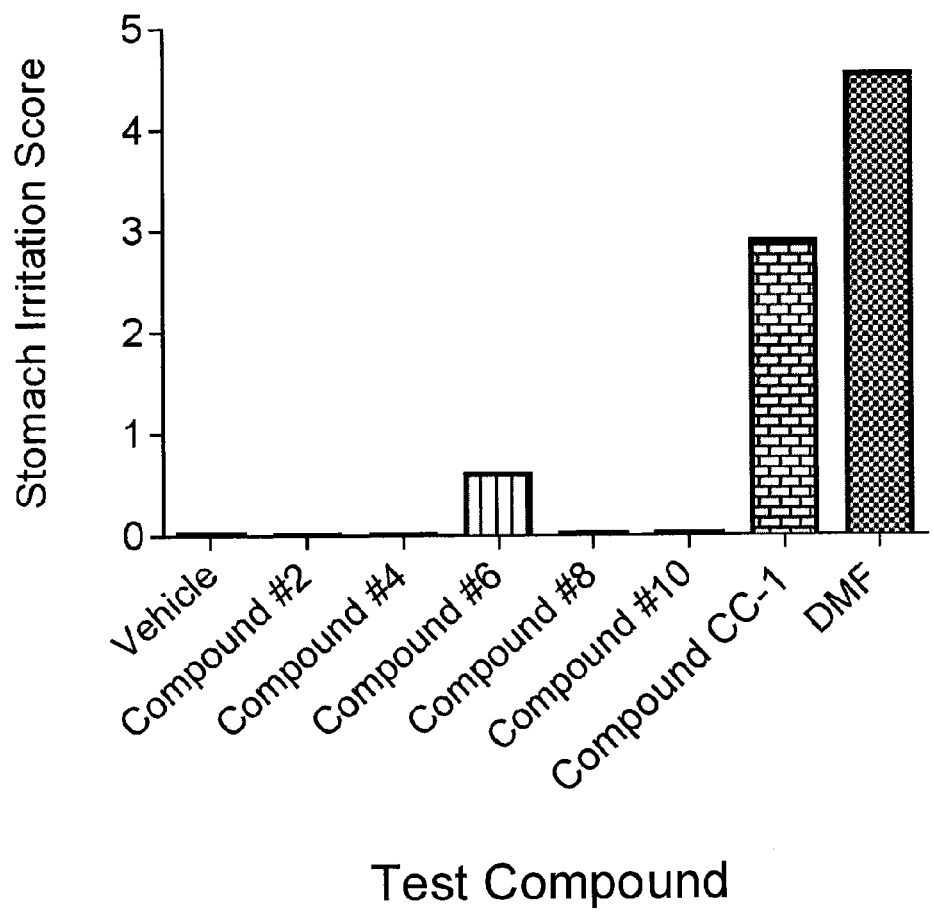

MORPHOLINOALKYL FUMARATE COMPOUNDS, PHARMACEUTICAL COMPOSITIONS, AND METHODS OF USE

CROSS REFERENCE TO RELATED APPLICATIONS

This application claims the benefit of U.S. Provisional Patent Application No. 61/595,835 filed Feb. 7, 2012, which is incorporated herein by reference in its entirety.

FIELD

Disclosed herein are morpholinoalkyl fumarates, pharmaceutical compositions comprising the morpholinoalkyl fumarates, and methods of using said morpholinoalkyl fumarates and pharmaceutical compositions thereof for treating neurodegenerative, inflammatory, and autoimmune diseases including multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

BACKGROUND

Fumaric acid esters (FAEs) are approved in Germany for the treatment of psoriasis, are being evaluated in the United States for the treatment of psoriasis and multiple sclerosis, and have been proposed for use in treating a wide range of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; U.S. Pat. No. 6,277,882; Mrowietz and Asadullah, *Trends Mol Med* 2005, 111(1), 43-48; and Yazdi and Mrowietz, *Clinics Dermatology* 2008, 26, 522-526); asthma and chronic obstructive pulmonary diseases (Joshi et al., WO 2005/023241 and US 2007/0027076); cardiac insufficiency including left ventricular insufficiency, myocardial infarction and angina pectoris (Joshi et al., WO 2005/023241; Joshi et al., US 2007/0027076); mitochondrial and neurodegenerative diseases such as Parkinson's disease, Alzheimer's disease, Huntington's disease, retinopathia pigmentosa and mitochondrial encephalomyopathy (Joshi and Strebel, WO 2002/055063, US 2006/0205659, U.S. Pat. No. 6,509,376, U.S. Pat. No. 6,858,750, and U.S. Pat. No. 7,157,423); transplantation (Joshi and Strebel, WO 2002/055063, US 2006/0205659, U.S. Pat. No. 6,359,003, U.S. Pat. No. 6,509,376, and U.S. Pat. No. 7,157,423; and Lehmann et al., *Arch Dermatol Res* 2002, 294, 399-404); autoimmune diseases (Joshi and Strebel, WO 2002/055063, U.S. Pat. No. 6,509,376, U.S. Pat. No. 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., *Eur J Neurology* 2006, 13, 604-610; and Schilling et al., *Clin Experimental Immunology* 2006, 145, 101-107); ischemia and reperfusion injury (Joshi et al., US 2007/0027076); advanced glycation end products (AGE)-induced genome damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

The mechanism of action of fumaric acid esters is believed to be mediated by pathways associated with the immunological response. For example, FAEs invoke a shift from a Th1 to Th2 immune response, favorably altering the cytokine profile; inhibit cytokine-induced expression of adhesion molecules such as VCAM-1, ICAM-1 and E-selectin, thereby reducing immune cell extravasation; and deplete lymphocytes through apoptotic mechanisms (Lehmann et al., *J Investigative Dermatology* 2007, 127, 835-845; Gesser et al., *J Investigative Dermatology* 2007, 127, 2129-2137; Vandermeeren et al., *Biochm Biophys Res Commun* 1997, 234, 19-23; and Treumer et al., *J Invest Dermatol* 2003, 121, 1383-1388).

Recent studies suggest that FAEs are inhibitors of NF-κB activation, a transcription factor that regulates the inducible expression of proinflammatory mediators (D'Acquisto et al., *Molecular Interventions* 2002, 2(1), 22-35). Accordingly, FAEs have been proposed for use in treating NF-κB mediated diseases (Joshi et al., WO 2002/055066; and Joshi and Strebel, WO 2002/055063, US 2006/0205659, U.S. Pat. No. 7,157,423 and U.S. Pat. No. 6,509,376). Inhibitors of NF-κB activation have also been shown to be useful in angiostatic therapy (Tabruyn and Griffioen, *Angiogenesis* 2008, 11, 101-106), inflammatory bowel disease (Atreya et al., *J Intern Med* 2008, 263(6), 591-6); and in animal models of diseases involving inflammation including neutrophilic alveolitis, asthma, hepatitis, inflammatory bowel disease, neurodegeneration, ischemia/reperfusion, septic shock, glomerulonephritis, and rheumatoid arthritis (D'Acquisto et al., *Molecular Interventions* 2002, 2(1), 22-35).

Studies also suggest that NF-κB inhibition by FAEs may be mediated by interaction with tumor necrosis factor (TNF) signaling. Dimethyl fumarate inhibits TNF-induced tissue factor mRNA and protein expression and TNF-induced DNA binding of NF-κB proteins, and inhibits the TNF-induced nuclear entry of activated NF-κB proteins thereby inhibiting inflammatory gene activation (Loewe et al., *J Immunology* 2002, 168, 4781-4787). TNF signaling pathways are implicated in the pathogenesis of immune-mediated inflammatory diseases such as rheumatoid arthritis, Crohn's disease, psoriasis, psoriatic arthritis, juvenile idiopathic arthritis, and ankylosing spondylitis (Tracey et al., *Pharmacology & Therapetuics* 2008, 117, 244-279).

FUMADERM®, an enteric coated tablet containing a salt mixture of ethyl hydrogen fumarate and dimethyl fumarate (DMF) (2), which is rapidly hydrolyzed to methyl hydrogen fumarate (MHF) (1) in vivo and is regarded as the main bioactive metabolite, was approved in Germany in 1994 for the treatment of psoriasis.

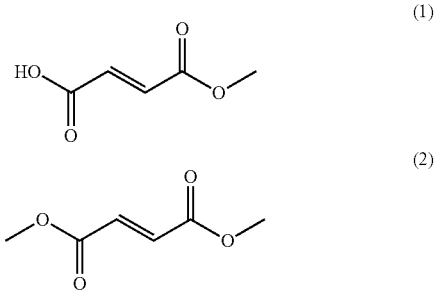

FUMADERM® is dosed three times/day with 1-2 grams/day administered for the treatment of psoriasis. FUMADERM® exhibits a high degree of interpatient variability with respect to drug absorption and food strongly reduces bioavailability. Absorption is thought to occur in the small intestine with peak levels achieved 5-6 hours after oral administration. Significant side effects occur in 70-90% of patients (Brewer and Rogers, *Clin Expt'l Dermatology* 2007, 32, 246-49; and Hoefnagel et al., *Br J Dermatology* 2003, 149, 363-369). Side effects of current FAE therapy include gastrointestinal upset including nausea, vomiting, diarrhea, and transient flushing of the skin. Also, DMF exhibits poor aqueous solubility.

Fumaric acid derivatives (Joshi and Strebel, WO 2002/055063, US 2006/0205659, and U.S. Pat. No. 7,157,423 (amide compounds and protein-fumarate conjugates); Joshi et al., WO 2002/055066 and Joshi and Strebel, U.S. Pat. No. 6,355,676 (mono and dialkyl esters); Joshi and Strebel, WO 2003/087174 (carbocyclic and oxacarbocyclic compounds); Joshi et al., WO 2006/122652 (thiosuccinates); Joshi et al., US 2008/0233185 (dialkyl and diaryl esters)) and salts (Nilsson et al., US 2008/0004344) have been developed in an effort to overcome the deficiencies of current FAE therapy. Controlled release pharmaceutical compositions comprising fumaric acid esters are disclosed by Nilsson and Müller, WO 2007/042034. Glycolamide ester prodrugs are described by Nielsen and Bundgaard, *J Pharm Sci* 1988, 77(4), 285-298.

Flachsmann et al., U.S. Pat. No. 7,638,118, discloses compounds having the following chemical formula:

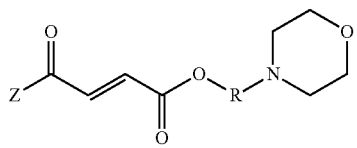

wherein:
$Z$ is $-OR^2$ or $-Y-(R-NR^3R^4)_n$;
$R$ can be a linear or branched $C_{2-9}$ alkyl;
$R^2$ can be a linear or branched $C_{1-8}$ alkyl;
$R^3$ and $R^4$, together with the nitrogen atom to which they are bonded, can form an aromatic heterocyclic ring such as a morpholinyl ring; and
when n is 1, Y can be oxygen.

The compounds are disclosed to be useful for neutralizing odors.

Morpholinoalkyl ester prodrugs of the non-steroidal anti-inflammatory drug niflumic acid exhibit unexpectedly high protection from gastric irritation and ulcerogenicity compared to the parent acid drug (Talath and Gadad, *Arzneimittelforschung* 2006, 56(11), 744-52). The protective effect is believed to involve absorption of the intact prodrug, which reduces local gastric exposure. Although glycolamide esters of niflumic acid have been synthesized in an effort to improve the biocompatibility of niflumic aid, the effects on gastrointestinal irritation in humans does not appear to have been reported (Talath et al, *Arzneimittelforschung* 2006, 56(9), 631-9; Gadad et al., *Arzneimittelforschung* 2002, 52(11), 817-21; Benoit et al., *Rev. Odontostomatol Midi Fr.* 1975, 4, 249-61; and Los et al., *Farmaco Sci.* 1981 36(5), 372-85). However, the morpholinoalkyl esters, and specifically the morpholinopropyl and morpholinobutyl esters of niflumic acid were identified as exhibiting the best combination of stability, in vivo anti-inflammatory activity, and low ulcerogenicity in rats (Talath and Gadad, *Arzneimittelforschung* 2006, 56(11), 744-52).

Gangakhedkar et al., U.S. Patent Publication No. 2010/0048651, discloses compounds having the following chemical formula:

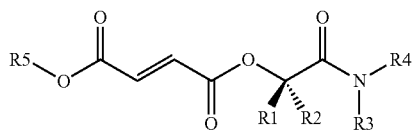

wherein:
$R^1$ and $R^2$ are independently chosen from hydrogen, $C_{1-6}$ alkyl, and substituted $C_{1-6}$ alkyl;
$R^3$ and $R^4$, together with the nitrogen to which they are bonded, can form a $C_{5-10}$ heteroaryl ring such as a morpholino ring; and
$R^5$ can be hydrogen, methyl, ethyl, and $C_{3-6}$ alkyl;

and pharmaceutical compositions containing such compounds for the treatment of diseases including psoriasis, multiple sclerosis, an inflammatory bowel disease, asthma, chronic obstructive pulmonary disease, Parkinson's disease, Huntington's disease, amyotrophic lateral sclerosis (ALS), and arthritis. Compounds in which $-NR^3R^4$ is a morpholino ring are disclosed in Example 3 (methyl 2-morpholin-4-yl-2-oxoethyl(2E)but-2-ene-1,4-dioate), Example 28 (methyl 1-methyl-2-morpholin-4-yl-2-oxoethyl(2E)but-2-ene-1,4-dioate), Example 31 ((1S)-1-methyl-2-morpholin-4-yl-2-oxoethyl methyl(2E)but-2-ene-1,4-dioate), and Example 47 ((2E)-3-[(2-morpholin-4-yl-2-oxoethyl)oxycarbonyl]prop-2-enoic acid).

SUMMARY

Morpholinoalkyl fumarates having high gastrointestinal permeability and/or absorption, improved solubility, ordered hydrolysis (i.e., preferential cleavage of promoieties), and minimal cleavage in the gut lumen or enterocyte cytoplasm are desirable. Such morpholinoalkyl fumarates, which provide higher oral bioavailability and plasma levels of the parent compound, an alkyl hydrogen fumarate, e.g., MHF, and/or other metabolites of the morpholinoalkyl fumarates, may: enhance the efficacy/responder rate compared to present fumaric acid esters; facilitate the use of lower doses, reduce dosing frequency, and standardize dosing regimens; reduce food effects; reduce gastrointestinal side effects/toxicity; and reduce interpatient treatment variability.

Morpholinoalkyl esters of alkyl hydrogen fumarates and hydrogen fumarates having reduced gastrointestinal side effects are disclosed.

In a first aspect, pharmaceutical compositions comprising a pharmaceutically acceptable vehicle and a therapeutically effective amount of a compound of Formula (I):

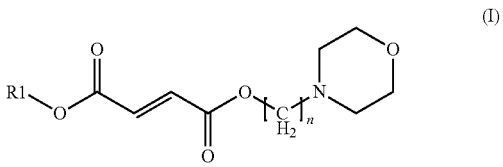

or a pharmaceutically acceptable salt thereof, are provided, wherein:
n is an integer from 2 to 6;
$R^1$ is chosen from methyl, ethyl, $C_{3-6}$ alkyl, and

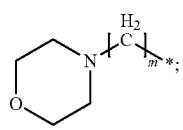

and
m is an integer from 2 to 6.

Such pharmaceutical compositions are useful for treating neurodegenerative, inflammatory and autoimmune diseases and disorders including, for example, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

In a second aspect, methods of treating a disease in a patient are provided comprising administering to a patient in need of such treatment a pharmaceutical composition comprising a therapeutically effective amount of a compound of Formula (I). In certain embodiments, the disease is chosen from a neurodegenerative disease, an inflammatory disease, and an autoimmune disease including, for example, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

In a third aspect, pharmaceutical compositions comprising a pharmaceutically acceptable vehicle and a therapeutically effective amount of a compound of Formula (II):

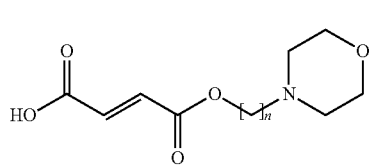

or a pharmaceutically acceptable salt thereof, are provided, wherein n is an integer from 2 to 6.

In a fourth aspect, methods of treating a disease in a patient are provided comprising administering to a patient in need of such treatment a pharmaceutical composition comprising a therapeutically effective amount of a compound of Formula (II). In certain embodiments, the disease is chosen from a neurodegenerative disease, an inflammatory disease, and an autoimmune disease including, for example, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

In a specific aspect, provided here are compounds according to Formula (I):

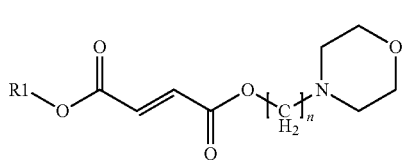

or a pharmaceutically acceptable salt thereof;

wherein:
n is an integer from 2 to 6;
$R^1$ is selected from H, methyl, ethyl, $C_{3-6}$ alkyl, and

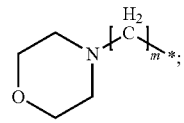

and
m is an integer from 2 to 6;
provided that
i) when n is 2, and $R^1$ is

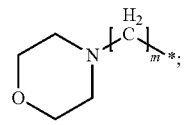

then m is 3, 4, 5, or 6; and
ii) when $R^1$ is H, then n is 4, 5, or 6.

Such compounds are useful for treating neurodegenerative, inflammatory and autoimmune diseases and disorders including, for example, multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

In a particular embodiment, with respect to the pharmaceutical compositions and compounds according to Formula (I), the compound is according to Formula (IIc):

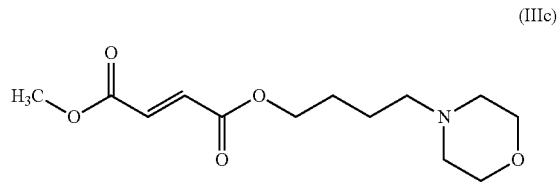 [SMILES: COC(=O)/C=C/C(=O)OCCCCN1CCOCC1]

or a pharmaceutically acceptable salt thereof.

In a more particular embodiment, with respect to the pharmaceutical compositions and compounds according to Formula (I), the compound is a HCl salt of a compound according to Formula (IIIc).

DETAILED DESCRIPTION

Figures

FIG. 1: GI Effect of the Compounds of the Disclosure—FIG. 1 depicts the GI irritation score of exemplary compounds along with comparative compounds (CC-1 and DMF) at an oral dose of 180 mg eq/kg, dosed per day for 4 days in rats.

DEFINITIONS

A dash ("—") that is not between two letters or symbols is used to indicate a point of attachment for a moiety or substituent. For example, —$CONH_2$ is bonded through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include, for example, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like.

The term "alkyl" includes groups having any degree or level of saturation, i.e., groups having exclusively single carbon-carbon bonds, groups having one or more double carbon-carbon bonds, groups having one or more triple carbon-carbon bonds, and groups having combinations of single, double, and triple carbon-carbon bonds. Where a specific level of saturation is intended, the terms alkanyl, alkenyl, or alkynyl are used. In certain embodiments, an alkyl group can have from 1 to 10 carbon atoms ($C_{1-10}$, in certain embodiments, from 1 to 6 carbon atoms ($C_{1-6}$), in certain embodiments from 1 to 4 carbon atoms ($C_{1-4}$), in certain embodiments, from 1 to 3 carbon atoms ($C_{1-3}$), and in certain embodiments, from 1 to 2 carbon atoms ($C_{1-2}$). In certain embodiments, alkyl is methyl, in certain embodiments, ethyl, and in certain embodiments, n-propyl or isopropyl.

"Compounds" of Formula (I) and Formula (II) disclosed herein include any specific compounds within this formula. Compounds may be identified either by their chemical structure and/or chemical name. Compounds are named using Chemistry 4-D Draw Pro, version 7.01c (ChemInnovation Software, Inc., San Diego, Calif.). When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to those skilled in the art. Compounds of Formula (I) and Formula (II) include, for example, optical isomers of compounds of Formula (I) and Formula (II), racemates thereof, and other mixtures thereof. In such embodiments, a single enantiomer or diastereomer, i.e., optically active form can be obtained by asymmetric synthesis or by resolution of the racemates. Resolution of the racemates may be accomplished, for example, by methods such as crystallization in the presence of a resolving agent, or chromatography using, for example, chiral stationary phases. Notwithstanding the foregoing, in compounds of Formula (I) and Formula (II) the configuration of the illustrated double bond is only in the E configuration (i.e., trans configuration).

Compounds of Formula (I) and Formula (II) also include isotopically labeled compounds where one or more atoms have an atomic mass different from the atomic mass conventionally found in nature. Examples of isotopes that may be incorporated into the compounds disclosed herein include, for example, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds disclosed herein may be free acid, hydrated, solvated, or N-oxides. Certain compounds may exist in multiple crystalline, co-crystalline, or amorphous forms. Compounds of Formula (I) and Formula (II) include pharmaceutically acceptable salts thereof or pharmaceutically acceptable solvates of the free acid form of any of the foregoing, as well as crystalline forms of any of the foregoing.

Compounds of Formula (I) and Formula (II) also include solvates. A solvate refers to a molecular complex of a compound with one or more solvent molecules in a stoichiometric or non-stoichiometric amount. Such solvent molecules include those commonly used in the pharmaceutical art, which are known to be innocuous to a patient, e.g., water, ethanol, and the like. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules are water.

Further, when partial structures of the compounds are illustrated, an asterisk (*) indicates the point of attachment of the partial structure to the rest of the molecule.

"Disease" refers to a disease, disorder, condition, or symptom of any of the foregoing.

"Drug" as defined under 21 U.S.C. §321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . ."

"Leaving group" has the meaning conventionally associated with it in synthetic organic chemistry, i.e., an atom or a group capable of being displaced by a nucleophile and includes halogen such as chloro, bromo, fluoro, and iodo; acyloxy, such as acetoxy and benzoyloxy, alkoxycarbonylaryloxycarbonyl, mesyloxy, tosyloxy, and trifluoromethanesulfonyloxy; aryloxy such as 2,4-dinitrophenoxy, methoxy, N,O-dimethylhydroxylamino, p-nitrophenolate, imidazolyl, and the like.

"MHF" refers to methyl hydrogen fumarate, a compound having the following chemical structure:

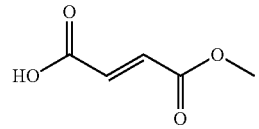

This compound is also sometimes referred to as monomethyl fumarate.

"Parent heteroaromatic ring system" refers to an aromatic ring system in which one or more carbon atoms (and any associated hydrogen atoms) are independently replaced with the same or different heteroatom in such a way as to maintain the continuous π-electron system characteristic of aromatic systems and a number of out-of-plane π-electrons corresponding to the Hückel rule (4n+2). Examples of heteroatoms to replace the carbon atoms include, for example, N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include, for example, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, oxazolidine, and the like.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound that possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient, which does not destroy the pharmacological activity thereof and which is non-toxic when administered in doses sufficient to provide a therapeutically effective amount of the compound or a pharmacologically active metabolite thereof.

"Pharmaceutical composition" refers to a compound of Formula (I), or a pharmaceutically acceptable salt thereof, or a compound of Formula (II), or a pharmaceutically acceptable salt thereof, and at least one pharmaceutically acceptable vehicle, with which the compound of Formula (I), or a pharmaceutically acceptable salt thereof, or the compound of Formula (II), or a pharmaceutically acceptable salt thereof, is administered to a patient.

"Treating" or "treatment" of any disease refers to reversing, alleviating, arresting, or ameliorating a disease or at least one of the clinical symptoms of a disease, reducing the risk of acquiring a disease or at least one of the clinical symptoms of a disease, inhibiting the progress of a disease or at least one of the clinical symptoms of the disease or reducing the risk of developing a disease or at least one of the clinical symptoms of a disease. "Treating" or "treatment" also refers to inhibiting a disease, either physically, (e.g., stabilization of a discernible symptom), physiologically, (e.g., stabilization of a physical parameter), or both, and to inhibiting at least one physical parameter that may or may not be discernible to the patient. In certain embodiments, "treating" or "treatment" refers to delaying the onset of a disease or at least one or more symptoms thereof in a patient who may be exposed to or predisposed to a disease even though that patient does not yet experience or display symptoms of the disease.

"Therapeutically effective amount" refers to the amount of a compound that, when administered to a subject for treating a disease, or at least one of the clinical symptoms of a disease, is sufficient to effect such treatment of the disease or symptom thereof. The "therapeutically effective amount" may vary depending, for example, on the compound, the disease and/or symptoms of the disease, severity of the disease and/or symptoms of the disease, the age, weight, and/or health of the patient to be treated, and the judgment of the prescribing physician. An appropriate amount in any given compound may be ascertained by those skilled in the art and/or is capable of determination by routine experimentation.

"Therapeutically effective dose" refers to a dose that provides effective treatment of a disease in a patient. A therapeutically effective dose may vary from compound to compound and/or from patient to patient, and may depend upon factors such as the condition of the patient and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Compounds

Certain embodiments provide a compound of Formula (I):

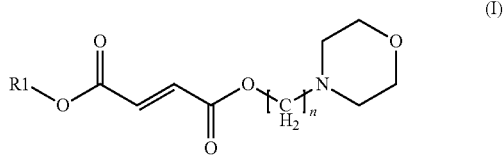

or a pharmaceutically acceptable salt thereof, wherein:
n is an integer from 2 to 6;
R¹ is chosen from methyl, ethyl, $C_{3-6}$ alkyl, and

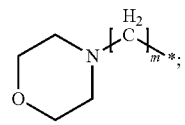

and
m is an integer from 2 to 6.

Certain embodiments provide a compound of Formula (I):

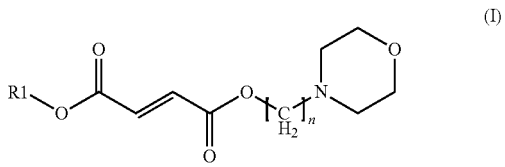

or a pharmaceutically acceptable salt thereof, wherein:
n is an integer from 2 to 6; and
R¹ is chosen from methyl, ethyl, and $C_{3-6}$ alkyl.

Certain embodiments provide a pharmaceutical composition comprising a pharmaceutically acceptable vehicle and a therapeutically effective amount of a compound of Formula (I):

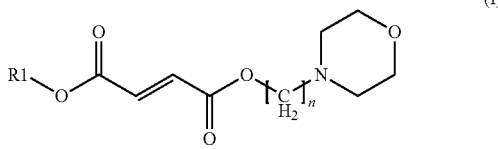

or a pharmaceutically acceptable salt thereof, wherein:
n is an integer from 2 to 6;
R¹ is chosen from methyl, ethyl, $C_{3-6}$ alkyl, and

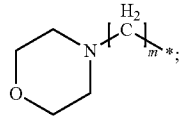

and
m is an integer from 2 to 6.

Certain embodiments provide a pharmaceutical composition comprising a pharmaceutically acceptable vehicle and a therapeutically effective amount of a compound of Formula (I):

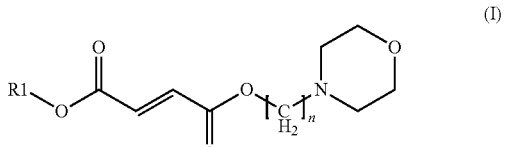

or a pharmaceutically acceptable salt thereof, wherein:
n is an integer from 2 to 6; and
R¹ is chosen from methyl, ethyl, and $C_{3-6}$ alkyl.

In certain embodiments of a compound of Formula (I), n is 2, n is 3, n is 4, n is 5, and in certain embodiments, n is 6.

In certain embodiments of a compound of Formula (I), m is 2, m is 3, m is 4, m is 5, and in certain embodiments, m is 6.

In certain embodiments of a compound of Formula (I), n is 2 and m is 2; n is 2 and m is 3; n is 2 and m is 4; n is 2 and m is 5; and in certain embodiments, n is 2 and m is 6.

In certain embodiments of a compound of Formula (I), n is 3 and m is 2; n is 3 and m is 3; n is 3 and m is 4; n is 3 and m is 5; and in certain embodiments, n is 3 and m is 6.

In certain embodiments of a compound of Formula (I), n is 4 and m is 2; n is 4 and m is 3; n is 4 and m is 4; n is 4 and m is 5; and in certain embodiments, n is 4 and m is 6.

In certain embodiments of a compound of Formula (I), n is 5 and m is 2; n is 5 and m is 3; n is 5 and m is 4; n is 5 and m is 5; and in certain embodiments, n is 5 and m is 6.

In certain embodiments of a compound of Formula (I), n is 6 and m is 2; n is 6 and m is 3; n is 6 and m is 4; n is 6 and m is 5; and in certain embodiments, n is 6 and m is 6.

In certain embodiments of a compound of Formula (I), R¹ is chosen from methyl and ethyl.

In certain embodiments of a compound of Formula (I), R¹ is methyl.

In certain embodiments of a compound of Formula (I), R¹ is ethyl.

In certain embodiments of a compound of Formula (I), R¹ is n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentuyl, 4-methylpentyl, 3-methylpentan-2-yl, 4-methylpentan-2-yl, 2,3-dimethylbutyl, and in certain embodiments, 3,3-dimethylbutyl.

In certain embodiments of a compound of Formula (I), R¹ is

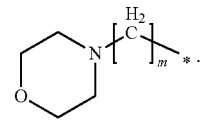

In certain embodiments of a compound of Formula (I), R¹ is

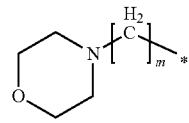

and m is chosen from 2 and 3.

In certain embodiments of a compound of Formula (I), R¹ is

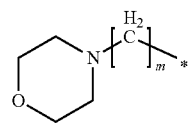

and m is chosen from 4, 5, and 6.

In certain embodiments of a compound of Formula (I), the compound is a pharmaceutically acceptable salt.

In certain embodiments of a compound of Formula (I), the compound is the hydrochloride salt.

In certain embodiments, a compound of Formula (I) has the structure of Formula (Ia):

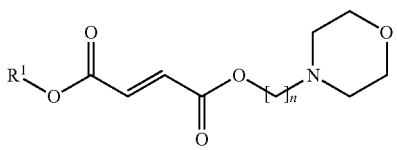

(Ia)

or a pharmaceutically acceptable salt thereof, wherein n is an integer from 2 to 6; and $R^1$ is $C_{1-6}$ alkyl.

In certain embodiments of a compound of Formula (Ia), n is 2. In certain embodiments of a compound of Formula (Ia) where n is 2, the compound is chosen from:
methyl (2-morpholinoethyl)fumarate;
ethyl(morpholinoethyl)fumarate;
(morpholinoethyl)propyl fumarate;
isopropyl (2-morpholinoethyl)fumarate;
butyl (2-morpholinoethyl)fumarate;
sec-butyl (2-morpholinoethyl)fumarate;
isobutyl (2-morpholinoethyl)fumarate;
tert-butyl (2-morpholinoethyl)fumarate;
(2-morpholinoethyl)pentyl fumarate;
(2-morpholinoethyl)pentyl-2-yl fumarate;
2-methylbutyl (2-morpholinoethyl)fumarate;
isopentyl (2-morpholinoethyl)fumarate;
3-methylbutan-2-yl (2-morpholinoethyl)fumarate;
2-morpholinoethyl neopentyl fumarate;
2-morpholinoethyl tert-pentyl fumarate;
hexyl (2-morpholinoethyl)fumarate;
hexan-2-yl (2-morpholinoethyl)fumarate;
2-methylpentyl (2-morpholinoethyl)fumarate;
3-methylpentyl (2-morpholinoethyl)fumarate;
4-methylpentyl (2-morpholinoethyl)fumarate;
3-methylpentan-2-yl (2-morpholinoethyl)fumarate;
4-methylpentan-2-yl (2-morpholinoethyl)fumarate;
2,3-dimethylbutyl (2-morpholinoethyl)fumarate; and
3,3-dimethylbutyl (2-morpholinoethyl)fumarate;
or a pharmaceutically acceptable salt of any of the foregoing.

In certain embodiments of a compound of Formula (Ia), n is 3. In certain embodiments of a compound of Formula (Ia) where n is 3, the compound is chosen from:
methyl (3-morpholinopropyl)fumarate;
ethyl (3-morpholinopropyl)fumarate;
(3-morpholinopropyl)propyl fumarate;
isopropyl (3-morpholinopropyl)fumarate;
butyl (3-morpholinopropyl)fumarate;
sec-butyl (3-morpholinopropyl)fumarate;
isobutyl (3-morpholinopropyl)fumarate;
tert-butyl (3-morpholinopropyl)fumarate;
(3-morpholinopropyl)pentyl fumarate;
(3-morpholinopropyl)pentyl-2-yl fumarate;
2-methylbutyl (3-morpholinopropyl)fumarate;
isopentyl (3-morpholinopropyl)fumarate;
3-methylbutan-2-yl (3-morpholinopropyl)fumarate;
3-morpholinopropyl neopentyl fumarate;
3-morpholinopropyl tert-pentyl fumarate;
hexyl (3-morpholinopropyl)fumarate;
hexan-2-yl (3-morpholinopropyl)fumarate;
2-methylpentyl (3-morpholinopropyl)fumarate;
3-methylpentyl (3-morpholinopropyl)fumarate;
4-methylpentyl (3-morpholinopropyl)fumarate;
3-methylpentan-2-yl (3-morpholinopropyl)fumarate;
4-methylpentan-2-yl (3-morpholinopropyl)fumarate;
2,3-dimethylbutyl (3-morpholinopropyl)fumarate; and
3,3-dimethylbutyl (3-morpholinopropyl)fumarate;
or a pharmaceutically acceptable salt of any of the foregoing.

In certain embodiments of a compound of Formula (Ia), n is 4. In certain embodiments of a compound of Formula (Ia) where n is 4, the compound is chosen from:
methyl (4-morpholinobutyl)fumarate;
ethyl (4-morpholinobutyl)fumarate;
(4-morpholinobutyl)propyl fumarate;
isopropyl (4-morpholinobutyl)fumarate;
butyl (4-morpholinobutyl)fumarate;
sec-butyl (4-morpholinobutyl)fumarate;
isobutyl (4-morpholinobutyl)fumarate;
tert-butyl (4-morpholinobutyl)fumarate;
(4-morpholinobutyl)pentyl fumarate;
(4-morpholinobutyl)pentyl-2-yl fumarate;
2-methylbutyl (4-morpholinobutyl)fumarate;
isopentyl (4-morpholinobutyl)fumarate;
3-methylbutan-2-yl (4-morpholinobutyl)fumarate;
4-morpholinobutyl neopentyl fumarate;
4-morpholinobutyl tert-pentyl fumarate;
hexyl (4-morpholinobutyl)fumarate;
hexan-2-yl (4-morpholinobutyl)fumarate;
2-methylpentyl (4-morpholinobutyl)fumarate;
3-methylpentyl (4-morpholinobutyl)fumarate;
4-methylpentyl (4-morpholinobutyl)fumarate;
3-methylpentan-2-yl (4-morpholinobutyl)fumarate;
4-methylpentan-2-yl (4-morpholinobutyl)fumarate;
2,3-dimethylbutyl (4-morpholinobutyl)fumarate; and
3,3-dimethylbutyl (4-morpholinobutyl)fumarate;
or a pharmaceutically acceptable salt of any of the foregoing.

In certain embodiments of a compound of Formula (Ia), n is 5. In certain embodiments of a compound of Formula (Ia) where n is 5, the compound is chosen from:
methyl (5-morpholinopentyl)fumarate;
ethyl (5-morpholinopentyl)fumarate;
(5-morpholinopentyl)propyl fumarate;
isopropyl (5-morpholinopentyl)fumarate;
butyl (5-morpholinopentyl)fumarate;
sec-butyl (5-morpholinopentyl)fumarate;
isobutyl (5-morpholinopentyl)fumarate;
tert-butyl (5-morpholinopentyl)fumarate;
(5-morpholinopentyl)pentyl fumarate;
(5-morpholinopentyl)pentyl-2-yl fumarate;
2-methylbutyl (5-morpholinopentyl)fumarate;
isopentyl (5-morpholinopentyl)fumarate;
3-methylbutan-2-yl (5-morpholinopentyl)fumarate;
5-morpholinopentyl neopentyl fumarate;
5-morpholinopentyl tert-pentyl fumarate;
hexyl (5-morpholinopentyl)fumarate;
hexan-2-yl (5-morpholinopentyl)fumarate;
2-methylpentyl (5-morpholinopentyl)fumarate;
3-methylpentyl (5-morpholinopentyl)fumarate;
4-methylpentyl (5-morpholinopentyl)fumarate;
3-methylpentan-2-yl (5-morpholinopentyl)fumarate;
4-methylpentan-2-yl (5-morpholinopentyl)fumarate;
2,3-dimethylbutyl (5-morpholinopentyl)fumarate; and
3,3-dimethylbutyl (5-morpholinopentyl)fumarate;
or a pharmaceutically acceptable salt of any of the foregoing.

In certain embodiments of a compound of Formula (Ia), n is 6. In certain embodiments of a compound of Formula (Ia) where n is 6, the compound is chosen from:
methyl (6-morpholinohexyl)fumarate;
ethyl (6-morpholinohexyl)fumarate;
(6-morpholinohexyl)propyl fumarate;
isopropyl (6-morpholinohexyl)fumarate;
butyl (6-morpholinohexyl)fumarate;
sec-butyl (6-morpholinohexyl)fumarate;
isobutyl (6-morpholinohexyl)fumarate;
tert-butyl (6-morpholinohexyl)fumarate;

(6-morpholinohexyl)pentyl fumarate;
(6-morpholinohexyl)pentyl-2-yl fumarate;
2-methylbutyl (6-morpholinohexyl)fumarate;
isopentyl (6-morpholinohexyl)fumarate;
3-methylbutan-2-yl (6-morpholinohexyl)fumarate;
6-morpholinohexyl neopentyl fumarate;
6-morpholinohexyl tert-pentyl fumarate;
hexyl (6-morpholinohexyl)fumarate;
hexan-2-yl (6-morpholinohexyl)fumarate;
2-methylpentyl (6-morpholinohexyl)fumarate;
3-methylpentyl (6-morpholinohexyl)fumarate;
4-methylpentyl (6-morpholinohexyl)fumarate;
3-methylpentan-2-yl (6-morpholinohexyl)fumarate;
4-methylpentan-2-yl (6-morpholinohexyl)fumarate;
2,3-dimethylbutyl (6-morpholinohexyl)fumarate; and
3,3-dimethylbutyl (6-morpholinohexyl)fumarate;
or a pharmaceutically acceptable salt of any of the foregoing.

In certain embodiments of compounds of Formula (Ia), the compound is chosen from:
methyl(morpholinoethyl)fumarate;
ethyl (2-morpholinoethyl)fumarate; and
propyl(morpholinoethyl)fumarate;
or a pharmaceutically acceptable salt of any of the foregoing.

In certain embodiments, any one or more of the compounds of Formula (Ia) provided in the preceding paragraphs is a hydrochloride salt.

In certain embodiments, a compound of Formula (I) has the structure of Formula (Ib):

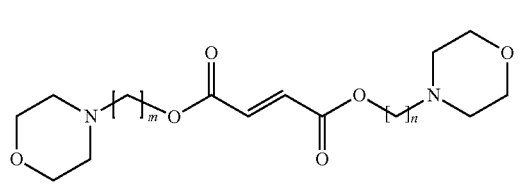

(Ib)

or a pharmaceutically acceptable salt thereof, wherein n is an integer from 2 to 6; and m is an integer from 2 to 6.

In certain embodiments of a compound of Formula (Ib), n is 2. In certain embodiments of a compound of Formula (Ib) where n is 2, the compound is chosen from:
bis(2-morpholinoethyl)fumarate;
2-morpholinoethyl (3-morpholinopropyl)fumarate;
4-morpholinobutyl (2-morpholinoethyl)fumarate;
2-morpholinoethyl (5-morpholinopentyl)fumarate; and
2-morpholinoethyl (6-morpholinohexyl)fumarate;
or a pharmaceutically acceptable salt of any of the foregoing.

In certain embodiments of a compound of Formula (Ib), n is 3. In certain embodiments of a compound of Formula (Ib) where n is 3, the compound is chosen from:
2-morpholinoethyl (3-morpholinopropyl)fumarate;
bis(3-morpholinopropyl)fumarate;
4-morpholinobutyl (3-morpholinopropyl)fumarate;
5-morpholinopentyl (3-morpholinopropyl)fumarate; and
6-morpholinohexyl (3-morpholinopropyl)fumarate;
or a pharmaceutically acceptable salt of any of the foregoing.

In certain embodiments of a compound of Formula (Ib), n is 4. In certain embodiments of a compound of Formula (Ib) where n is 4, the compound is chosen from:
4-morpholinobutyl (2-morpholinoethyl)fumarate;
4-morpholinobutyl (3-morpholinopropyl)fumarate;
bis(4-morpholinobutyl)fumarate;
4-morpholinobutyl (5-morpholinopentyl)fumarate; and
4-morpholinobutyl (6-morpholinohexyl)fumarate;

or a pharmaceutically acceptable salt of any of the foregoing.

In certain embodiments of a compound of Formula (Ib), n is 5. In certain embodiments of a compound of Formula (Ib) where n is 5, the compound is chosen from:
2-morpholinoethyl (5-morpholinopentyl)fumarate;
5-morpholinopentyl (3-morpholinopropyl)fumarate;
4-morpholinobutyl (5-morpholinopentyl)fumarate;
bis(5-morpholinopentyl)fumarate; and
6-morpholinohexyl (5-morpholinopentyl)fumarate;
or a pharmaceutically acceptable salt of any of the foregoing.

In certain embodiments of a compound of Formula (Ib), n is 6. In certain embodiments of a compound of Formula (Ib) where n is 6, the compound is chosen from:
2-morpholinoethyl(6-morpholinohexyl)fumarate;
6-morpholinohexyl (3-morpholinopropyl)fumarate;
4-morpholinobutyl (6-morpholinohexyl)fumarate;
6-morpholinohexyl (5-morpholinopentyl)fumarate; and
bis(6-morpholinohexyl)fumarate;
or a pharmaceutically acceptable salt of any of the foregoing.

In certain embodiments of compounds of Formula (Ib), the compound is chosen from:
2-morpholinoethyl(morpholinopropyl)fumarate; and
bis(2-morpholinoethyl)fumarate;
or a pharmaceutically acceptable salt of any of the foregoing.

In certain embodiments, any one or more of the compounds of Formula (Ib) provided in the preceding paragraphs is a hydrochloride salt.

Compounds of Formula (I) may be pharmacologically active or may be metabolized in vivo to produce metabolites that are pharmacologically active.

Compounds provided by the present disclosure include compounds of Formula (II). Compounds of Formula (II) may optionally be produced by in vivo metabolism of the corresponding compound of Formula (I), i.e., by cleavage of the corresponding $R^1$ moiety. Alternatively, a compound of Formula (II) may be administered directly to a patient, for example by placing the compound in a pharmaceutical preparation or dosage form that is administered to the patient. Thus, the Formula (II) compounds are themselves pharmacologically active and require no further metabolism to become pharmacologically active.

Accordingly, certain embodiments provide a compound of Formula (II):

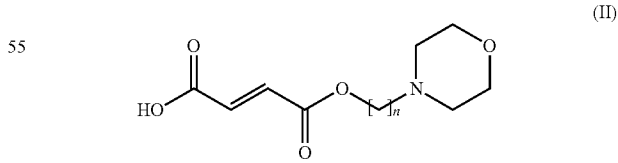

(II)

or a pharmaceutically acceptable salt thereof, wherein n is an integer from 2 to 6.

Certain embodiments provide a pharmaceutical composition comprising a pharmaceutically acceptable vehicle and a therapeutically effective amount of a compound of Formula (II):

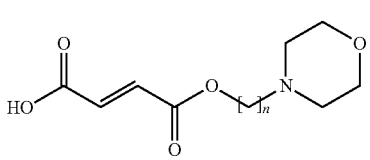
(II)

or a pharmaceutically acceptable salt thereof, wherein n is an integer from 2 to 6.

In certain embodiments of a compound of Formula (II), n is 2, n is 3, n is 4, n is 5, and in certain embodiments, n is 6.

In certain embodiments of a compound of Formula (II), the compound is a pharmaceutically acceptable salt.

In certain embodiments of a compound of Formula (II), the compound is the hydrochloride salt.

In certain embodiments of a compound of Formula (II), the compound is chosen from:
(E)-4-(2-morpholinoethoxy)-4-oxobut-2-enoic acid;
(E)-4-(3-morpholinopropoxy)-4-oxobut-2-enoic acid;
(E)-4-(4-morpholinobutoxy)-4-oxobut-2-enoic acid;
(E)-4-(5-morpholinopentoxy)-4-oxobut-2-enoic acid; and
(E)-4-(6-morpholinohexoxy)-4-oxobut-2-enoic acid;
or a pharmaceutically acceptable salt of any of the foregoing.

In a specific aspect, provided here are compounds according to Formula (I):

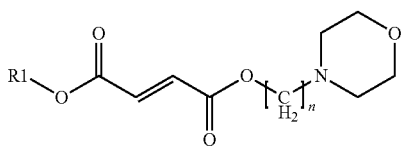
(I)

or a pharmaceutically acceptable salt thereof;
wherein:
n is an integer from 2 to 6;
$R^1$ is selected from H, methyl, ethyl, $C_{3-6}$ alkyl, and

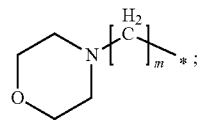

and
m is an integer from 2 to 6;
provided that
i) when n is 2, and $R^1$ is

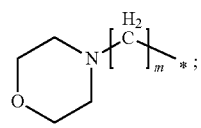

then m is 3, 4, 5, or 6; and
ii) when $R^1$ is H, then n is 4, 5, or 6.

In one embodiment, with respect to the compounds of Formula (I), the compound is a compound according to Formula (IIa), (IIb), (IIc), (IId), or (IIe):

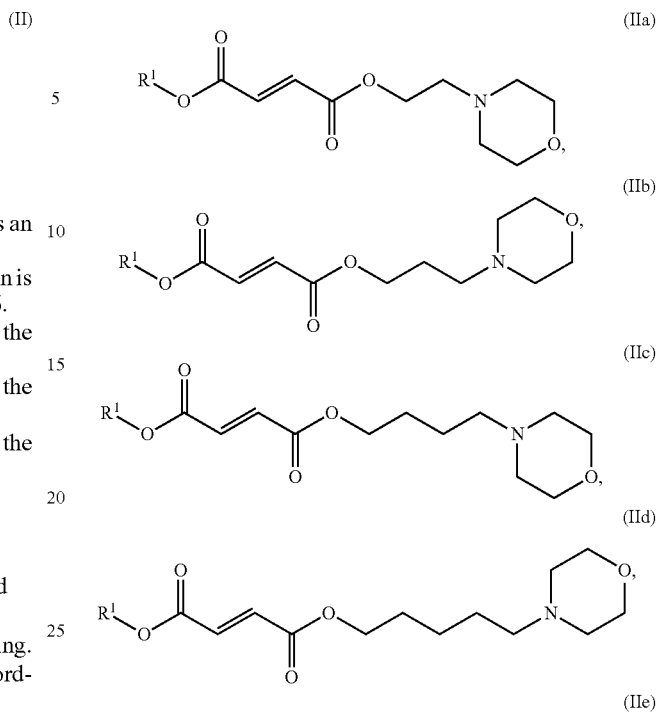

or a pharmaceutically acceptable salt thereof; and wherein $R^1$ is as described for Formula (I).

In one embodiment, with respect to the compounds of Formula (I), (IIa), (IIb), (IIc), (IId), or (IIe), $R^1$ is methyl, ethyl, or $C_{3-6}$ alkyl. In another embodiment, $R^1$ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentuyl, 4-methylpentyl, 3-methylpentan-2-yl, 4-methylpentan-2-yl, 2,3-dimethylbutyl, or 3,3-dimethylbutyl. In a particular embodiment, $R^1$ is methyl.

In one embodiment, with respect to the compounds of Formula (I), $R^1$ is

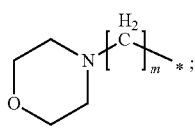

n is 2; and m is 3, 4, 5, or 6.

In another embodiment, with respect to the compounds of Formula (I), $R^1$ is

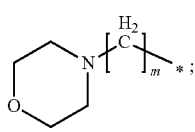

and n is 3, 4, 5, or 6; and m is 2, 3, 4, 5, or 6.

In another embodiment, with respect to the compounds of Formula (I), $R^1$ is H; and n is 4, 5, or 6.

In another embodiment, with respect to the compounds of Formula (I), the compound is a compound according to Formula (IIIa), (IIIb), (IIIc), (IIId), or (IIIe):

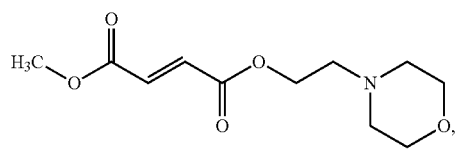

(IIIa)

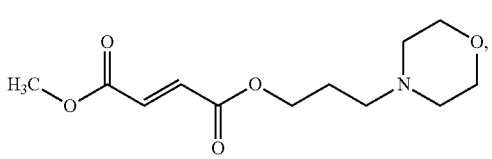

(IIIb)

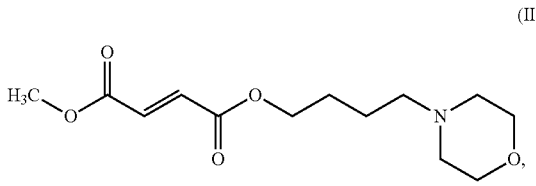

(IIIc)

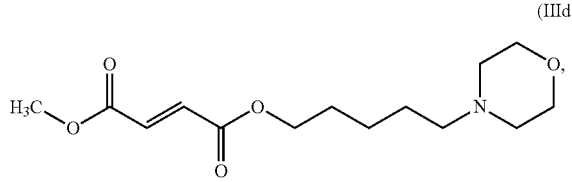

(IIId)

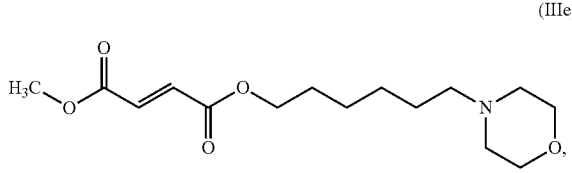

(IIIe)

or a pharmaceutically acceptable salt thereof.

In another embodiment, with respect to the compounds of Formula (I), the compound is a compound according to Formula (IVc), (IVd), or (IVe):

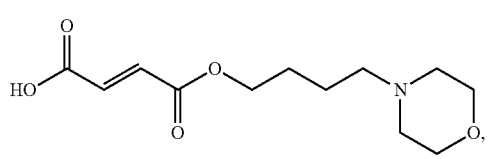

(IVc)

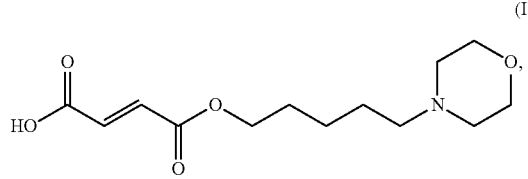

(IVd)

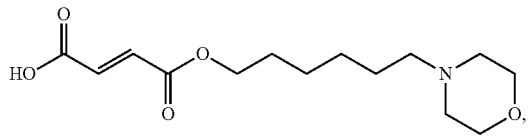

(IVe)

or a pharmaceutically acceptable salt thereof.

In another embodiment, with respect to the compounds of Formula (I), (IIa)-(IIe), (IIIa)-(IIIe), and (IVc)-(IVe), the compound is a pharmaceutically acceptable salt. In a particular embodiment, the compound is a HCl salt.

In a specific embodiment, with respect to the compounds of Formula (I), the compound is any one of the compounds listed in Table 1.

In a particular embodiment, with respect to the compounds of Formula (I), the compound according to Formula (IIIc):

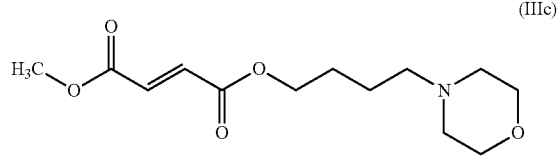 [SMILES: COC(=O)/C=C/C(=O)OCCCCN1CCOCC1]

(IIIc)

or a pharmaceutically acceptable salt thereof.

In a more particular embodiment, with respect to the compounds of Formula (I), the compound is a HCl salt of (IIIc).

In another specific aspect, provided here are pharmaceutical compositions comprising a pharmaceutically acceptable vehicle and a therapeutically effective amount of a compound of Formula (I):

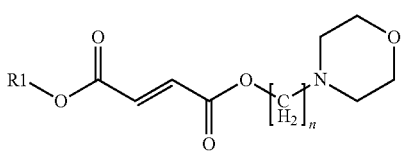

(I)

or a pharmaceutically acceptable salt thereof;
wherein:
n is an integer from 2 to 6;
$R^1$ is selected from H, methyl, ethyl, $C_{3-6}$ alkyl, and

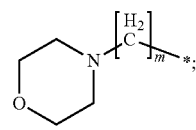

and
m is an integer from 2 to 6.

In one embodiment, with respect to the pharmaceutical compositions, the compound is a compound according to Formula (IIa), (IIb), (IIc), (IId), or (IIe) or a pharmaceutically acceptable salt thereof; and wherein $R^1$ is as described for Formula (I); and Formulae (IIa)-(IIe) are as depicted above.

In one embodiment, with respect to the pharmaceutical compositions of Formula (I), (IIa), (IIb), (IIc), (IId), or (IIe), $R^1$ is methyl, ethyl, or $C_{3-6}$ alkyl. In another embodiment, $R^1$ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentuyl, 4-methylpentyl, 3-methylpentan-2-yl, 4-methylpentan-2-yl, 2,3-dimethylbutyl, or 3,3-dimethylbutyl. In a particular embodiment, $R^1$ is methyl.

In one embodiment, with respect to the pharmaceutical compositions of Formula (I), $R^1$ is

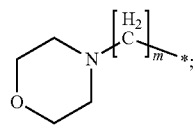

and m is 2, 3, 4, 5, or 6.

In another embodiment, with respect to the pharmaceutical compositions of Formula (I) (IIa), (IIb), (IIc), (IId), or (IIe), $R^1$ is H. In one embodiment, $R^1$ is H; and n is 2. In another embodiment, $R^1$ is H; and n is 3. In a yet another embodiment, $R^1$ is H; and n is 4, 5, or 6.

In another embodiment, with respect to the pharmaceutical compositions of Formula (I), the compound is a compound according to Formula (IIIa), (IIIb), (IIIc), (IIId), or (IIIe), or a pharmaceutically acceptable salt thereof; and Formulae are as depicted above.

In another embodiment, with respect to the pharmaceutical compositions of Formula (I), (IIa)-(IIe), and (IIIa)-(IIIe), the compound is a pharmaceutically acceptable salt. In a particular embodiment, the compound is a HCl salt.

In a specific embodiment, with respect to the pharmaceutical compositions of Formula (I), the compound is any one of the compounds listed in Table 1.

In a particular embodiment, with respect to the pharmaceutical compositions of Formula (I), the compound according to Formula (IIIc):

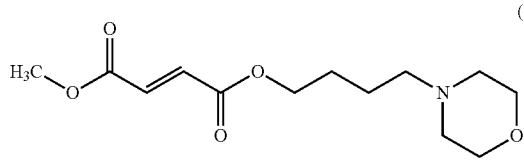

(IIIc)

or a pharmaceutically acceptable salt thereof.

In a more particular embodiment, with respect to the pharmaceutical compositions of Formula (I), the compound is a HCl salt of (IIIc).

In another specific aspect, provided here are method for preventing or treating in a mammal in need thereof a disease or condition which comprises administering to the mammal an effective disease-treating or condition-treating amount of a compound according to Formula (I):

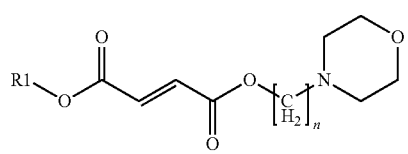

(I)

or a pharmaceutically acceptable salt thereof;

wherein:

n is an integer from 2 to 6;

$R^1$ is selected from H, methyl, ethyl, $C_{3-6}$ alkyl, and

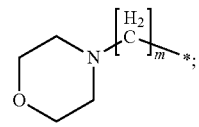

and m is an integer from 2 to 6.

In one embodiment, with respect to the methods, the compound is a compound according to Formula (IIa), (IIb), (IIc), (IId), or (IIe) or a pharmaceutically acceptable salt thereof; and $R^1$ is as described for Formula (I); and Formulae (IIa)-(IIe) are as depicted above.

In one embodiment, with respect to the methods, the compound is a compound according to Formula (I), (IIa), (IIb), (IIc), (IId), or (IIe), and $R^1$ is methyl, ethyl, or $C_{3-6}$ alkyl. In another embodiment, $R^1$ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentuyl, 4-methylpentyl, 3-methylpentan-2-yl, 4-methylpentan-2-yl, 2,3-dimethylbutyl, or 3,3-dimethylbutyl. In a particular embodiment, $R^1$ is methyl.

In one embodiment, with respect to the methods, the compound is a compound according to Formula (I), $R^1$ is

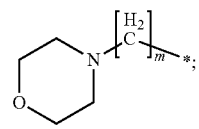

and m is 2, 3, 4, 5, or 6.

In another embodiment, with respect to the methods, the compound is a compound according to Formula (I) (IIa), (IIb), (IIc), (IId), or (IIe), and $R^1$ is H. In one embodiment, $R^1$ is H; and n is 2. In another embodiment, $R^1$ is H; and n is 3. In a yet another embodiment, $R^1$ is H; and n is 4, 5, or 6.

In another embodiment, with respect to the methods, the compound is a compound according to Formula (I), and the compound is a compound according to Formula (IIIa), (IIIb), (IIIc), (IIId), or (IIIe), or a pharmaceutically acceptable salt thereof; and Formulae (IIIa)-(IIIe) are as depicted above.

In another embodiment, with respect to the methods, the compound is a compound according to Formula (I), (IIa)-(IIe), and (IIIa)-(IIIe), and the compound is a pharmaceutically acceptable salt. In a particular embodiment, the compound is a HCl salt.

In a specific embodiment, with respect to the methods, the compound is any one of the compounds listed in Table 1.

In a particular embodiment, with respect to the methods, the compound is according to Formula (IIIc):

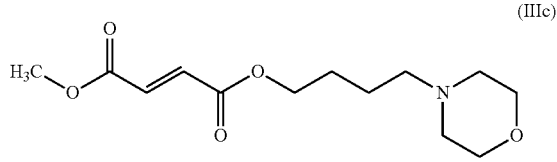 [SMILES: COC(=O)/C=C/C(=O)OCCCCN1CCOCC1]

(IIIc)

or a pharmaceutically acceptable salt thereof.

In a more particular embodiment, with respect to the methods, the compound is a HCl salt of (IIIc).

In one embodiment, with respect to the methods, the disease or condition is selected from a neurodegenerative disease, an inflammatory disease, and an autoimmune disease. In certain embodiments, the disease or condition is selected from multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

Synthesis

Compounds disclosed herein may be obtained via the synthetic methods illustrated in Schemes 1 through 4. In addition, general synthetic methods useful in the synthesis of compounds described herein are available in the art. Starting materials useful for preparing compounds and intermediates thereof and/or practicing methods described herein are commercially available or can be prepared by well-known synthetic methods. The methods presented in the schemes provided by the present disclosure are illustrative rather than comprehensive. It will be apparent to those skilled in the art that many modifications, both to materials and methods, may be practiced without departing from the scope of the disclosure.

Certain of the halo alkyl morpholines useful for preparing compounds of the disclosure are available from commercial sources. Non-commercially available halo alkyl morpholines useful for preparing compounds of the disclosure, and intermediates thereof may be prepared by well-known synthetic methods such as those described in Schemes 1 and 2.

Functionalized 1-halo alkyl morpholines useful for the preparation of morpholinoalkyl fumarates of compounds of the disclosure may be prepared according to Scheme 1:

Scheme 1

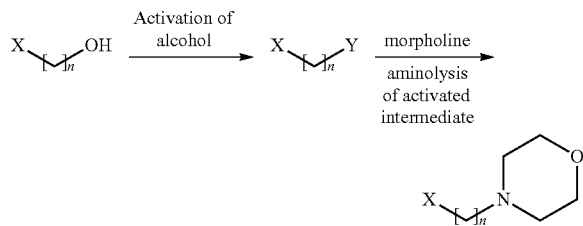

where X and Y are leaving groups such as halogen and n is as defined in Formula (I) and Formula (II). In certain embodiments of Scheme 1, X is chloro and Y is selected from chloro and an O-acylisourea.

Chemical activation of the alcohol to the corresponding chloride as shown in Scheme 1 may be achieved by reaction with chlorination agents such as thionyl chloride ($SOCl_2$), oxalyl chloride ($C_2O_2Cl_2$), or phosphorous pentachloride ($PCl_5$), optionally in the presence of a suitable catalyst such as N,N-dimethylformamide, and either in substance (absence of solvent) or in an inert organic solvent such as dichloromethane (DCM) at an appropriate temperature such as from about 0° C. to about 70° C. Chemical activation of the alcohol may be performed in situ and without isolating the activated substrate prior to the following aminolysis step. Optionally, the activated alcohol may be isolated and/or purified using methods well known in the art, i.e. fractional distillation.

Alternatively, carbodiimide dehydration agents such as N,N'-diisopropylcarbodiimide (DIC), N,N-dicyclohexylcarbodiimide (DCC), or 1-ethyl-3-(3-dimethylaminopropyl)carbodiimide (EDAC, EDC), optionally in the presence of a catalytic or stoichiometric amount of a suitable additive such as 4-(N,N-dimethylaminopyridine)(DMAP) (Steglich esterification conditions), 1-hydroxybenzotriazole (HOBt), 1-hydroxy-7-aza-benzotriazole (HOAt), or N-hydroxysuccinimide (NHS); uronium or phosphonium salts with non-nucleophilic anions such as N-[(1H-benzotriazol-1-yl)(dimethylamino)methylene]-N-methylmetanaminium hexafluorophosphate (HBTU), N-[(dimethylamino)-1H-1,2,3-triazolo[4,5-b]pyridin-1-ylmethylene]-N-methylmetanaminium hexafluorophosphate N-oxide (HATU), N-[(1H-benzotriazol-1-yl)(dimethylamino)methylene]-N-methylmetanaminium tetrafluoroborate (TBTU), or benzotriazol-1-yl-oxytripyrrolidinophosphonium hexafluorophosphate (PyBOP), can be employed to form an activated carboxylic acid derivative. Optionally, organic tertiary bases such as triethylamine (TEA) or diisopropylethylamine (DIEA) can also be employed. The formation of the activated carboxylic acid derivative can take place in an inert solvent such as dichloromethane (DCM), N,N-dimethylformamide, N-methylpyrrolidone (NMP), N,N-dimethylacetamide (DMA, DMAc), or mixtures of any of the foregoing at an appropriate temperature such as from about 0° C. to about 40° C.

Aminolysis of in situ generated or isolated activated carboxylic derivatives with the appropriately functionalized amine derivative (morpholine) (Scheme 2) can take place in the presence of a suitable base such as an organic tertiary base, i.e., triethylamine (TEA), diethylaminoethylamine (DIEA), pyridine, or mixtures of any of the foregoing, optionally in the presence of suitable additives such as nucleophilic acylation catalysts, i.e., 4-(N,N-dimethylaminopyridine) (DMAP), and in the same or other inert solvent as used for the activation step such as dichloromethane (DCM), N,N-dimethylformamide, N-methylpyrrolidone (NMP), N,N-dimethylacetamide (DMA, DMAc), or mixtures of any of the foregoing, at an appropriate temperature such as from about 0° C. to about 70° C.

Functionalized 1-hydroxy alkyl morpholines useful for the preparation of morpholinoalkyl fumarates of the compounds of disclosure may be also prepared according to Scheme 2:

Scheme 2

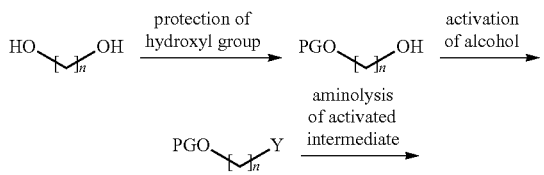

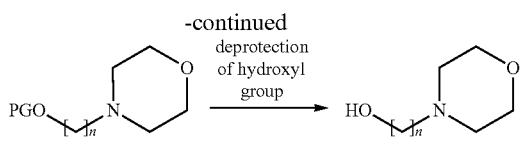

where PG is a hydroxyl protecting group; Y is a leaving group such as chloro or an O-isourea derived radical; and n is as defined in Formula (I) and Formula (II).

Certain of the functionalized and activated diols are commercially available. Methods for introducing hydroxyl protecting groups (PGs) are well known in the art. Useful protecting groups to temporarily block the hydroxyl group of functionalized diols include certain alkyl ethers such as (substituted) benzyl ethers, tert-butyl ethers, trityl ether, or various silyl ethers such as tert-butyl dimethylsilyl ether, triisopropylsilyl ether, or tert-butyldiphenylsilyl ethers.

Certain protected, functionalized and activated diols are commercially available. Alternatively, the chemical activation of the protected and functionalized diols to the corresponding activated alcohol, i.e., alcohol chloride, may be achieved using similar reaction procedures and conditions as those described in Scheme 1 for the activation of functionalized 1-halo alcohols.

Aminolysis of in situ generated or isolated protected, functionalized, and activated 1-hydroxy derivatives with morpholine may take place using similar reaction procedures and conditions as those described in Scheme 1 for the aminolysis of functionalized, protected, and activated 1-halo alcohols.

Orthogonal (or ordered) deprotection of the protected 1-hydroxyacetic acid derivative liberates the corresponding free hydroxyl group. Deprotection methods, procedures, and practices are well known in the art.

In certain embodiments, the protecting group can be an alkyl group such as a tert-butyl group. Deprotection may be carried out by contacting a tert-butyl protected functionalized 1-hydroxy acetamide derivative with an excess of a strong Brønsted acid such as trifluoroacetic acid (TFA) or hydrogen chloride (HCl) in an inert solvent such as dichloromethane (DCM), diethyl ether ($Et_2O$), 1,4-dioxane, or mixtures of any of the foregoing, at an appropriate temperature such as from about 0° C. to about 40° C.

In certain embodiments, the protecting group can be chosen from an alkyl group such as a benzyl group. When the protecting group is a benzyl group, deprotection may be carried out by reacting the functionalized 1-hydroxy acetamide derivative with gaseous hydrogen ($H_2$) in the presence of a heterogeneous catalyst, i.e., 5-10 wt-% palladium on activated carbon (activated or wet coal), in a solvent such as methanol (MeOH), ethanol (EtOH), ethyl acetate (EtOAc), or mixtures of any of the foregoing, optionally in the presence of a small amount of an activator such as 1 N aq. hydrochloric acid at an appropriate temperature such as from about 0° C. to about 40° C. and under a hydrogen atmosphere at a pressure of about 15 psi to about 60 psi.

Morpholinoalkyl fumarates of Formula (I) and Formula (II) can be prepared according to Scheme 3:

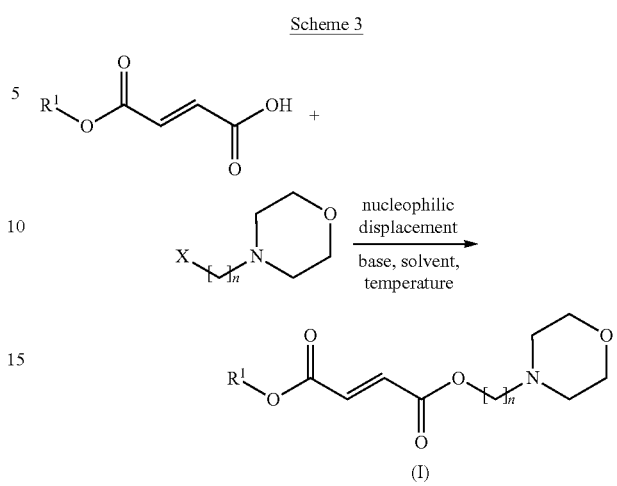

where X is a leaving group such as halogen, and $R^1$ and n are as defined in Formula (I) or $R^1$ is hydrogen as defined in Formula (II). In certain embodiments of Scheme 3, X is chloro and $R^1$ is $C_{1-6}$ alkyl such as methyl or ethyl.

Nucleophilic displacement of the monoalkyl fumaric acid with the functionalized 1-halo alkyl morpholine (Scheme 1) as shown in Scheme 3 may take place in the presence of an inorganic base such as an alkali carbonate such as cesium hydrogencarbonate ($CsHCO_3$), cesium carbonate ($Cs_2CO_3$), or potassium carbonate ($K_2CO_3$). Optionally, organic tertiary bases such as triethylamine (TEA), diisopropylethylamine (DIEA), or amidine; guanidine-based bases such as 1,5-diazabicyclo[4.3.0]non-5-ene (DBN), 1,8-diazabicyclo[5.4.0]undec-7-ene (DBU) or 1,1,3,3-tetramethylguanidine (TMG); silver salts such silver(I) oxide ($Ag_2O$) or silver(I) carbonate ($Ag_2CO_3$); or other halide scavengers known in the art can be employed. The corresponding alkali, tri- and tetraalkylammonium, amidine, or guanide salts of the monoalkyl fumarate can be generated in situ or, alternatively, can be prepared separately. The reaction can take place in an inert solvent such as N,N-dimethylformamide, N-methylpyrrolidone (NMP), N,N-dimethylacetamide (DMA, DMAc), dimethylsulfoxide (DMSO), tetrahydrofuran (THF), toluene, or mixtures of any of the foregoing at an appropriate temperature such as from about room temperature to about 70° C.

Morpholinoalkyl fumarates of Formula (I) and Formula (II) may also be prepared according to Scheme 4:

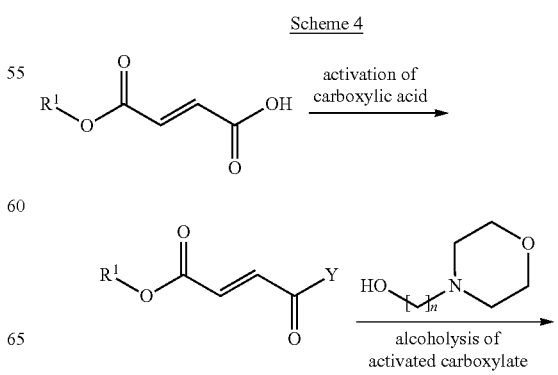

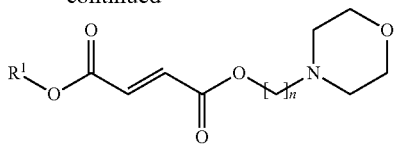

where Y is a suitable leaving group such as halogen, an O-acylisourea, various triazolol esters, or others; and $R^1$ and n are as defined herein. In certain embodiments of Scheme 4, Y is chloro and $R^1$ is $C_{1-6}$ alkyl such as methyl or ethyl for a compound of Formula (I) or $R^1$ is hydrogen for a compound of Formula (II).

Chemical activation of the carboxylic acid to the corresponding carboxylic acid chloride as shown in Scheme 4 may be accomplished by reaction with a chlorination agent such as thionyl chloride ($SOCl_2$), oxalyl chloride ($C_2O_2Cl_2$), phosphorous pentachloride ($PCl_5$), or others, optionally in the presence of a catalyst such as N,N-dimethylformamide, and either in substance (absence of solvent) or in an inert organic solvent such as dichloromethane (DCM) at an appropriate temperature such as from about 0° C. to about 70° C. Chemical activation of the carboxylic acid as shown in Scheme 4 may be performed in situ without isolating the activated substrate prior to the subsequent alcoholysis step. Optionally, the activated carboxylic acid chloride may be isolated and/or purified using methods well known in the art, i.e. fractional distillation.

Alternatively, carbodiimide dehydration agents such as N,N-diisopropylcarbodiimide (DIC), N,N-dicyclohexylcarbodiimide (DCC), or 1-ethyl-3-(3-dimethylaminopropyl)carbodiimide (EDAC, EDC), optionally in the presence of a catalytic or stoichiometric amount of an additive such as 4-(N,N-dimethylaminopyridine) (DMAP) (Steglich esterification conditions), 1-hydroxybenzotriazole (HOBt), 1-hydroxy-7-aza-benzotriazole (HOAt), or N-hydroxysuccinimide (HOSu); a uronium or phosphonium salt with non-nucleophilic anions such as N-[(1H-benzotriazol-1-yl)(dimethylamino)methylene]-N-methylmetanaminium hexafluorophosphate (HBTU), N-[(dimethylamino)-1H-1,2,3-triazolo[4,5-b]pyridin-1-ylmethylene]-N-methylmetanaminium hexafluorophosphate N-oxide (HATU), N-[(1H-benzotriazol-1-yl)(dimethylamino)methylene]-N-methylmetanaminium tetrafluoroborate (TBTU), or benzotriazol-1-yl-oxytripyrrolidinophosphonium hexafluorophosphate (PyBOP), may be employed to form an activated monoalkyl fumarate derivative. Optionally, organic tertiary bases such as triethylamine (TEA) or diethylaminoethylamine (DIEA) can also be employed. The formation of activated monoalkyl fumarate derivatives may take place in an inert solvent such as dichloromethane (DCM), N,N-dimethylformamide, N-methylpyrrolidone (NMP), N,N-dimethylacetamide (DMA, DMAc), or mixtures of any of the foregoing at an appropriate temperature such as from about room temperature to about 70° C.

Alcoholysis of the activated monoalkyl fumarate derivative with a functionalized hydroxy alkyl morpholine derivative (Scheme 2) as shown in Scheme 4 may take place in the presence of a base, for example, an organic tertiary base such as, triethylamine (TEA), diethylaminoethylamine (DIEA), or pyridine, optionally in the presence of an additive such as a nucleophilic acylation catalyst, i.e., 4-(N,N-dimethylaminopyridine) (DMAP) (Steglich esterification conditions), and in the same or other inert solvent as used for the activation step such as dichloromethane (DCM), N,N-dimethylformamide, N-methylpyrrolidone (NMP), N,N-dimethylacetamide (DMA, DMAc), or mixtures of any of the foregoing at an appropriate temperature such as from about 0° C. to about 70° C.

Pharmaceutical Compositions

Pharmaceutical compositions provided by the present disclosure may comprise a therapeutically effective amount of a compound of Formula (I) or Formula (II) together with a suitable amount of one or more pharmaceutically acceptable vehicles so as to provide a composition for proper administration to a patient. Suitable pharmaceutical vehicles are described in the art.

In certain embodiments, a compound of Formula (I) or Formula (II) may be incorporated into pharmaceutical compositions to be administered orally. Oral administration of such pharmaceutical compositions may result in uptake of a compound of Formula (I) or Formula (II) throughout the intestine and entry of such compound into the systemic circulation. Such oral compositions may be prepared in a manner known in the pharmaceutical art and comprise a compound of Formula (I) or Formula (II) and at least one pharmaceutically acceptable vehicle. Oral pharmaceutical compositions may include a therapeutically effective amount of a compound of Formula (I) or Formula (II) and a suitable amount of a pharmaceutically acceptable vehicle, so as to provide an appropriate form for oral administration to a patient.

Compounds of Formula (I) or Formula (II) may be incorporated into pharmaceutical compositions to be administered by any appropriate route of administration including intradermal, intramuscular, intraperitoneal, intravenous, subcutaneous, intranasal, epidural, oral, sublingual, intracerebral, intravaginal, transdermal, rectal, inhalation, or topical. In certain embodiments, compounds of Formula (I) or Formula (II) may be incorporated into pharmaceutical compositions to be administered orally.

Pharmaceutical compositions comprising a compound of Formula (I) or Formula (II) and may be manufactured by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers, diluents, excipients, or auxiliaries, which facilitate processing of compounds of Formula (I), Formula (II), or crystalline forms thereof and one or more pharmaceutically acceptable vehicles into formulations that can be used pharmaceutically. Proper formulation is in part dependent upon the route of administration chosen. Pharmaceutical compositions provided by the present disclosure may take the form of solutions, suspensions, emulsions, tablets, pills, pellets, capsules, capsules containing liquids, powders, sustained-release formulations, suppositories, emulsions, aerosols, sprays, suspensions, or any other form suitable for administration to a patient.

Pharmaceutical compositions provided by the present disclosure may be formulated in a unit dosage form. A unit dosage form refers to a physically discrete unit suitable as a unitary dose for patients undergoing treatment, with each unit containing a predetermined quantity of a compound of Formula (I) or Formula (II) calculated to produce an intended therapeutic effect. A unit dosage form may be for a single daily dose, for administration 2 times per day, or one of multiple daily doses, e.g., 3 or more times per day. When multiple daily doses are used, a unit dosage form may be the same or different for each dose. One or more dosage forms may comprise a dose, which may be administered to a patient at a single point in time or during a time interval.

Pharmaceutical compositions comprising a compound of Formula (I) or Formula (II) may be formulated for immediate release.

In certain embodiments, an oral dosage form provided by the present disclosure may be a controlled release dosage form. Controlled delivery technologies can improve the absorption of a drug in a particular region, or regions, of the gastrointestinal tract. Controlled drug delivery systems may be designed to deliver a drug in such a way that the drug level is maintained within a therapeutically effective window and effective and safe blood levels are maintained for a period as long as the system continues to deliver the drug with a particular release profile in the gastrointestinal tract. Controlled drug delivery may produce substantially constant blood levels of a drug over a period of time as compared to fluctuations observed with immediate release dosage forms. For some drugs, maintaining a constant blood and tissue concentration of the drug throughout the course of therapy is the most desirable mode of treatment. Immediate release of drugs may cause blood levels to peak above a level required to elicit a desired response, which may waste the drug and/or may cause or exacerbate toxic side effects. Controlled drug delivery can result in optimum therapy, and not only can reduce the frequency of dosing, but may also reduce the severity of side effects. Examples of controlled release dosage forms include dissolution controlled systems, diffusion controlled systems, ion exchange resins, osmotically controlled systems, erodable matrix systems, pH independent formulations, and gastric retention systems.

An appropriate oral dosage form for a particular pharmaceutical composition provided by the present disclosure may depend, at least in part, on the gastrointestinal absorption properties of a compound of Formula (I) or Formula (II), the stability of a compound of Formula (I) or Formula (II) in the gastrointestinal tract, the pharmacokinetics of a compound of Formula (I) or Formula (II) and the intended therapeutic profile. An appropriate controlled release oral dosage form may be selected for a particular compound of Formula (I) or Formula (II). For example, gastric retention oral dosage forms may be appropriate for compounds absorbed primarily from the upper gastrointestinal tract, and sustained release oral dosage forms may be appropriate for compounds absorbed primarily from the lower gastrointestinal tract. Certain compounds are absorbed primarily from the small intestine. In general, compounds traverse the length of the small intestine in about 3 to 5 hours. For compounds that are not easily absorbed by the small intestine or that do not dissolve readily, the window for active agent absorption in the small intestine may be too short to provide a desired therapeutic effect.

In certain embodiments, pharmaceutical compositions provided by the present disclosure may be practiced with dosage forms adapted to provide sustained release of a compound of Formula (I) or Formula (II) upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

An appropriate dose of a compound of Formula (I) or Formula (II), or pharmaceutical composition comprising a compound of Formula (I) or Formula (II), may be determined according to any one of several well-established protocols. For example, animal studies, such as studies using mice, rats, dogs, and/or monkeys, may be used to determine an appropriate dose of a pharmaceutical compound. Results from animal studies may be extrapolated to determine appropriate doses for use in other species, such as for example, humans.

Uses

Compounds of Formula (I) are derivatives of monoalkyl hydrogen fumarates. Compounds of Formula (II) are morpholinoalkyl esters of fumaric acid. Thus, compounds of Formula (I) or Formula (II) and pharmaceutical compositions thereof may be administered to a patient suffering from any disease including a disorder, condition, or symptom for which monoalkyl hydrogen fumarates and/or fumaric acid esters are known or hereafter discovered to be therapeutically effective. Indications for which methyl hydrogen fumarate (MHF) has been prescribed, and hence for which a compound of Formula (I) or Formula (II), or pharmaceutical compositions thereof are also expected to be effective, include psoriasis. Other indications for which compounds of Formula (I) or Formula (II) may be therapeutically effective include multiple sclerosis, irritable bowel disorder, ulcerative colitis, arthritis, chronic obstructive pulmonary disease, asthma, Parkinson's disease, Huntington's disease, and amyotrophic lateral sclerosis.

Methods of treating a disease in a patient provided by the present disclosure comprise administering to a patient in need of such treatment a therapeutically effective amount or dose of a compound of Formula (I) or Formula (II). Compounds of Formula (I) or Formula (II) or pharmaceutical compositions thereof may provide therapeutic or prophylactic plasma and/or blood concentrations of fumarate following administration to a patient.

Morpholinoalkyl fumarates of Formula (I) or Formula (II) may be included in a pharmaceutical composition and/or dosage form adapted for oral administration, although compounds of Formula (I) or Formula (II) may also be administered by any other appropriate route, such as for example, by injection, infusion, inhalation, transdermally, or absorption through epithelial or mucosal membranes (e.g., oral, rectal, and/or intestinal mucosa).

Morpholinoalkyl fumarates of Formula (I) or Formula (II) may be administered in an amount and using a dosing schedule as appropriate for treatment of a particular disease. Daily doses of compounds of Formula (I) or Formula (II) may range from about 0.01 mg/kg to about 50 mg/kg, from about 0.1 mg/kg to about 50 mg/kg, from about 1 mg/kg to about 50 mg/kg, and in certain embodiments, from about 5 mg/kg to about 25 mg/kg. In certain embodiments, compounds of Formula (I) or Formula (II) may be administered at a dose over time from about 1 mg to about 5 g per day, from about 10 mg to about 4 g per day, and in certain embodiments from about 20 mg to about 2 g per day. An appropriate dose of a compound of Formula (I) or Formula (II) may be determined based on several factors, including, for example, the body weight and/or condition of the patient being treated, the severity of the disease being treated, the incidence and/or severity of side effects, the manner of administration, and the judgment of the prescribing physician. Appropriate dose ranges may be determined by methods known to those skilled in the art.

Compounds of Formula (I) or Formula (II) may be assayed in vitro and in vivo for the desired therapeutic or prophylactic activity prior to use in humans. In vivo assays, for example using appropriate animal models, may also be used to determine whether administration of a compound of Formula (I) or Formula (II) is therapeutically effective.

In certain embodiments, a therapeutically effective dose of a compound of Formula (I) or Formula (II) may provide therapeutic benefit without causing substantial toxicity including adverse side effects. Toxicity of compounds of Formula (I) or Formula (II) and/or metabolites thereof may be determined using standard pharmaceutical procedures and may be ascertained by those skilled in the art. The dose ratio between toxic and therapeutic effect is the therapeutic index. A dose of a compound of Formula (I) or Formula (II) may be within a range capable of establishing and maintaining a therapeutically effective circulating plasma and/or blood concentration of a compound of Formula (I) or Formula (II) that exhibits little or no toxicity.

Compounds of Formula (I) or Formula (II) may be used to treat diseases, disorders, conditions, and symptoms of any of the foregoing for which alkyl hydrogen fumarates, such as MHF, are known to provide or are later found to provide therapeutic benefit. MHF is known to be effective in treating psoriasis, multiple sclerosis, an inflammatory bowel disease, asthma, chronic obstructive pulmonary disease, and arthritis. Hence, compounds of Formula (I) or Formula (II) may also be used to treat any of these diseases and disorders. The underlying etiology of any of the foregoing diseases being treated may have a multiplicity of origins. Further, in certain embodiments, a therapeutically effective amount of one or more compounds of Formula (I) or Formula (II) may be administered to a patient, such as a human, as a preventative measure against various diseases or disorders. Thus, a therapeutically effective amount of one or more compounds of Formula (I) or Formula (II) may be administered as a preventative measure to a patient having a predisposition for and/or history of immunological, autoimmune, and/or inflammatory diseases including psoriasis, arthritis, asthma, and chronic obstructive pulmonary disease; cardiac insufficiency including left ventricular insufficiency, myocardial infarction, and angina pectoris; mitochondrial and neurodegenerative diseases such as Parkinson's disease, Alzheimer's disease, Huntington's disease, amyotrophic lateral sclerosis, retinopathia pigmentosa, and mitochondrial encephalomyopathy; transplantation rejection; autoimmune diseases such as multiple sclerosis; ischemia and reperfusion injury; AGE-induced genome damage; inflammatory bowel diseases such as Crohn's disease, irritable bowel disorder, and ulcerative colitis; and NF-κB mediated diseases.

Psoriasis

Psoriasis is characterized by hyperkeratosis and thickening of the epidermis as well as by increased vascularity and infiltration of inflammatory cells in the dermis. Psoriasis vulgaris manifests as silvery, scaly, erythematous plaques on typically the scalp, elbows, knees, and buttocks. Guttate psoriasis occurs as tear-drop size lesions.

Fumaric acid esters are recognized for the treatment of psoriasis and dimethyl fumarate is approved for the systemic treatment of psoriasis in Germany (Mrowietz and Asadullah, *Trends Mol Med* 2005, 11(1), 43-48; and Mrowietz et al., *Br J Dermatology* 1999, 141, 424-429).

Efficacy of compounds of Formula (I) or Formula (II) for treating psoriasis can be determined using animal models and in clinical trials.

Inflammatory Arthritis

Inflammatory arthritis includes diseases such as rheumatoid arthritis, juvenile rheumatoid arthritis (juvenile idiopathic arthritis), psoriatic arthritis, and ankylosing spondylitis produce joint inflammation. The pathogenesis of immune-mediated inflammatory diseases including inflammatory arthritis is believed to involve TNF and NF-κB signaling pathways (Tracey et al., *Pharmacology & Therapeutics* 2008, 117, 244-279). DMF has been shown to inhibit TNF and inflammatory diseases including inflammatory arthritis, which are believed to involve TNF and NK-κB signaling, and therefore may be useful in treating inflammatory arthritis (Lowewe et al., *J Immunology* 2002, 168, 4781-4787).

The efficacy of compounds of Formula (I) or Formula (II) for treating inflammatory arthritis can be determined using animal models and in clinical trials.

Multiple Sclerosis

Multiple sclerosis (MS) is an inflammatory autoimmune disease of the central nervous system caused by an autoimmune attack against the insulating axonal myelin sheaths of the central nervous system. Demyelination leads to the breakdown of conduction and to severe disease with destruction of local axons and irreversible neuronal cell death. The symptoms of MS are highly varied with each individual patient exhibiting a particular pattern of motor, sensible, and sensory disturbances. MS is typified pathologically by multiple inflammatory foci, plaques of demyelination, gliosis, and axonal pathology within the brain and spinal cord, all of which contribute to the clinical manifestations of neurological disability (see e.g., Wingerchuk, *Lab Invest* 2001, 81, 263-281; and Virley, *NeuroRx* 2005, 2(4), 638-649). Although the causal events that precipitate MS are not fully understood, evidence implicates an autoimmune etiology together with environmental factors, as well as specific genetic predispositions. Functional impairment, disability, and handicap are expressed as paralysis, sensory and octintive disturbances, spasticity, tremor, a lack of coordination, and visual impairment, which impact the quality of life of the individual. The clinical course of MS can vary from individual to individual, but invariability of the disease can be categorized in three forms: relapsing-remitting, secondary progressive, and primary progressive.

Studies support the efficacy of fumaric acid esters for treating MS, which are presently undergoing phase II clinical testing (Schimrigk et al., *Eur J Neurology* 2006, 13, 604-610; and Wakkee and Thio, *Current Opinion Investigational Drugs* 2007, 8(11), 955-962).

Assessment of MS treatment efficacy in clinical trials can be accomplished using tools such as the Expanded Disability Status Scale and the MS Functional as well as magnetic resonance imaging lesion load, biomarkers, and self-reported quality of life. Animal models of MS shown to be useful to identify and validate potential therapeutics include experimental autoimmune/allergic encephalomyelitis (EAE) rodent models that simulate the clinical and pathological manifestations of MS and nonhuman primate EAE models.

Inflammatory Bowel Disease (Crohn's Disease, Ulcerative Colitis)

Inflammatory bowel disease (IBD) is a group of inflammatory conditions of the large intestine and in some cases, the small intestine that includes Crohn's disease and ulcerative colitis. Crohn's disease, which is characterized by areas of inflammation with areas of normal lining in between, can affect any part of the gastrointestinal tract from the mouth to the anus. The main gastrointestinal symptoms are abdominal pain, diarrhea, constipation, vomiting, weight loss, and/or weight gain. Crohn's disease can also cause skin rashes, arthritis, and inflammation of the eye. Ulcerative colitis is characterized by ulcers or open sores in the large intestine or colon. The main symptom of ulcerative colitis is typically constant diarrhea with mixed blood of gradual onset. Other types of intestinal bowel disease include collagenous colitis, lymphocytic colitis, ischemic colitis, diversion colitis, Bechet's colitis, and indeterminate colitis.

FAEs are inhibitors of NF-κB activation and therefore may be useful in treating inflammatory diseases such as Crohn's disease and ulcerative colitis (Atreya et al., *J Intern Med* 2008, 263(6), 59106).

The efficacy of compounds of Formula (I) or Formula (II) for treating inflammatory bowel disease can be evaluated using animal models and in clinical trials. Useful animal models of inflammatory bowel disease are known.

Irritable Bowel Syndrome

Irritable bowel syndrome is a disorder that affects the large intestine and is typically characterized by abdominal pain or cramping, a bloated feeling, flatulence, diarrhea or constipation and/or mucus in the stool.

The efficacy of compounds of Formula (I) or Formula (II) for treating irritable bowel syndrome can be evaluated using animal models and in clinical trials. Useful animal models of inflammatory bowel disease are known.

Asthma

Asthma is reversible airway obstruction in which the airway occasionally constricts, becomes inflamed, and is lined with an excessive amount of mucus. Symptoms of asthma include dyspnea, wheezing, chest tightness, and cough. Asthma episodes may be induced by airborne allergens, food allergies, medications, inhaled irritants, physical exercise, respiratory infection, psychological stress, hormonal changes, cold weather, or by other factors.

As an inhibitor of NF-κB activation and as shown in animal studies (Joshi et al., US 2007/0027076) FAEs may be useful in treating pulmonary diseases such as asthma and chronic obstructive pulmonary disorder.

The efficacy of compounds of Formula (I) or Formula (II) for treating asthma can be assessed using animal models and in clinical trials.

Chronic Obstructive Pulmonary Disease

Chronic obstructive pulmonary disease (COPD), also known as chronic obstructive airway disease, is a group of diseases characterized by the pathological limitation of airflow in the airway that is not fully reversible, and includes conditions such as chronic bronchitis, emphysema, as well as other lung disorders such as asbestosis, pneumoconiosis, and pulmonary neoplasms (see, e.g., Barnes, *Pharmacological Reviews* 2004, 56(4), 515-548). The airflow limitation is usually progressive and associated with an abnormal inflammatory response of the lungs to noxious particles and gases. COPD is characterized by a shortness of breath that lasts for months or years, possibly accompanied by wheezing, and a persistent cough with sputum production. COPD is most often caused by tobacco smoking, although it can also be caused by other airborne irritants such as coal dust, asbestos, urban pollution, or solvents. COPD encompasses chronic obstructive bronchiolitis with fibrosis and obstruction of small airways, and emphysema with enlargement of airspaces and destruction of lung parenchyma, loss of lung elasticity, and closure of small airways.

The efficacy of administering at least one compound of Formula (I) or Formula (II) for treating chronic obstructive pulmonary disease may be assessed using animal models of chronic obstructive pulmonary disease and in clinical studies. For example, murine models of chronic obstructive pulmonary disease are known.

Neurodegenerative Disorders

Neurodegenerative diseases such as Parkinson's disease, Alzheimer's disease, Huntington's disease and amyotrophic lateral sclerosis are characterized by progressive dysfunction and neuronal death. NF-κB inhibition has been proposed as a therapeutic target for neurodegenerative diseases (Camandola and Mattson, *Expert Opin Ther Targets* 2007, 11(2), 123-32).

Parkinson's Disease

Parkinson's disease is a slowly progressive degenerative disorder of the nervous system characterized by tremor when muscles are at rest (resting tremor), slowness of voluntary movements, and increased muscle tone (rigidity). In Parkinson's disease, nerve cells in the basal ganglia, e.g., substantia nigra, degenerate, and thereby reduce the production of dopamine and the number of connections between nerve cells in the basal ganglia. As a result, the basal ganglia are unable to control smooth muscle movements and coordinate changes in posture as normal, leading to tremor, incoordination, and slowed, reduced movement (bradykinesia) (Blandini, et al., *Mol. Neurobiol.* 1996, 12, 73-94).

The efficacy of compounds of Formula (I) or Formula (II) for treating Parkinson's disease may be assessed using animal and human models of Parkinson's disease and in clinical studies.

Alzheimer's Disease

Alzheimer's disease is a progressive loss of mental function characterized by degeneration of brain tissue, including loss of nerve cells and the development of senile plaques and neurofibrillary tangles. In Alzheimer's disease, parts of the brain degenerate, destroying nerve cells and reducing the responsiveness of the maintaining neurons to neurotransmitters. Abnormalities in brain tissue consist of senile or neuritic plaques, e.g., clumps of dead nerve cells containing an abnormal, insoluble protein called amyloid, and neurofibrillary tangles, twisted strands of insoluble proteins in the nerve cell.

The efficacy of compounds of Formula (I) or Formula (II) for treating Alzheimer's disease may be assessed using animal and human models of Alzheimer's disease and in clinical studies.

Huntington's Disease

Huntington's disease is an autosomal dominant neurodegenerative disorder in which specific cell death occurs in the neostriatum and cortex (Martin, *N Engl J Med* 1999, 340, 1970-80). Onset usually occurs during the fourth or fifth decade of life, with a mean survival at age of onset of 14 to 20 years. Huntington's disease is universally fatal, and there is no effective treatment. Symptoms include a characteristic movement disorder (Huntington's chorea), cognitive dysfunction, and psychiatric symptoms. The disease is caused by a mutation encoding an abnormal expansion of CAG-encoded polyglutamine repeats in the protein, huntingtin.

The efficacy of compounds of Formula (I) or Formula (II) for treating Huntington's disease may be assessed using animal and human models of Huntington's disease and in clinical studies.

Amyotrophic Lateral Sclerosis

Amyotrophic lateral sclerosis (ALS) is a progressive neurodegenerative disorder characterized by the progressive and specific loss of motor neurons in the brain, brain stem, and spinal cord (Rowland and Schneider, *N Engl J Med* 2001, 344, 1688-1700). ALS begins with weakness, often in the hands and less frequently in the feet that generally progresses up an arm or leg. Over time, weakness increases and spasticity develops characterized by muscle twitching and tightening, followed by muscle spasms and possibly tremors. The average age of onset is 55 years, and the average life expectancy after the clinical onset is 4 years. The only recognized treatment for ALS is riluzole, which can extend survival by only about three months.

The efficacy compounds of Formula (I) or Formula (II) for treating ALS may be assessed using animal and human models of ALS and in clinical studies.

Others

Other diseases and conditions for which compounds of Formula (I) or Formula (II) can be useful in treating include rheumatica, granuloma annulare, lupus, autoimmune carditis, eczema, sarcoidosis, and autoimmune diseases including acute disseminated encephalomyelitis, Addison's disease, alopecia greata, ankylosing spondylitis, antiphospholipid antibody syndrome, autoimmune hemolytic anemia, autoimmune hepatitis, autoimmune inner ear disease, bullous pemphigoid, Bechet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anemia, psoriasis, psoriatic arthritis, polymyositis, primary biliary cirrhosis, rheumatoid arthritis, schizophrenia, scleroderma, Sjogren's syndrome, stiff person syndrome, temporal arteritis, ulcerative colitis, vasculitis, vitiligo, acute disseminated encephalomyelitis, myasthenia gravis, and Wegener's granulomatosis.

Administration

Compounds of Formula (I) or Formula (II) and pharmaceutical compositions thereof may be administered orally or by any other appropriate route, for example, by infusion or bolus injection, by absorption through epithelial or mucocutaneous linings (e.g., oral mucosa, rectal, and intestinal mucosa, etc.). Other suitable routes of administration include, for example, intradermal, intramuscular, intraperitoneal, intravenous, subcutaneous, intranasal, epidural, oral, sublingual, intracerebral, intravaginal, transdermal, rectal, inhalation, or topical.

Administration may be systemic or local. Various delivery systems are known, e.g., encapsulation in liposomes, microparticles, microcapsules, capsules, etc., that may be used to administer a compound and/or pharmaceutical composition.

The amount of a compound of Formula (I) or Formula (II) that will be effective in the treatment of a disease in a patient will depend, in part, on the nature of the condition and can be determined by standard clinical techniques known in the art. In addition, in vitro or in vivo assays may be employed to help identify optimal dosage ranges. A therapeutically effective amount of a compound of Formula (I) or Formula (II) to be administered may also depend on, among other factors, the subject being treated, the weight of the subject, the severity of the disease, the manner of administration, and the judgment of the prescribing physician.

For systemic administration, a therapeutically effective dose may be estimated initially from in vitro assays. For example, a dose may be formulated in animal models to achieve a beneficial circulating composition concentration range. Initial doses may also be estimated from in vivo data, e.g., animal models, using techniques that are known in the art. Such information may be used to more accurately determine useful doses in humans. One having ordinary skill in the art may optimize administration to humans based on animal data.

A dose may be administered in a single dosage form or in multiple dosage forms. When multiple dosage forms are used the amount of compound contained within each dosage form may be the same or different. The amount of a compound of Formula (I) or Formula (II) contained in a dose may depend on the route of administration and whether the disease in a patient is effectively treated by acute, chronic, or a combination of acute and chronic administration.

In certain embodiments an administered dose is less than a toxic dose. Toxicity of the compositions described herein may be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. In certain embodiments, a compound or metabolite thereof may exhibit a high therapeutic index. The data obtained from these cell culture assays and animal studies may be used in formulating a dosage range that is not toxic for use in humans. A dose of a compound of Formula (I) or Formula (II) may be within a range of circulating concentrations in for example the blood, plasma, or central nervous system, that include the effective dose and that exhibits little or no toxicity. A dose may vary within this range depending upon the dosage form employed and the route of administration utilized. In certain embodiments, an escalating dose may be administered.

Combination Therapy

Methods provided by the present disclosure further comprise administering one or more pharmaceutically active compounds in addition to a morpholinoalkyl fumarate of Formula (I) or Formula (II). Such compounds may be provided to treat the same disease or a different disease than the disease being treated with the compound of Formula (I) or Formula (II).

In certain embodiments, a compound of Formula (I) or Formula (II) may be used in combination with at least one other therapeutic agent. In certain embodiments, a compound of Formula (I) or Formula (II) may be administered to a patient together with another compound for treating diseases and conditions involving immunological, autoimmune, and/or inflammatory processes including: multiple sclerosis, psoriasis, irritable bowel disorder, ulcerative colitis, arthritis, chronic obstructive pulmonary disease, asthma, Parkinson's disease, Huntington's disease, amyotrophic lateral sclerosis, and others. In certain embodiments, a compound of Formula (I) or Formula (II) may be administered to a patient together with another compound for treating multiple sclerosis, psoriasis, irritable bowel disorder, ulcerative colitis, arthritis, chronic obstructive pulmonary disease, asthma, Parkinson's disease, Huntington's disease, or amyotrophic lateral sclerosis.

A compound of Formula (I) or Formula (II) and the at least one other therapeutic agent may act additively or, in certain embodiments, synergistically. The at least one additional therapeutic agent may be included in the same dosage form as a compound of Formula (I) or Formula (II) or may be provided in a separate dosage form. Methods provided by the present disclosure can further include, in addition to administering a compound of Formula (I) or Formula (II), administering one or more therapeutic agents effective for treating the same or different disease than the disease being treated by a compound of Formula (I) or Formula (II). Methods provided by the present disclosure include administration of a compound of Formula (I) or Formula (II) and one or more other therapeutic agents provided that the combined administration does not inhibit the therapeutic efficacy of the compound of Formula (I) or Formula (II), or any pharmacologically active metabolite thereof, and/or does not typically produce significant and/or substantial adverse combination effects.

In certain embodiments, dosage forms comprising a compound of Formula (I) or Formula (II) may be administered concurrently with the administration of another therapeutic agent, which may be part of the same dosage form as, or in a different dosage form than, that comprising a compound of Formula (I) or Formula (II). A compound of Formula (I) or Formula (II) may be administered prior to, or subsequent to, administration of another therapeutic agent. In certain embodiments, the combination therapy may comprise alternating between administering a compound of Formula (I) or Formula (II) and administering another therapeutic agent, e.g., to minimize adverse drug effects associated with a particular drug. When a compound of Formula (I) or Formula (II) is administered concurrently with another therapeutic agent that potentially may produce an adverse drug effect including, for example, toxicity, the other therapeutic agent may be administered at a dose that falls below the threshold at which the adverse drug effect is elicited.

In certain embodiments, dosage forms comprising a compound of Formula (I) or Formula (II) may be administered with one or more substances to enhance, modulate and/or control release, bioavailability, therapeutic efficacy, therapeutic potency, stability, and the like of a compound of Formula (I) or Formula (II). For example, to enhance the therapeutic efficacy of a compound of Formula (I) or Formula (II), the compound of Formula (I) or Formula (II) may be co-administered with, or a dosage form comprising a compound of Formula (I) or Formula (II) may comprise, one or more active agents to increase the absorption or diffusion of a compound of Formula (I) or Formula (II) from the gastrointestinal tract to the systemic circulation, or to inhibit degradation of the compound of Formula (I) or Formula (II) in the blood of a patient. In certain embodiments, a compound of Formula (I) or Formula (II) may be co-administered with an active agent having pharmacological effects that enhance the therapeutic efficacy of a compound of Formula (I) or Formula (II).

In certain embodiments, a compound of Formula (I), a compound of Formula (II), or a pharmaceutical composition thereof may be administered to a patient for treating psoriasis in combination with a therapy or another therapeutic agent known or believed to be effective in treating psoriasis. Drugs useful for treating psoriasis include, for example, steroids such as flurandrenolide, fluocinonide, alclometasone, amcinonide, desonide, halcinonide, triamcinolone, clobetasol, clocortolone, mometasone, desoximetasone, and halobetasol; anti-rheumatics such as etanercept, infiximab, and adalimumab; immunosuppressive agents such as cyclosporine, alefacept, and efalizumab; psoralens such as methoxsalen; and other such as calcipotriene, methotrexate, hydrocortisone/pramoxine, acitretin, betamethasone/calcipotriene, tazaraotene, benzocaine/pyrilamine/zinc oxide, and ustekinumab.

In certain embodiments, a compound of Formula (I), a compound of Formula (II), or a pharmaceutical composition thereof may be administered to a patient for treating inflammatory arthritis such as rheumatoid arthritis, juvenile rheumatoid arthritis, psoriatic arthritis, and ankylosing spondylitis in combination with a therapy or another therapeutic agent known or believed to be effective in treating inflammatory arthritis such as rheumatoid arthritis, juvenile rheumatoid arthritis, psoriatic arthritis, and ankylosing spondylitis.

Drugs useful for treating rheumatoid arthritis include, for example, non-steroidal anti-inflammatory agents such as ibuprofen, ketoprofen, salicylate, diclofenac, nabumetone, naproxen, meloxicam, sulindac, flurbiprofen, indomethacin, tolmetin, piroxicam, fenoprofen, oxaprozin, and etodolac; antiheumatics such as entanercept, adalimumab, infliximab, hydroxychloroquine, leflunomide, azathioprine, penicillamine, methotrexate, anakinra, auranofin, rituximab, aurothioglucose, tocilizumab, and golimumab; COX-2 inhibitors such as celecoxib and vadecoxib; corticosteroids such as triamcinolone; glucocorticoids such as methylprednisolone and prednisone; and others such as sulfasalazine.

Drugs useful for treating juvenile rheumatoid arthritis include, for example, adalimumab, abatacept, and infliximab.

Drugs useful for treating psoriatic arthritis include, for example, etanercept, adalimumab, triamcinolone, cortisone, infliximab, and golimumab.

Drugs useful for treating ankylosing spondylitis include, for example, adalimumab, celecoxib, diclofenac, etanercept, golimumab, indomethacin infliximab, naptoxen, olsalazine, salicylates, sulfindac, and triamcinolone.

In certain embodiments, a compound of Formula (I), a compound of Formula (II), or a pharmaceutical composition thereof may be administered to a patient for treating psoriatic arthritis in combination with a therapy or another therapeutic agent known or believed to be effective in treating psioriatic arthritis. Drugs useful for treating psioriatic arthritis include, for example, etanercept, adalimumab, triamcinolone, cortisone, infliximab, and golimumab.

In certain embodiments, a compound of Formula (I), a compound of Formula (II), or a pharmaceutical composition thereof may be administered to a patient for treating autoimmune diseases such as lupus in combination with a therapy or another therapeutic agent known or believed to be effective in treating autoimmune diseases such as lupus. Drugs useful for treating lupus include, for example, hydroxychloroquine, triamcinolone, salicylate, azathioprine, and abetimus.

In certain embodiments, a compound of Formula (I), a compound of Formula (II), or a pharmaceutical composition thereof may be administered to a patient for treating multiple sclerosis in combination with a therapy or another therapeutic agent known or believed to be effective in treating multiple sclerosis. Drugs useful for treating multiple sclerosis include, for example, interferon $\beta$-1a, interferon $\beta$-1b, glatiramer, modafinil, azathioprine, prednisolone, mycophenolate mofetil, mitoxantrone, and natalizumab. Other examples of drugs useful for treating MS include, for example, corticosteroids such as methylprednisolone; IFN-$\beta$ such as IFN-$\beta$1a and IFN-$\beta$1b; glatiramer acetate; monoclonal antibodies that bind to the very late antigen-4 (VLA-4) integrin such as natalizumab; immunomodulatory agents such as FTY 720 sphinogosie-1 phosphate modulator and COX-2 inhibitors such as BW755c, piroxicam, and phenidone; and neuroprotective treatments including inhibitors of glutamate excitotoxicity and iNOS, free-radical scavengers, and cationic channel blockers; memantine; AMPA antagonists such as topiramate; and glycine-site NMDA antagonists.

In certain embodiments, a compound of Formula (I), a compound of Formula (II), or a pharmaceutical composition thereof may be administered to a patient for treating inflammatory bowel disease in combination with a therapy or another therapeutic agent known or believed to be effective in treating inflammatory bowel disease. Drugs useful for treating inflammatory bowel disease include, for example, cromolyn and mercaptopurine; and more particularly for treating Crohn's disease include certolizumab, budesonide, azathioprine, sulfasalazine, metronidazole, adalimumab, mercaptopurine, infliximab, mesalamine, and natalizumab; and for treating ulcerative colitis include balsalazide, infliximab, azathioprine, mesalamine, and cyclosporine.

In certain embodiments, a compound of Formula (I), a compound of Formula (II), or a pharmaceutical composition thereof may be administered to a patient for treating irritable bowel syndrome in combination with a therapy or another therapeutic agent known or believed to be effective in treating irritable bowel syndrome. Drugs useful for treating irritable bowel syndrome include, for example, lactobacillus acidophilus, dicylmine, atropine, hyoscyamine, phenobarbital, scopolamine, venlafaxine, chloridazepoxide, clidinium, alosetron, psyllium, cholestyramine, rifaximin, and tegaserod.

In certain embodiments, compounds of Formula (I) or Formula (II) and pharmaceutical compositions thereof may be administered to a patient for treating asthma in combination with a therapy or another therapeutic agent known or believed to be effective in treating asthma, or in certain embodiments, a disease, disorder, or condition associated with asthma. Examples of drugs useful in treating asthma include, for example, albuterol, aminophylline, beclomethasone, bitolterol, budesonide, cromolyn, ephedrine, epinephrine, flunisolide, fluticasone, formoterol, hydrocortisone, isoproterenol, levalbuterol, methylprednisolone, prednisolone, prednisone, pirbuterol, metaproterenol, racepinephrine, omalizumab, oxytriphylline, mometusone, montelukast, nedocromil, oxtriphylline, pirbuterol, salmeterol, terbutaline, theophylline, triamcinolone, zafirlukast, and zileuton.

In certain embodiments, compounds of Formula (I) or Formula (II) and pharmaceutical compositions thereof may be administered to a patient for treating chronic obstructive pulmonary disease in combination with a therapy or another therapeutic agent known or believed to be effective in treating chronic obstructive pulmonary disease, or in certain embodiments, a disease, disorder, or condition associated with chronic obstructive pulmonary disease. Examples of drugs useful for treating chronic obstructive pulmonary disease include, for example, albuterol, arformoterol, azithromycin, bitolterol, epinephrine, fluticasone, formoterol, ipratropium, isoproterenol, levabuterol, metaproterenol, pirbuterol, racepinephrine, salmeterol, and tiotropium. Useful drugs for treating chronic obstructive pulmonary disease further include, for example, bronchodialators such as β2 agonists such as salbutamol, bambuterol, clenbuterol, fenoterol, and formoterol; M3 antimuscarinics such as ipratropium; leukotriene antagonists such as montelukast, pranlukast, and zafirlukast; cromones such as cromoglicate and nedocromil; xanthines such as theophylline; corticosteroids such as beclomethasone, mometasone, and fluticasone; and TNF antagonists such as infliximab, adalimumab, and etanercept. Other treatments for chronic obstructive pulmonary disease include oxygen therapy, and pulmonary rehabilitation.

In certain embodiments, compounds of Formula (I) or Formula (II) and pharmaceutical compositions thereof may be administered to a patient for treating angiogenesis in combination with a therapy or another therapeutic agent known or believed to be effective in treating angiogenesis. Useful drugs for treating angiogenesis include, for example, angiostatin, endostatin, vitaxin, bevacizumab, thalidomide, batimastat, marimastat, carboxyamidotraizole, TNP-470, CM101, IFN-α, IL-12, platelet factor-4, suramin, SU5416, thrombospondin, VEGFR, angiostatic steroids, cartilage-derived angiogenesis inhibitory factor, matrix metalloproteinase inhibitors, 2-methoxyestradiol, tecogalan, thrombospondin, prolactin, $\alpha_v\beta_3$ inhibitors, and linomide.

In certain embodiments, compounds of Formula (I) or Formula (II) and pharmaceutical compositions thereof may be administered to a patient for treating transplant rejection in combination with a therapy or another therapeutic agent known or believed to be effective in treating transplant rejection. Useful drugs for treating transplant rejection include, for example, calcineurin inhibitors such as cyclosporine and tacrolimus, mTOR inhibitors such as sirolimus and everolimus, anti-proliferatives such as azathioprine and mycophenolic acid; monoclonal anti-IL2Rα receptor antibodies including basiliximab and daclizumab; and polyclonal anti-T-cell antibodies including anti-thymocyte globulin and anti-lymphocyte globulin.

In certain embodiments, compounds of Formula (I) or Formula (II) and pharmaceutical compositions thereof may be administered to a patient for treating transplantation rejection in combination with a therapy or another therapeutic agent known or believed to be effective in treating transplantation rejection. Examples of drugs useful in transplantation rejection include, for example, corticosteroids such as dexamethasone, prednisolone, and prednisone; globulins such as anti-lymphocyte globulin and antithymocyte globulin; macrolide immunosuppressants such as sirolimus, tacrolimus, and everolimus; mitotic inhibitors such as azathiprine, cylophosphamide, and methotrexate; monoclonal antibodies such as basiliximab, daclizumab, infliximab, muromonoab; fungal metabolites such as cyclosporine; and others such as glatiramer and mycophenolate.

In certain embodiments, compounds of Formula (I) or Formula (II) and pharmaceutical compositions thereof may be administered to a patient for treating cardiac insufficiency in combination with a therapy or another therapeutic agent known or believed to be effective in treating cardiac insufficiency. Useful drugs for treating cardiac insufficiency include, for example, antitensin-modulating agents, diuretics such as furosemide, bumetanie, hydrochlorothiazide, chlorthalidone, chlorthiazide, spironolactone, eplerenone: beta blockers such as bisoprolol, carvedilol, and metroprolol; positive inotropes such as digoxin, milrinone, and dobutamine; alternative vasodilators such as isosorbide dinitrate/hydralazine; aldosterone receptor antagonists; recombinant neuroendocrine hormones such as nesiritide; and vasopressin receptor antagonists such as tolvaptan and conivaptan.

In certain embodiments, compounds of Formula (I) or Formula (II) and pharmaceutical compositions thereof may be administered to a patient for treating a mitochondrial disease such as a neurodegenerative disease in combination with a therapy or another therapeutic agent known or believed to be effective in treating a mitochondrial disease such as a neurodegenerative disease. In certain embodiments, a neurodegenerative disease is chosen from Alzheimer's disease, Parkinson's disease, Huntington's disease, and amyotrophic lateral sclerosis.

Therapeutic agents useful for treating Parkinson's disease include, for example, dopamine precursors such levodopa, dopamine agonists such as bromocriptine, pergolide, pramipexole, and ropinirole, MAO-B inhibitors such as selegiline, anticholinergic drugs such as benztropine, trihexyphenidyl, tricyclic antidepressants such as amitriptyline, amoxapine, clomipramine, desipramine, doxepin, imipramine, maprotiline, nortriptyline, protriptyline, amantadine, and trimipramine, some antihistamines such as diphenhydramine; antiviral drugs such as amantadine; and beta blockers such as propranolol.

Useful drugs for treating Alzheimer's disease include, for example, roloxifene, vitamin E, donepezil, tacrine, rivastigmine, galantamine, and memantine.

Useful drugs for treating symptoms of Huntington's disease include, for example, antipsychotics such as haloperidol, chlorpromazine and olanzapine to control hallucinations, delusions and violent outbursts; antidepressants such as fluoxetine, sertraline, and nortriptyline to control depression and obsessive-compulsive behavior; tranquilizers such as benzodiazepines, paroxetine, venflaxin and beta-blockers to control anxiety and chorea; mood stabilizers such as lithium, valproate, and carbamzepine to control mania and bipolar disorder; and botulinum toxin to control dystonia and jaw clenching. Useful drugs for treating symptoms of Huntington's disease further include selective serotonin reuptake inhibitors (SSRIs) such as fluoxetine, paroxetine, sertraline, escitalopram, citalopram, fluvosamine; norepinephrine; serotonin reuptake inhibitors (NSRI) such as venlafaxine and duloxetine; benzodiazepines such as clonazepam, alprazolam, diazepam, and lorazepam; tricyclic antidepressants such as amitriptyline, nortriptyline, and imipramine; atypical antidepressants such as busipirone, bupriopion, and mirtazepine for treating the symptoms of anxiety and depression; atomoxetine, dextroamphetamine, and modafinil for treating apathy symptoms; amantadine, memantine, and tetrabenazine for treating chorea symptoms; citalopram, atomoxetine, memantine, rivastigmine, and donepezil for treating cognitive symptoms; lorazepam and trazedone for treating insomnia; valproate, carbamazepine and lamotrigine for treating symptoms of irritability; SSRI antidepressants such as fluoxetine, paroxetine, sertaline, and fluvoxamine; NSRI antidepressants such as venlafaxine; others such as mirtazepine, clomipramine, lomotrigine, gabapentin, valproate, carbamazepine, olanzapine, rispiridone, and quetiapine for treating symptoms of obsessive-compulsive disorder; haloperidol, quetiapine, clozapine, risperidone, olanzapine, ziprasidone, and aripiprazole for treating psychosis; and pramipexole, levodopa and amantadine for treating rigidity.

Useful drugs for treating ALS include, for example, rilu-zole. Other drugs of potential use in treating ALS include, for example, memantine, tamoxifen, thalidomide, ceftriaxone, sodium phenyl butyrate, celecoxib, glatiramer acetate, busipirone, creatine, minocycline, coenzyme Q10, oxandrolone, IGF-1, topiramate, xaliproden, and indinavir. Drugs such as baclofen and diazepam can be useful in treating spasticity associated with ALS.

In certain embodiments, a compound of Formula (I), a compound of Formula (II), or a pharmaceutical composition thereof may be administered to a patient in combination with a therapy or another therapeutic agent known or believed to be effective in inhibiting TNF function.

Examples of drugs known to inhibit TNF function include, for example, infliximab, adalimumab, etanercept, certolizumab, goliimumab, pentoxifylline, quanylhydrozone, thalidomide, flavonoids such as narigenin, resveratol and quecetin, alkaloids such as lycorine, terpenes such as acanthoic acid, fatty acids such as 13-HOA, and retinoids such as retinoic acid.

EXAMPLES

The following examples describe in detail the synthesis of morpholinoalkyl fumarates of Formula (I) or Formula (II), properties of compounds of Formula (I) or Formula (II), and uses of compounds of Formula (I) or Formula (II). It will be apparent to those skilled in the art that many modifications, both to materials and methods, may be practiced without departing from the scope of the disclosure.

General Experimental Protocols

All reagents and solvents that are purchased from commercial suppliers are used without further purification or manipulation procedures.

Proton NMR (400 MHz) and carbon NMR spectra (125 MHz) are recorded on a Varian AS 400 NMR spectrometer equipped with an autosampler and data processing software. $CDCl_3$ (99.8% D), DMSO-$d^6$ (99.9% D), or MeOH-$d^4$ (99.8+% D), and acetonitrile-$d^3$ are used as solvents unless otherwise noted. The $CHCl_3$, DMSO-$d^5$, or MeOH-$d^3$ solvent signals are used for calibration of the individual spectra. Analytical thin layer chromatography (TLC) is performed using a Whatman, Schleicher & Schuell TLC and MK6F silica gel plates (2.5×7.5 cm, 250 μm layer thickness). Melting points are recorded in glass capillaries using a Stanford Research Systems (SRS) Optimelt Automated Melting Point System, S/N 78047. Analytical LC/MS is performed on a Waters 2790 separation module equipped with a Waters Micromass QZ mass spectrometer, a Waters 996 photodiode detector, and a Merck Chromolith UM2072-027 or Phenomenex Luna C-18 analytical column. Mass-guided preparative HPLC purification of final compounds is performed using an instrument equipped with a Waters 600 controller, ZMD Micromass spectrometer, a Waters 2996 photodiode array detector, and a Waters 2700 Sample Manager. Acetonitrile/water gradients containing 0.05% formic acid are used as eluents in both analytical and preparative HPLC experiments. Compound isolation from aqueous solvent mixtures, e.g., acetonitrile/water/0.05% formic acid, is accomplished by primary lyophilization (freeze drying) of the frozen solutions under reduced pressure at room temperature using manifold freeze dryers such as a Heto Drywinner DW 6-85-1, a Heto FD4, or a VIRTIS Freezemobile 25 ES equipped with high vacuum pumps. When the isolated compound has ionizable functional groups such as an amino group or a carboxylic acid, lyophilization is performed in the presence of a slight excess of one molar (1 M) hydrochloric acid to yield the purified compounds as the corresponding hydrochloride salts (HCl-salts) or the corresponding protonated free carboxylic acids. When the isolated compound has ionizable functional groups such as a carboxylic acid, lyophilization is performed in the presence of equimolar amounts of sodium hydrogen carbonate ($NaHCO_3$) to yield the purified compounds as the corresponding sodium salts (Na-salts). Optionally, the isolated materials are further purified by flush silica gel column chromatography, optionally employing Biotage pre-packed silica gel cartridges. Suitable organic solvents such as ethyl acetate (EtOAc), hexane (Hxn), n-heptane (Hptn), or mixtures and/or gradients thereof are used as eluents to yield the target compounds as colorless, viscous oils or solids after evaporation of the solvents. Chemical names are generated with the Chemistry 4-D Draw Pro Version 7.01c (Draw Chemical Structures Intelligently© 1993-2002) from ChemInnovation Software, Inc., San Diego, USA).

Non-commercially available starting materials are synthesized from commercially available starting materials, and by adapting methods well known in the art.

General Procedure A

Nucleophilic Substitution of 1-Haloalkylmorpholine Derivatives with Monoalkyl Fumarate (2E)-3-(Alkoxycarbonyl)prop-2-enoic acid (alkyl hydrogen fumarate), (2E)-3-(tert-butoxycarbonyl)prop-2-enoic acid (tert-butyl hydrogen fumarate), or fumaric acid (FA) (1.0 equivalents) is dissolved in 5-10 mL/3.0 mmol of an inert solvent such as N-methylpyrrolidone (NMP), N,N-dimethylformamide, N,N-dimethylacetamide (DMA, DMAc), acetonitrile (MeCN), dimethylsulfoxide (DMSO), tetrahydrofuran (THF), toluene, or mixtures thereof. To the solution, 0.8 to 1.2 equivalents of an appropriate inorganic base such as cesium hydrogen carbonate (CsHCO$_3$), cesium carbonate (Cs$_2$CO$_3$), or potassium carbonate (K$_2$CO$_3$) is added. Alternatively, 0.8 to 1.2 equivalents of a silver salt such silver(I) oxide (Ag$_2$O) or silver(I) carbonate (Ag$_2$CO$_3$); an organic secondary or tertiary base such as dicyclohexylamine (DCHA), triethylamine (TEA), diisopropylethylamine (DIEA), tetrabutylammonium hydroxide (TBAOH), amidine; or a guanidine-based base such as 1,5-diazabicyclo[4.3.0]non-5-ene (DBN), 1,8-diazabicyclo[5.4.0]undec-7-ene (DBU), or 1,1,3,3-tetramethylguanidine (TMG), can be employed. The corresponding alkali, silver, di-, tri- and tetraalkylammonium, amidine, or guanide salt of monoalkyl fumarate can also be pre-formed. The solution is stirred for 10-60 min at room temperature followed by addition of 0.8 to 1.2 equivalents of an appropriately functionalized 1-halo alkylmorpholine. The reaction mixture is stirred overnight at a temperature between 40° C. to 100° C. After cooling to room temperature, insolubles can optionally be filtered off and the reaction mixture diluted with water and an appropriate organic solvent such as methyl tert-butyl ether (MTBE), diethyl ether (Et$_2$O), ethylacetate (EtOAc), or mixtures thereof. After phase separation, the aqueous phase is extracted several times with the same solvent. The combined organic extracts are washed with water, brine, and dried over anhydrous magnesium sulfate (MgSO$_4$). After filtration, the organic solvents are removed under reduced pressure using a rotary evaporator. If required, the crude reaction products are further purified by well-known purification techniques such as silica gel flash column chromatography (i.e., Biotage), mass-guided reversed-phase preparative HPLC/lyophilization, precipitation, or crystallization.

General Procedure B1

Activation of Carboxylic Acid Derivatives with Dehydration Agents for Aminolysis or Alcoholysis A monoalkyl fumarate (1.0 equivalents) is reacted at temperature from ca. 0° C. (ice bath) to room temperature with 1.0-1.5 equivalents of a carbodiimide dehydration agent such as 1-ethyl-3-(3-dimethylaminopropyl)carbodiimide (EDAC, EDC), N,N'-diisopropylcarbodiimide (DIC), N,N'-dicyclohexylcarbodiimide (DCC) in an inert solvent such as dichloromethane (DCM), N,N-dimethylformamide, N-methylpyrrolidone (NMP), or N,N-dimethylacetamide (DMA, DMAc) (ca. 3 mL/mmol). 1.0-1.5 equivalents of 1-hydroxyalkyl morpholine dissolved in the same solvent and, optionally, in the presence of a catalytic or stoichiometric amount of 4-(N,N-dimethylaminopyridine) (DMAP) is added at a temperature from ca. 0° C. to room temperature. When the amine is a salt form, an equimolar amount of an organic tertiary base, such as triethylamine (TEA), or diisopropylethylamine (DIEA) may be added to free the amine base prior to the coupling step. The reaction mixture is stirred for 4 to 12 hours at room temperature. Optionally, the organic solvents are removed under reduced pressure using a rotary evaporator and the residue diluted with an appropriate extraction solvent such as diethyl ether (Et$_2$O), methyl tert-butyl ether (MTBE), ethyl acetate (EtOAc), or others. The procedures described in Procedure A for product isolation and purification may be employed.

General Procedure B2

Activation of Carboxylic Acid Derivatives with Chlorination Agents and Aminolysis A monoalkyl fumarate (1.0 equivalents) is reacted with oxalyl chloride (1.0-1.5 equivalents) in anhydrous dichloromethane (DCM), ca. 3 mL/mmol, at a temperature of ca. 0° C. (ice bath) in the presence of a catalytic amount of N,N-dimethylformamide for 1 to 3 hours. The solvents are removed under reduced pressure using a rotary evaporator and the crude material is dissolved in anhydrous dichloromethane (DCM), ca. 3 mL/mmol. 1.0 to 1.5 equivalents of a 1-hydroxyalkyl morpholine in anhydrous dichloromethane (DCM), ca. 3 mL/mmol, is added drop-wise at ca. 0° C. (ice bath), optionally in the presence of a catalytic amount of 4-(N,N-dimethylamino)pyridine (DMAP). When the 1-hydroxyalkyl morpholine is a salt form, an equimolar amount of a base such as triethylamine (TEA), diisopropylethylamine (DIEA), or others, is added prior to the coupling step. The reaction is stirred overnight with warming to room temperature, the solvents optionally removed under reduced pressure using a rotary evaporator, and then diluted with an appropriate extraction solvent such as diethyl ether (Et$_2$O), methyl tert-butyl ether (MTBE), ethyl acetate (EtOAc), or others. The procedures described in Procedure A for product isolation and purification may be employed.

General Procedure C

Preparation of Mono-Esters of Fumaric Acid

Coupling Reaction of Morpholin-4-ylalkyl-1-ol with Fumaric Acid

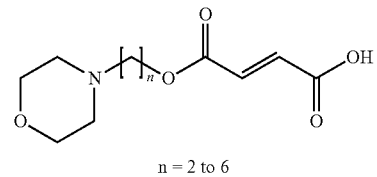

n = 2 to 6

Fumaric acid (1.0 eq.) is dissolved in an inert solvent such as dichloromethane (DCM), N,N-dimethylformamide (DMF), N-methylpyrrolidone (NMP), or N,N-dimethylacetamide (DMA, DMAc) (ca. 3 mL/mmol) and the solution is treated with 1.0-1.5 eq. of a carbodiimide dehydration agent such as 1-ethyl-3-(3-dimethylaminopropyl)-carbodiimide (EDAC, EDC), N,N-diisopropylcarbodiimide (DIC), N,N-dicyclohexyl-carbodiimide (DCC) at a temperature from ca. 0° C. (ice bath) to room temperature. The mixture is then reacted with a solution of an appropriately functionalized of morpholin-4-ylalkyl-1-ol (1.0-1.5 eq.) in the same solvent. Optionally, a catalytic or stoichiometric amount of 4-(N,N-dimethylaminopyridine) (DMAP) is added to the mixture at a temperature from ca. 0.degree. C. to room temperature. When the amine is in a salt form, an equimolar amount of an organic tertiary base, such as triethylamine (TEA), or diisopropylethylamine (DIEA) may be added to free the amine base prior to the coupling step. The reaction mixture is stirred for 4 to 12 hours at room temperature. Optionally the organic solvents are removed under reduced pressure using a rotary evaporator and the residue diluted with an appropriate extraction solvent such as diethyl ether (Et$_2$O), methyl tert-butyl ether (MTBE), ethyl acetate (EtOAc), or others. Water is added to the reaction mixture, the aqueous phase was acidified using 1N hydrochloric acid until aqueous pH reaches to pH ~2. After phase separation, the aqueous phase is extracted several times with the same solvent. The combined organic extracts are washed with water, brine, and dried over anhydrous magnesium sulfate (MgSO$_4$). After filtration, the organic solvents are removed under reduced pressure using a rotary evaporator. If required, the crude reaction products are further purified by well-known purification techniques such as silica gel flash column chromatography (i.e., Biotage), mass-guided reversed-phase preparative HPLC/lyophilization, precipitation, or crystallization to yield the pure desired product.

General Procedure D

Preparation of Bis-Esters

Coupling Reaction of Morpholin-4-ylalkyl-1-ol with Fumaric Acid

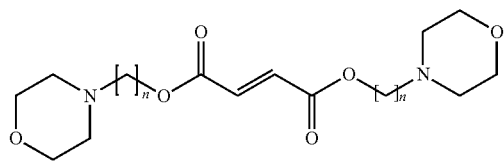

n = 2 to 6

Fumaric acid (1.0 eq.) is dissolved in an inert solvent such as dichloromethane (DCM), N,N-dimethylformamide (DMF), N-methylpyrrolidone (NMP), or N,N-dimethylacetamide (DMA, DMAc) (ca. 3 mL/mmol) and the solution is reacted with 2.0-2.5 eq. of a carbodiimide dehydration agent such as 1-ethyl-3-(3-dimethylaminopropyl)-carbodiimide (EDAC, EDC), N,N-diisopropylcarbodiimide (DIC), N,N-dicyclohexyl-carbodiimide (DCC) at a temperature from ca. 0° C. (ice bath) to room temperature. A solution of an appropriately functionalized of morpholin-4-ylalkyl-1-ol (2.0-2.5 eq.) in the same solvent and, optionally, a catalytic or stoichiometric amount of 4-(N,N-dimethylaminopyridine (DMAP) are added to the above mixture at a temperature from ca. 0° C. to room temperature. When the amine is in a salt form, an equimolar amount of an organic tertiary base, such as triethylamine (TEA), or diisopropylethylamine (DIEA) may be added to free up the amine base prior to the coupling step. The reaction mixture is then stirred for 4 to 12 hours at room temperature or until the reaction goes to completion (TLC or HPLC). The organic solvents are removed under reduced pressure using a rotary evaporator and the residue is diluted with an appropriate extraction solvent such as diethyl ether (Et$_2$O), methyl tert-butyl ether (MTBE), ethyl acetate (EtOAc), or others. After phase separation, the aqueous phase is extracted several times with the same solvent. The combined organic extracts are washed with water, brine, and dried over anhydrous magnesium sulfate (MgSO$_4$). After filtration, the organic solvents are removed under reduced pressure using a rotary evaporator. If required, the crude reaction product is further purified by well-known purification techniques such as silica gel flash column chromatography (i.e., Biotage), mass-guided reversed-phase preparative HPLC/lyophilization, precipitation, or crystallization to give the pure bis ester.

Example 1

Methyl(2-morpholinoethyl)fumarate (Methyl 2-morpholin-4ylethyl(2E)but-2-ene-1,4-dioate) (1)

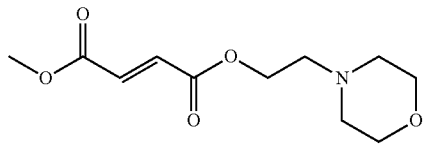 [SMILES: COC(=O)/C=C/C(=O)OCCN1CCOCC1]

Following general Procedure A, methyl hydrogen fumarate (MHF) (26 g, 0.2 mol) was activated with 1-ethyl-3-(3-dimethylaminopropyl)carbodiimide hydrochloride (EDAC) (47.75 g, 0.25 mol) in 200 nit of dichloromethane (DCM) at ca. 0° C. 2-Morpholin-4-ylethyl-1-ol (26.2 g, 0.2 mol) and 4-N,N-dimethylaminopyridine (DMAP) (1 g, 0.008 mol) were added to the activated carboxylic acid. After synthesis, 38 g (81% yield) of the title compound was isolated as a viscous-oil.

$^1$H NMR (CDCl$_3$, 400 MHz): δ 6.88 (m, 2H), 4.35-4.33 (m, 2H), 3.82 (s, 3H), 3.72-3.70 (m, 4H), 2.699-2.68 (m, 2H), 2.67-2.51 (m, 4H), MS (ESI): m/z 245.11 (M+H)$^+$.

Example 2

Methyl(2-morpholinoethyl)fumarate HCl salt (Methyl 2-morpholin-4-ylethyl(2E)but-2-ene-1,4-dioate HCl salt) (2)

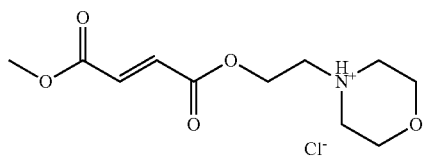

Following general Procedure B, Methyl 2-morpholin-4-ylethyl(2E)but-2-ene-1,4-dioate (38 g, 0.156 mol) was dissolved in methyl tert-butyl ether (200 mL). The resulting clear reaction mixture is cooled to 0° C. (ice bath). 1.1 equivalent of hydrochloride in dioxane (4M) was slowly added over a period of 30 minutes. During this period the product starts to precipitate/crystallize out as off-white solid. The solid product was separated by filtration and the filter-cake was washed with methyl tert-butyl ether (100 mL). The filter-cake was dried under vacuum oven at 40° C. to 38 g (82.5% yield) of the title compound as a white solid.

$^1$H NMR (MeOH-D$_3$, 400 MHz): δ 6.93 (m, 2H), 4.61-4.58 (m, 2H), 3.95-3.89 (broad m, 4H), 3.81 (s, 3H), 3.57-3.55 (m, 2H), 3.31-3.29 (m, 4H), MS (ESI): m/z 245.11 (M+H)$^+$. Melting point: 214.3° C.

Example 3

Methyl(3-morpholinopropyl)fumarate (Methyl 3-morpholin-4-ylpropyl(2E)but-2-ene-1,4-dioate) (3)

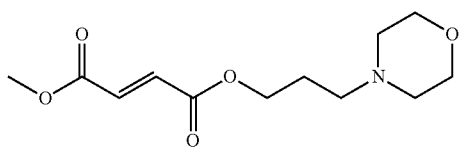 [SMILES: COC(=O)/C=C/C(=O)OCCCN1CCOCC1]

Following general Procedure A, methyl hydrogen fumarate (MEW) (8.9 g, 0.068 mol) was activated with 1-ethyl-3-(3-dimethylaminopropyl)carbodiimide hydrochloride (EDAC) (15.28 g, 0.08 mol) in 200 mL of dichloromethane (DCM) at ca. 0° C. 3-Morpholin-4ylpropyl-1-ol (10 g, 0.068 mol) and 4-N,N-dimethylaminopyridine (DMAP) (500 mg, 0.004 mol) were added to the activated carboxylic acid. After synthesis, 9 g (50.8% yield) of the title compound was afforded as a viscous-oil.

$^1$H NMR (CDCl$_3$, 400 MHz): δ 6.87-6.86 (m, 2H), 4.28-4.26 (m, 2H), 3.82 (s, 3H), 3.72-3.70 (m, 4H), 2.44 (m, 4H), 1.89-1.86 (m, 2H), 1.63 (m, 2H), MS (ESI): m/z 259.13 (M+H)$^+$.

Example 4

Methyl(3-morpholinopropyl)fumarate HCl salt (Methyl 3-morpholin-4ylpropyl(2E)but-2-ene-1,4-dioate HCl salt) (4)

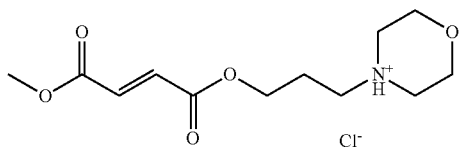

Following general Procedure B, Methyl 3-morpholin-4-ylpropyl(2E)but-2-ene-1,4-dioate (9 g, 0.035 mol) was dissolved in methyl tert-butyl ether (50 mL). The resulting clear reaction mixture is cooled to 0° C. (ice bath). 1.2 equivalent of hydrochloride in dioxane (4M) was slowly added over a period of 30 minutes. During this period the product starts to precipitate/crystallize out as off-white solid. The solid product was separated by filtration and the filter-cake was washed with methyl tert-butyl ether (50 mL). The filter-cake was dried under vacuum oven at 40° C. to 10 g (980 yield) of the title compound as a white solid.

$^1$H NMR (MeOH-D$_3$, 400 MHz): δ 6.88 (m, 2H), 4.34-4.31 (m, 2H), 3.95-3.89 (broad m, 4H), 3.82 (s, 3H), 3.30-3.27 (m, 6H), 3.31-3.29 (m, 2H), MS (ESI): m/z 259.13 (M+H)$^+$. Melting point: 185.2° C.

Example 5

Methyl(4-morpholinobutyl)fumarate (Methyl 4-morpholin-4-ylbutyl(2E)but-2-ene-1,4-dioate) (5)

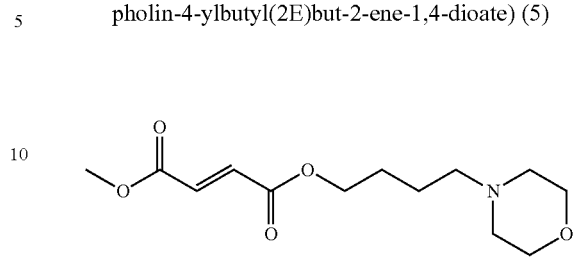

Following general procedure A, methyl hydrogen fumarate (MHF) (26 g, 0.2 mol) was activated with 1-ethyl-3-(3-dimethylaminopropyl)carbodiimide hydrochloride (EDAC) (47.75 g, 0.25 mol) in 200 mL of dichloromethane (DCM) at ca. 0° C. 4-Morpholin-4ylbutyl-1-ol (31.8 g, 0.2 mol) and 4-N,N-dimethylaminopyridine (DMAP) (1 g, 0.008 mol) were added to the activated carboxylic acid. After work-up and isolation, 45 g (83.3% yield) of the title compound was afforded as a viscous-oil.

$^1$H NMR (CDCl$_3$, 400 MHz): δ 6.86-6.86 (m, 2H), 4.24-4.21 (m, 2H), 3.81 (s, 3H), 3.71-3.69 (m, 4H), 2.43-2.34 (m, (H), 1.74-1.69 (m, 2H), 1.60-1.56 (m, 2H), MS (ESI): m/z 272.14 (M+H)$^+$.

Example 6

Methyl(4-morpholinobutyl)fumarate HCl salt (Methyl 4-morpholin-4ylbutyl(2E)but-2-ene-1,4-dioate HCl salt) (6)

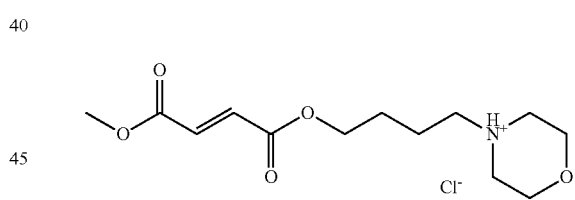

Following general procedure B, Methyl 4-morpholin-4-ylbutyl(2E)but-2-ene-1,4-dioate (45 g, 0.166 mol) was dissolved in methyl tert-butyl ether (200 mL). The resulting clear reaction mixture is cooled to 0° C. (ice bath). 1.0 equivalent of hydrochloride in dioxane (4M) was slowly added over a period of 30 minutes. During this period the product starts to precipitate/crystallize out as off-white solid. The solid product was separated by filtration and the filter-cake was washed with methyl tert-butyl ether (200 mL). The filter-cake was dried under vacuum oven at 40° C. to 38 g (65.0% yield) of the title compound as a white solid.

$^1$H NMR (CDCl$_3$, 400 MHz): δ 6.90-6.82 (m, 2H), 4.34-4.24 (m, 4H), 4.01-3.97 (m, 2H), 3.82 (s, 3H), 3.48-3.45 (m, 2H), 3.06-3.03 (m, 2H), 3.00-2.84 (m, 2H), 2.09-1.81 (m, 2H), 1.79-1.77 (m, 2H) MS (ESI): m/z 272.14 (M+H)$^+$. Melting point: 145.5° C.

Example 7

Methyl(5-morpholinopentyl)fumarate (Methyl 5-morpholin-4-ylpentyl(2E)but-2-ene-1,4-dioate) (7)

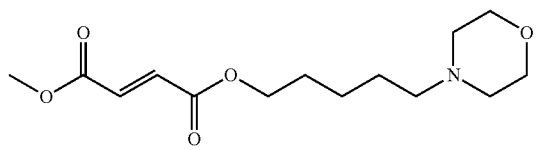 [SMILES: COC(=O)/C=C/C(=O)OCCCCCN1CCOCC1]

Following general procedure A, methyl hydrogen fumarate (MHF) (13.0 g, 0.1 mol) was activated with 1-ethyl-3-(3-dimethylaminopropyl)carbodiimide hydrochloride (EDAC) (22.9 g, 0.12 mol) in 50 mL of dichloromethane (DCM) at ca. 0° C. 5-Morpholin-4ylpentyl-1-ol (17.3 g, 0.1 mot) and 4-N,N-dimethylaminopyridine (DMAP) (100 mg) were added to the activated carboxylic acid. After work-up and isolation, 11 g (28.5% yield) of the title compound was afforded as a viscous-oil.

$^1$H NMR (CDCl$_3$, 400 MHz): δ 6.86 (m, 2H), 4.24-4.21 (m, 2H), 3.81 (s, 3H), 3.71-3.69 (m, 4H), 2.43-2.34 (m, 6H), 1.74-1.69 (m, 2H), 1.60.1.56 (m, 4H), MS (ESI): m/z 287.16 (M+H)$^+$.

Example 8

Methyl(5-morpholinopentyl)fumarate HCl salt (Methyl 5-morpholin-4ylpentyl(2E)but-2-ene-1,4-dioate HCl salt) (8)

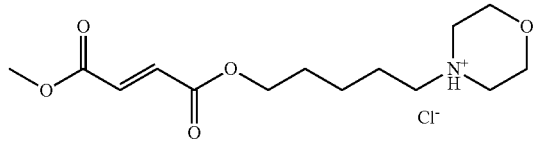

Following general procedure B, Methyl 5-morpholin-4yl-pentyl(2E)but-2-ene-1,4-dioate (11 g, 0.0385 mol) was dissolved in methyl tert-butyl ether (100 mL). The resulting clear reaction mixture is cooled to 0° C. (ice bath). 1.2 equivalent of hydrochloride in dioxane (4M) was slowly added over a period of 30 minutes. During this period the product starts to precipitate/crystallize out as off-white solid. The solid product was separated by filtration and the filter-cake was washed with methyl tert-butyl ether (100 mL). The filter-cake was dried under vacuum oven at 40° C. to 10 g (81.3 yield) of the title compound as a white solid.

$^1$H NMR (MeOH-D$_3$, 400 MHz): δ 6.82-6.81 (m, 2H), 4.26-4.22 (m, 2H), 4.08-4.03 (broad m, 2H), 3.79 (s, 3H), 3.50-3.31 (broad m, 2H), 3.30-3.29 (m, 2H), 3.18-3.14 (m, 4H), 1.85-1.74 (m, 4H), 1.52-1.45 (m. 2H), MS (ESI): m/z 287.16.13 (M+H)$^+$. Melting point: 150.0° C.

Example 9

Methyl(6-morpholinohexyl)fumarate (Methyl 6-morpholin-4-ylhexyl(2E)but-2-ene-1,4-dioate) (9)

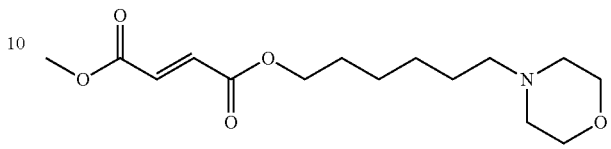

Following general procedure A, methyl hydrogen fumarate (MHF) (2.0 g, 15.3 mmol) was activated with 1-ethyl-3-(3-dimethylaminopropyl)carbodiimide hydrochloride (EDAC) (3.82 g, 20.0 mmol) in 25 mL of dichloromethane (DCM) at ca. 0° C. 6-Morpholin-4ylhexyl-1-ol (3 g, 16.0 mmol) and 4-N,N-dimethylaminopyridine (DMAP) (100 mg) were added to the activated carboxylic acid. After work-up and isolation, 3 g (62.6% yield) of the title compound was afforded as a viscous-oil.

$^1$H NMR (CDCl$_3$, 400 MHz): δ 6.86 (m, 2H), 4.24-4.21 (m, 2H), 3.81 (s, 3H), 3.71-3.69 (m, 4H), 2.43-2.34 (m, 6H), 1.74-1.69 (m, 4H), 1.60.1.56 (m, 4H), MS (ESI): m/z 301.18 (M+H)$^+$.

Example 10

Methyl(6-morpholinohexyl)fumarate HCl salt (Methyl 6-morpholin-4ylhexyl(2E)but-2-ene-1,4-dioate HCl salt) (10)

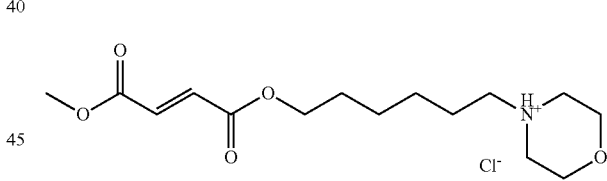

Following general procedure B, Methyl 6-morpholin-4yl-hexyl(2E)but-2-ene-1,4-dioate (3 g, 10 mmol) was dissolved in methyl tert-butyl ether (25 mL). The resulting clear reaction mixture is cooled to 0° C. (ice bath). 1.2 equivalent of Hydrochloride in dioxane (4M) was slowly added over a period of 30 minutes. During this period the product starts to precipitate/crystallize out as off-white solid. The solid product was separated by filtration and the filter-cake was washed with methyl tert-butyl ether (25 mL). The filter-cake was dried under vacuum oven at 40° C. to 3 g (93.75% yield) of the title compound as a white solid.

$^1$H NMR (MeOH-D$_3$, 400 MHz): δ 6.82-6.81 (m, 2H), 4.24-4.20 (m, 2H), 4.23-4.08 (broad m, 2H), 3.79 (s, 3H), 3.55-3.45 (broad m, 2H), 3.31-3.29 (m, 2H), 3.17-3.12 (m, 4H), 1.77-1.72 (m, 4H), 1.47-1.45 (m. 4H), MS (ESI): m/z 301.18 (M+H)$^+$. Melting point: 104.1° C.

Example 11

Ethyl (2-morpholinoethyl)fumarate (11)

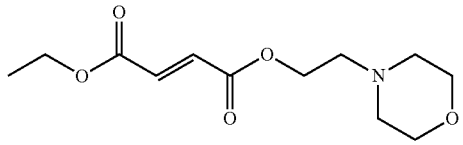 [SMILES: CCOC(=O)/C=C/C(=O)OCCN1CCOCC1]

Following the procedure of Example 1, and replacing methyl hydrogen fumarate with ethyl hydrogen fumarate provides the title compound (11). The reaction of the free base with HCl in dioxane and following the procedure of Example 2 affords the corresponding HCl salt.

Example 12

Propyl (2-morpholinoethyl)fumarate (13)

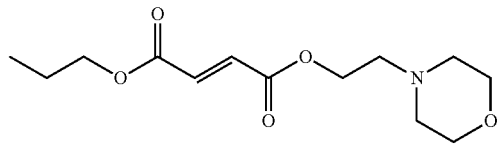 [SMILES: CCCOC(=O)/C=C/C(=O)OCCN1CCOCC1]

Following the procedure of Example 1, and replacing methyl hydrogen fumarate with propyl hydrogen fumarate provides the title compound (13). The reaction of the free base with HCl in dioxane and following the procedure of Example 2 affords the corresponding HCl salt.

Example 13

Butyl (2-morpholinoethyl)fumarate (15)

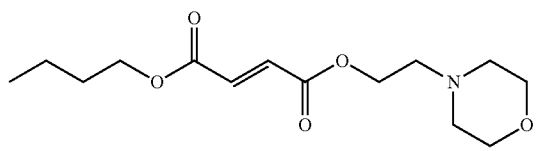 [SMILES: CCCCOC(=O)/C=C/C(=O)OCCN1CCOCC1]

Following the procedure of Example 1, and replacing methyl hydrogen fumarate with propyl hydrogen fumarate provides the title compound (15). The reaction of the free base with HCl in dioxane and following the procedure of Example 2 affords the corresponding HCl salt.

Example 14

Pentyl (2-morpholinoethyl)fumarate (17)

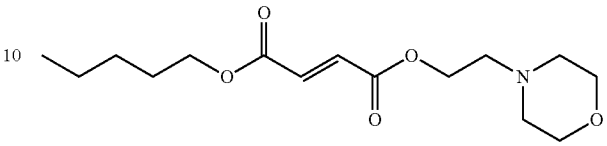

Following the procedure of Example 1, and replacing methyl hydrogen fumarate with pentyl hydrogen fumarate provides the title compound (17). The reaction of the free base with HCl in dioxane and following the procedure of Example 2 affords the corresponding HCl salt.

Example 15

(4-Morpholinobutyl)fumarate (39)

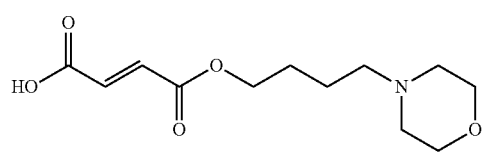 [SMILES: O=C(O)/C=C/C(=O)OCCCCN1CCOCC1]

Following general procedure C, t-butyl hydrogen fumarate (MHF) (0.2 mol) is activated with 1-ethyl-3-(3-dimethylaminopropyl)carbodiimide hydrochloride (EDAC) (47.75 g, 0.25 mol) in 200 mL of dichloromethane (DCM) at ca. 0° C. 4-Morpholin-4ylbutyl-1-ol (31.8 g, 0.2 mol) and 4-N,N-dimethylaminopyridine (DMAP) (1 g, 0.008 mol) were added to the activated carboxylic acid. After work-up and isolation, the crude material is reacted with 50% vol-% trifluoroacetic acid in DCM. The free acid is purified by mass-guided preparative HPLC to afford the title compound (40).

Example 16

(5-Morpholinopentyl)fumarate (40)

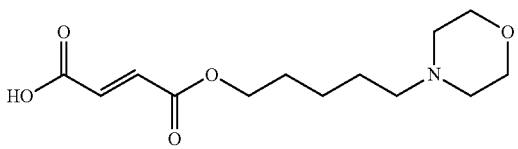 [SMILES: O=C(O)/C=C/C(=O)OCCCCCN1CCOCC1]

Following the procedure of Example 15, and replacing 4-morpholin-4ylbutyl-1-ol with 5-morpholin-4ylpentyl-1-ol provides the title compound (40).

Example 17

Methyl(6-morpholinohexyl)fumarate (Methyl 6-morpholin-4-ylhexyl(2E)but-2-ene-1,4-dioate) (9)

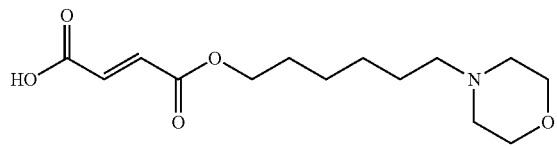 [SMILES: O=C(O)/C=C/C(=O)OCCCCCCN1CCOCC1]

Following the procedure of Example 15, and replacing 4-morphlin-4ylbutyl-1-ol with 6-morpholin-4ylhexyl-1-ol provides the title compound (41).

Example 18

Bis(3-Morpholinopropyl)fumarate (42)

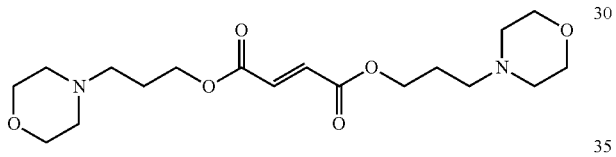

Following general procedure D, fumaric acid (0.2 mol) is activated with 1-ethyl-3-(3-dimethylaminopropyl)carbodiimide hydrochloride (EDAC) (0.25 mol) in 200 mL of dichloromethane (DCM) at ca. 0° C. 3-Morpholin-4ylpropyl-1-ol (0.2 mol) and 4-N,N-dimethylaminopyridine (DMAP) (1 g, 0.008 mol) were added to the activated carboxylic acid. After work-up and isolation, the crude is purified by mass-guided preparative HPLC to afford the tide compound (42).

Example 19

(4-Morpholinobutyl)fumarate (43)

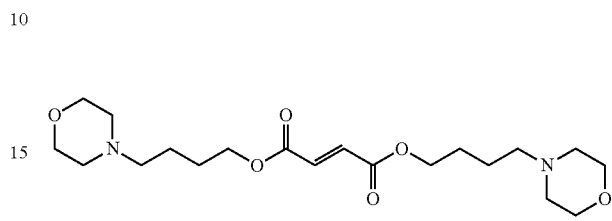

Following the procedure of Example 18, and replacing 3-morpholin-4ylpropyl-1-ol with 5-morpholin-4ylbutyl-1-ol provides the title compound (43).

Example 20

(5-Morpholinopentyl)fumarate (44)

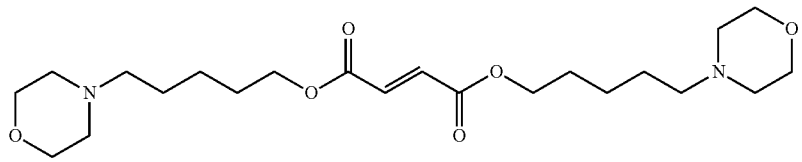 [SMILES: O=C(/C=C/C(=O)OCCCCCN1CCOCC1)OCCCCCN1CCOCC1]

Following the procedure of Example 18, and replacing 3-morpholin-4ylpropyl-1-ol with 5-morpholin-4ylpentyl-1-ol provides the title compound (44).

Example 21

(5-Morpholinopentyl)fumarate (45)

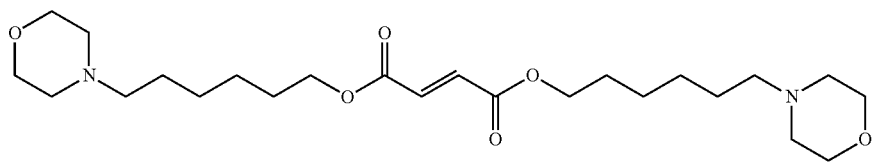 [SMILES: O=C(/C=C/C(=O)OCCCCCCN1CCOCC1)OCCCCCCN1CCOCC1]

Following the procedure of Example 18, and replacing 3-morpholin-4ylpropyl-1-ol with 6-morpholin-4ylhexyl-1-ol provides the title compound (45).

The synthetic and biological examples described in this application are offered to illustrate the compounds, pharmaceutical compositions and methods provided herein and are not to be construed in any way as limiting their scope. In the examples, all temperatures are in degrees Celsius (unless otherwise indicated). Compounds that can be prepared in accordance with the methods provided herein along with their biological and PK data are presented in following Tables. The syntheses of these representative compounds are carried out in accordance with the methods set forth above.

Exemplary Compounds Provided Herein

The following compounds have been or can be prepared according to the synthetic methods described herein.

TABLE 1

Exemplary Compounds of the Disclosure

| Compound ID | Structure |
|---|---|
| 1 | (structure: methyl fumarate ester linked to ethyl-morpholine) |
| 2 | (structure: methyl fumarate ester linked to ethyl-morpholinium chloride) |
| 3 | (structure: methyl fumarate ester linked to propyl-morpholine) |
| 4 | (structure: methyl fumarate ester linked to propyl-morpholinium chloride) |
| 5 | (structure: methyl fumarate ester linked to butyl-morpholine) |
| 6 | (structure: methyl fumarate ester linked to butyl-morpholinium chloride) |
| 7 | (structure: methyl fumarate ester linked to pentyl-morpholine) |
| 8 | (structure: methyl fumarate ester linked to pentyl-morpholinium chloride) |

TABLE 1-continued

Exemplary Compounds of the Disclosure

| Compound ID | Structure |
|---|---|
| 9 | methyl (E)-4-oxo-4-((5-morpholinopentyl)oxy)but-2-enoate |
| 10 | methyl (E)-4-oxo-4-((5-morpholinopentyl)oxy)but-2-enoate hydrochloride |
| 11 | ethyl (E)-4-(2-morpholinoethoxy)-4-oxobut-2-enoate |
| 12 | ethyl (E)-4-(2-morpholinoethoxy)-4-oxobut-2-enoate · HCl |
| 13 | propyl (E)-4-(2-morpholinoethoxy)-4-oxobut-2-enoate |
| 14 | propyl (E)-4-(2-morpholinoethoxy)-4-oxobut-2-enoate · HCl |
| 15 | butyl (E)-4-(2-morpholinoethoxy)-4-oxobut-2-enoate |
| 16 | butyl (E)-4-(2-morpholinoethoxy)-4-oxobut-2-enoate · HCl |
| 17 | pentyl (E)-4-(2-morpholinoethoxy)-4-oxobut-2-enoate |

TABLE 1-continued
Exemplary Compounds of the Disclosure
| Compound ID | Structure |
|---|---|
| 18 | 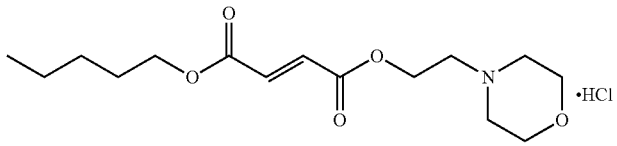 [SMILES: CCCCCOC(=O)/C=C/C(=O)OCCN1CCOCC1 ; Cl] ·HCl |
| 19 | 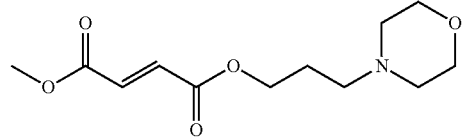 [SMILES: COC(=O)/C=C/C(=O)OCCCN1CCOCC1] |
| 20 | 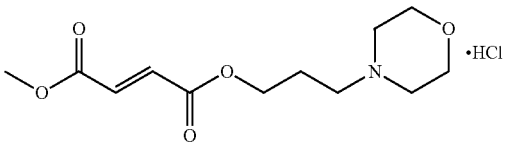 [SMILES: COC(=O)/C=C/C(=O)OCCCN1CCOCC1 ; Cl] ·HCl |
| 21 | 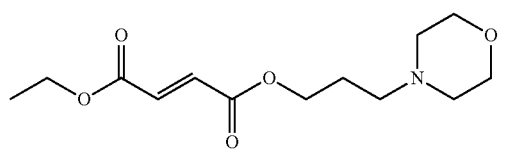 [SMILES: CCOC(=O)/C=C/C(=O)OCCCN1CCOCC1] |
| 22 | 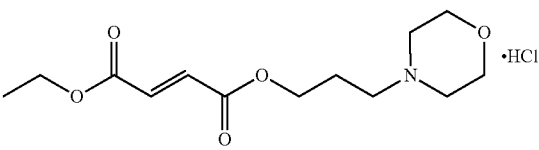 [SMILES: CCOC(=O)/C=C/C(=O)OCCCN1CCOCC1 ; Cl] ·HCl |
| 23 | 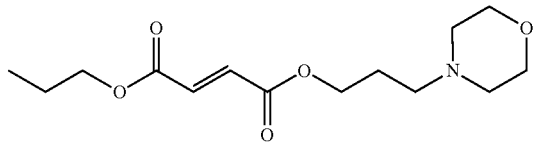 [SMILES: CCCOC(=O)/C=C/C(=O)OCCCN1CCOCC1] |
| 24 | 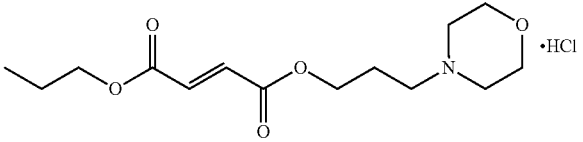 [SMILES: CCCOC(=O)/C=C/C(=O)OCCCN1CCOCC1 ; Cl] ·HCl |
| 25 | 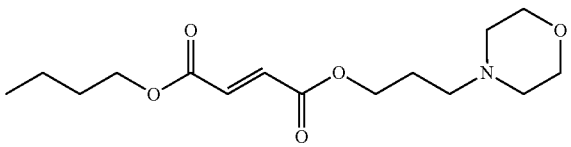 [SMILES: CCCCOC(=O)/C=C/C(=O)OCCCN1CCOCC1] |
| 26 | 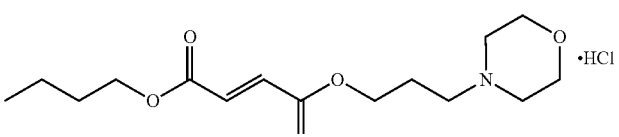 ·HCl |

TABLE 1-continued

Exemplary Compounds of the Disclosure

| Compound ID | Structure |
| --- | --- |
| 27 | pentyl ethyl fumarate linked to 3-morpholinopropyl ester |
| 28 | pentyl ethyl fumarate linked to 3-morpholinopropyl ester ·HCl |
| 29 | ethyl 4-morpholinobutyl fumarate |
| 30 | ethyl 4-morpholinobutyl fumarate ·HCl |
| 31 | propyl 4-morpholinobutyl fumarate |
| 32 | propyl 4-morpholinobutyl fumarate ·HCl |
| 33 | butyl 4-morpholinobutyl fumarate |
| 34 | butyl 4-morpholinobutyl fumarate ·HCl |
| 35 | pentyl 4-morpholinobutyl fumarate |

TABLE 1-continued
Exemplary Compounds of the Disclosure
| Compound ID | Structure |
|---|---|
| 36 | 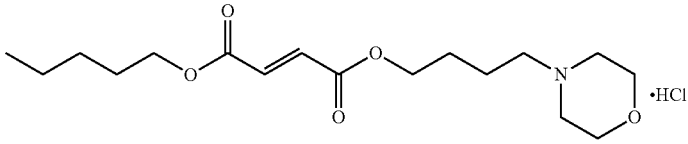 [SMILES: CCCCCOC(=O)/C=C/C(=O)OCCCCN1CCOCC1 ; Cl] |
| 37 | 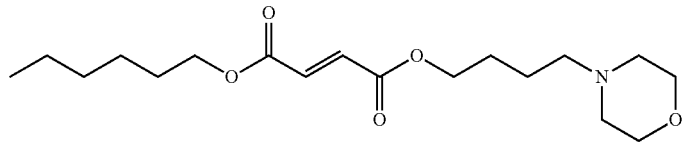 [SMILES: CCCCCCOC(=O)/C=C/C(=O)OCCCCN1CCOCC1] |
| 38 | 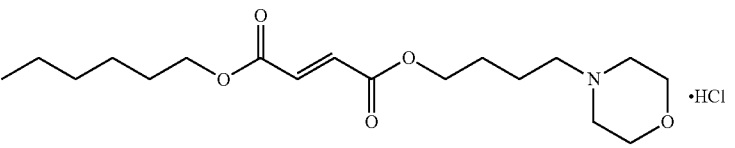 [SMILES: CCCCCCOC(=O)/C=C/C(=O)OCCCCN1CCOCC1 ; Cl] |
| 39 | 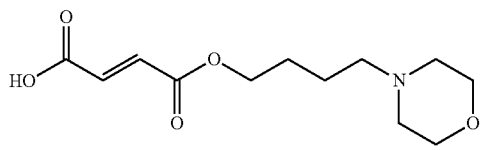 [SMILES: O=C(O)/C=C/C(=O)OCCCCN1CCOCC1] |
| 40 | 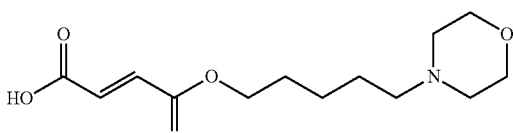 |
| 41 | 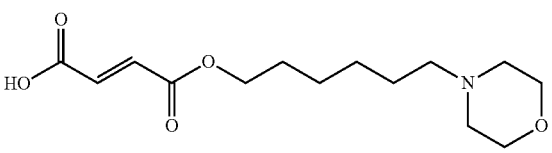 [SMILES: O=C(O)/C=C/C(=O)OCCCCCCN1CCOCC1] |
| 42 | 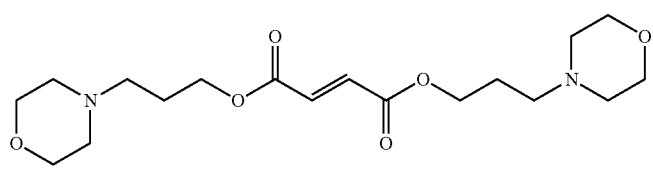 [SMILES: O=C(/C=C/C(=O)OCCCN1CCOCC1)OCCCN1CCOCC1] |
| 43 | 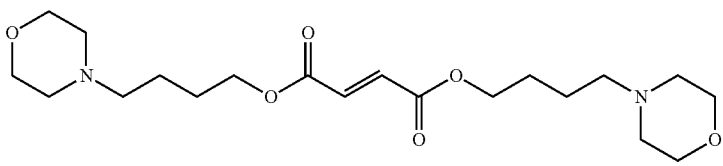 [SMILES: O=C(/C=C/C(=O)OCCCCN1CCOCC1)OCCCCN1CCOCC1] |
| 44 | 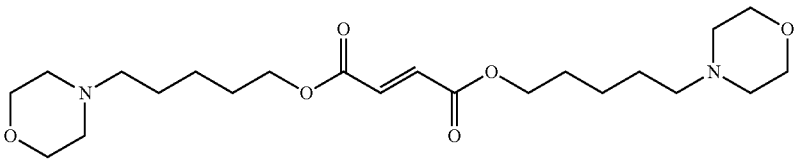 [SMILES: O=C(/C=C/C(=O)OCCCCCN1CCOCC1)OCCCCCN1CCOCC1] |

TABLE 1-continued

Exemplary Compounds of the Disclosure

| Compound ID | Structure |
|---|---|
| 45 | (structure) |

Description 1

Methods for Determining Stability of Morpholinoalkyl Fumarates In Vitro

Certain morpholinoalkyl fumarates of the disclosure may or may not themselves be pharmacologically active, and are metabolized in vivo to produce a pharmacologically active metabolite. For a prodrug, it can be desirable that the prodrug remains intact (i.e., uncleaved) while in the systemic circulation and be cleaved (i.e., to release the parent drug) in the target tissue. Alternatively, it can be desirable that the prodrug remains intact (i.e., uncleaved) while in the gastrointestinal tract and be cleaved (i.e., to release the parent drug) after being absorbed or taken up from the gastrointestinal lumen, e.g., in either the enterocytes lining the gastrointestinal lumen or in the blood. For pharmacologically active compounds, it can be desirable that the compound remains intact in the gastrointestinal tract.

A useful level of stability can at least in part be determined by the mechanism and pharmacokinetics of the prodrug or active compound. In general, prodrugs or active compounds that are more stable in pancreatin or colonic wash assay, and are more labile in rat plasma, human plasma, rat liver S9, and/or human liver S9 preparations, can be useful as an orally administered prodrug or active compound. In general, prodrugs or active compounds that are more stable in rat plasma, human plasma, rat liver S9, and/or human liver S9 preparations, and which are more labile in cell homogenate preparations such CaCo2 S9 preparations, can be useful as systemically administered prodrugs or active compounds and/or can be more effective in delivering a prodrug or active compound to a target tissue. In general, prodrugs or active compounds that are more stable in a range of pH physiological buffers (pH 6.0 to pH 8.5) can be more useful as orally administered prodrugs or active compounds. In general, prodrugs or active compounds that are more labile in cell homogenate preparations, such CaCo2 S9 preparations, can be intracellularly metabolized. The results of tests, such as those described in this example, for determining the enzymatic or chemical cleavage of compounds in vitro can be used to select prodrugs for in vivo testing.

The stabilities of prodrugs or active compounds can be evaluated in one or more in vitro systems using a variety of preparations following methods known in the art. For example, methods used to determine the stability of prodrugs in Caco2 S9 homogenate, rat liver S9, rat plasma, porcine pancreatin, rat colonic wash, and pH 8.0 buffer are described herein.

CaCo2 S9 homogenate is prepared using the following procedure. CaCo2 cells are grown in culture for 21 days prior to harvesting. Culture medium is removed from the culture vessel and the monolayer is rinsed twice with 10-15 mL chilled phosphate buffered saline (PBS) buffer. PBS buffer (7-10 mL) is added to the flask and the cells scraped from the growth surface and transferred to a centrifuge tube. The cells are pelleted by centrifugation at 1,500 rpm for 5 min at 4° C. The supernatant is removed and the cell pellet washed with ice cold PBS and re-pelleted by centrifugation. The supernatant is removed and the pellet re-suspended in cell lysis buffer (0.15M KCl and 10 mM sodium phosphate buffer, pH 7.4). Cells are lysed by sonication at 4° C. using a probe sonicator. The lysed cells are then transferred to vials and centrifuged at 1,600 rpm for 10 min at 4° C. to remove intact cells, nuclei, and large cellular debris. The supernatant is removed and transferred to a tube for centrifugation at 8,600 rpm for 20 min at 4° C. After centrifugation, the resulting supernatant, representing the CaCo2 cell homogenate S9 fraction, is carefully removed and aliquoted into vials for storage at −80° C. until the time of use. At the time of use, CaCo2 S9 lysate is diluted to 0.5 mg/mL in 0.1M Tris buffer, pH 7.4.

Rat liver S9 (XenoTech, Lenexa, Kans.; R1000.S9, 20 mg/mL) is diluted to 0.5 mg/mL in 0.1 M potassium phosphate buffer at pH 7.4 and 1 mM NADPH cofactor.

Rat plasma (Pel-Freez® Biologicals, Rogers, Ark.; 36150) is used as obtained from the supplier.

Porcine pancreatin (Sigma Aldrich, St. Louis, Mo.; P1625-100G) is diluted to 10 mg/mL in 0.1M Tris buffer, pH 7.4.

To prepare the rat colonic wash, the colon between the ceacum and rectum is resected from a euthanized rat. Five to 10 mL of PBS pH 7.4 buffer (depending on the weight of the rat) is flushed into the lumen of the large intestine and collected into a 250 mL glass beaker at 0° C. (ice bath). The colonic wash is transferred into 10 mL conical tubes using a 10 mL syringe fitted with a filter. Samples of 0.5 mL colonic wash are stored at −80° C. until the time of use. Colonic wash is used without dilution.

The enzymatic stability assays for a compound in CaCo2 S9, rat liver S9, rat plasma, pig pancreatin, and rat colonic wash are performed using the following procedure. Ninety (90) μL of lysate is aliquoted to designated tubes on a cluster plate. The lysate is pre-incubated for 10 min at 37° C. With the exception of the t(0) time point, 10 μL of a 400 μM solution of test compound in 0.1M Tris buffer, pH 7.4 is added to multiple wells, representing different incubation times. The samples are incubated at 37° C. At each time point, the reaction is quenched by adding 300 μL of 100% ethanol. The samples are thoroughly mixed, the tubes transferred to a V-bottom plate, and stored at −20° C. For the t(0) time point, the lysate is quenched with 300 μL of ice cold 100% ethanol, thoroughly mixed, 10 μL of 400 μM test compound is added and mixed, and the sample tube transferred to a V-bottom plate and stored at −20° C. For analysis, 180 μL from each sample is transferred to a 96 well V-bottom plate and sealed. After all time points are collected, the plate is centrifuged for 10 min at 5600 rpm at 4° C. One-hundred fifty (150) μL from each well is then transferred to a 96 well round bottom plate. Samples are analyzed using LC/MS/MS to determine the concentrations of the compound and/or metabolite thereof.

For the pH 8.0 stability studies, 190 μL of 150 mM NaH$_2$PO$_4$ buffer pH 8.0 is added to each sample tube. Ten (10) μL of 20 mM test compound is added to each tube and mixed. The samples are incubated for 60 min at 37° C. Following incubation, the samples are transferred to room temperature and 800 μL of 50% acetonitrile in water is added to each tube. Samples are analyzed using LC/MS/MS to determine the concentrations of the compound and/or metabolite thereof.

LC/MS/MS analysis for MHF is performed using an API 4000 equipped with an Agilent 1100 HPLC and a Leap Technologies autosampler. An HPLC Phenomenex Onyx Monolithic C18 (CHO-7644) column at a temperature of 35° C., flow rate of 2.0 mL/min, injection volume of 30 μL, and a 3-min run time is used. The mobile phase AI is 0.1% formic acid in water and Mobile phase AII is 0.1% formic acid in acetonitrile. The gradient is 98% AI/2% AII at time 0; 98% AI/2% AII at time 0.1 min; 5% AI/95% AII at time 1.4 min; 5% AI/95% AII at time 2.2 min; 98% AI/2% AII at time 2.3 min; and 98% AI/2% AII at time 3.0 min. MHF content is determined using negative ion mode (Q1 128.94; Q2 71).

Description 2

Methyl Hydrogen Fumarate Bioavailability Following Oral Administration of Morpholinoalkyl Fumarates Rats are obtained commercially and are pre-cannulated in the jugular vein. Animals are conscious at the time of the experiment. All animals are fasted overnight and until 4 hours post-dosing of a compound of the disclosure.

Blood samples (0.3 mL/sample) are collected from all animals prior to dosing and at different time-points up to 24 h post-dose into tubes containing EDTA. Two aliquots (100 μL each) are quenched with 300 μL methanol and stored at −20° C. prior to analysis.

To prepare analysis standards, 90 μL of rat blood is quenched with 300 μL methanol followed by 10 μL of spiking standard and/or 20 μL of internal standard. The sample tubes are vortexed for at least 2 min and then centrifuged at 3,400 rpm for 20 min. The supernatant is then transferred to an injection vial or plate for analysis by LC-MS-MS.

To prepare samples for analysis, 20 μL of internal standard is added to each quenched sample tube. The sample tubes are vortexed for at least 2 min and then centrifuged at 3,400 rpm for 20 min. The supernatant is then transferred to an injection vial or plate for analysis by LC/MS/MS.

LC/MS/MS analysis can be performed using an API 4000 (MS12) equipped with Agilent 1100 HPLC and a Leap Technologies autosampler. The following HPLC column conditions are used: HPLC column: Onyx Monolithic C18 Phenomex (PN CHO-7644), 35° C.; flow rate 2.0 mL/min; injection volume 30 μL; run time 3 min; mobile phase A: 0.1% formic acid in water; mobile phase B: 0.1% formic acid in acetonitrile (ACN); gradient: 98% A/2% B at 0.0 min; 98% A/2% B at 0.1 min; 5% A/95% B at 1.4 min; 5% A/95% B at 2.2 min; 98% A/2% B at 2.3 min; and 98% A/2% B at 3.0 min. MHF is monitored in negative ion mode.

Non-compartmental analysis is performed using WinNonlin software (v.3.1 Professional Version, Pharsight Corporation, Mountain View, Calif.) on individual animal profiles. Summary statistics on major parameter estimates is performed for $C_{max}$ (peak observed concentration following dosing), $T_{max}$ (time to maximum concentration is the time at which the peak concentration is observed), $AUC_{(0-t)}$ (area under the plasma concentration-time curve from time zero to last collection time, estimated using the log-linear trapezoidal method), $AUC_{(0-\infty)}$, (area under the plasma concentration time curve from time zero to infinity, estimated using the log-linear trapezoidal method to the last collection time with extrapolation to infinity), and $t_{1/2,z}$ (terminal half-life).

A compound of the disclosure is administered by oral gavage to groups of four to six adult male Sprague-Dawley rats (about 250 g). Animals are conscious at the time of the experiment. A compound of the disclosure is orally or colonically administered in 3.4% Phosal at a dose of 70 mg-equivalents MHF per kg body weight.

The percent relative bioavailability (F %) of the administered compound or metabolite thereof is determined by comparing the area under the respective concentration vs time curve (AUC) following oral or colonic administration of a compound of the disclosure with the AUC of the concentration vs time curve following intravenous administration of the compound of the disclosure, respectively, on a dose-normalized basis.

The % F can be reported as the mean % F of all animals dosed orally with the compound of the disclosure at the specified level.

The oral bioavailability (% F) values of the compounds tested along with the comparative compound, DMF, in rats and in monkeys are set forth in Table 2, below.

TABLE 2

Oral Bioavailability of Exemplary Compounds

| Compound ID | Structure | Oral Bioavailability (Rat) F (%) | Oral Bioavailability (Monkey) F (%) |
|---|---|---|---|
| 2 | (structure shown) | 25.7 | NA |

TABLE 2-continued

Oral Bioavailability of Exemplary Compounds

| Compound ID | Structure | Oral Bioavailability (Rat) F (%) | Oral Bioavailability (Monkey) F (%) |
|---|---|---|---|
| 4 | 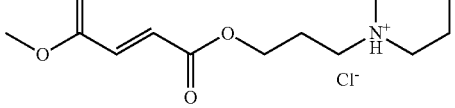 | 17.2 | NS |
| 6 | 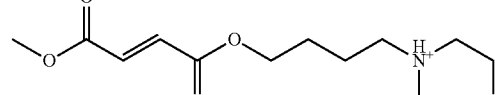 | 41.3 | 78.2 |
| 8 | 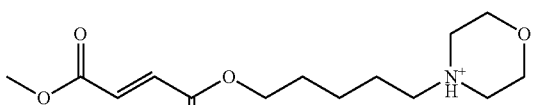 | 27.5 | NA |
| 10 | 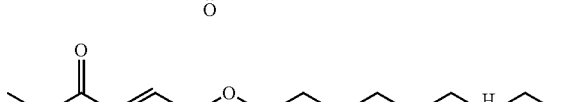 | 10.5 | NA |
| DMF | 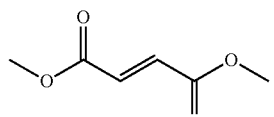 | 37 | 61 |

Description 3

Animal Model for Assessing Therapeutic Efficacy of Morpholinoalkyl Fumarates for Treating Multiple Sclerosis Animals and Experimental Autoimmune Encephalomyelitis Induction Female C57BL/6 mice, 8-10 weeks old (Harlan Laboratories, Livermore, Calif.), are immunized subcutaneously in the flanks and mid-scapular region with 200 μg of myelin oligodendrocyte glycoprotein peptide 35-55 ($MOG_{35-55}$) (synthesized by Invitrogen) emulsified (1:1 volume ratio) with complete Freund's adjuvant (CFA) (containing 4 mg/mL *Mycobacterium tuberculosis*). Emulsion is prepared by the syringe-extrusion method with two glass Luer-Lock syringes connected by a 3-way stopcock. Mice are also given an intraperitoneal injection of 200 ng pertussis toxin (List Biological Laboratories, Inc, Campbell, Calif.) on the day of immunization and on day two post immunization. Mice are weighed and examined daily for clinical signs of experimental autoimmune encephalomyelitis (EAE). Food and water is provided ad libitum and once animals start to show disease, food is provided on the cage bottom. All experiments are approved by the Institutional Animal Care and Use Committee.

Clinical Evaluation

Mice are scored daily beginning on day 7 post immunization. The clinical scoring scale is as follows (Miller and Karplus, *Current Protocols in Immunology* 2007, 15.1.1-15.1.18): 0=normal; 1=limp tail or hind limb weakness (defined by foot slips between bars of cage top while walking); 2=limp tail and hind limb weakness; 3=partial hind limb paralysis (defined as no weight bearing on hind limbs but can still move one or both hind limbs to some extent); 4=complete hind limb paralysis; 5=moribund state (includes forelimb paralysis) or death.

Treatment

Compound(s) of the disclosure are dissolved in 0.5% methocellulose/0.1% Tween80 in distilled water and administered by oral gavage twice daily starting from day 3 post-immunization until termination. Dexamethasone is dissolved in 1×PBS buffer and administered subcutaneously once daily. Treatment groups are, for example, as follows: vehicle alone, 15 mg/kg DMF, 20 mg/kg compound of the disclosure, and 1 mg/kg dexamethasone.

Alternate Animal Models of Multiple Sclerosis

The following experiment confirmed that MHF is the active moiety of both MHF prodrugs DMF and the compounds of the disclosure and examined the relationship between MHF exposure and effect in animal models of multiple sclerosis (MS). Efficacy of representative compound of the disclosure and DMF is compared in the MOG35-55 mouse EAE model of multiple sclerosis. C57BL/6 mice (6 females) are injected subcutaneously with MOG35-55 peptide in CFA with *Mycobacterium tuberculosis*. Pertussis toxin (200 mg) is injected IV on Day 0 and Day 2 post-immunization. Animals received oral test compound or DMF (90 mg-eq MHF/kg twice daily) or vehicle on Days 3 to 29. Daily EAE clinical disease scores (5 point scale) are recorded. End of study MHF blood levels are determined by LC/MS/MS.

Description 4

Use of an Animal Model to Assess Efficacy in Treating Psoriasis

The severe, combined immunodeficient (SCID) mouse model can be used to evaluate the efficacy of compounds for treating psoriasis in humans (Boehncke, *Ernst Schering Res Found Workshop* 2005, 50, 213-34; and Bhagavathula et al., *J Pharmacol Expt'l Therapeutics* 2008, 324(3), 938-947).

SCID mice are used as tissue recipients. One biopsy for each normal or psoriatic volunteer (human) is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3+ monoclonal antibody to detect human T lymphocytes in the transplanted tissue. Sections are also probed with antibodies to c-myc and β-catenin. A positive response to treatment is reflected by a reduction in the average epiderma thickness of the psoriatic skin transplants. A positive response is also associated with reduced expression of Ki-67 in keratinocytes.

Alternate Animal Models of Multiple Sclerosis and Psoriasis

Imidquimod model of skin inflammation (Fits et al *The Journal of Immunology,* 2009, 182: 5836-5845). 10-12 week old BALB/c, Il17c+/+ or Il17c−/−, or Il17re+/+ or Il17re−/− mice were administered 50 mg Aldara cream (5% Imidquimod in Graceway, 3M) in the shaved back and right ear daily for 5 days. Clinical scoring and ear thickness measurements were performed daily. Scoring was based upon the manifestation of psoriatic symptoms, such as erythema, scaling and thickness: 0, No disease. 1, Very mild erythema with very mild thickening and scaling involving a small area. 2, Mild erythema with mild thickening and scaling involving a small area. 3, Moderate erythema with moderate thickening and scaling (irregular and patchy) involving a small area (<25%). 4, Severe erythema with marked thickening and scaling (irregular and patchy) involving a moderate area (25-50%). 5, Severe erythema with marked thickening and scaling (irregular and patchy) involving a large area (>50%). Ear and back tissue were harvested on day 5 for histological evaluation.

Efficacy of compounds of the disclosure and DMF is compared in the imiquimod (IMQ) mouse model of psoriasis. Balb/c mice (10 males/group) received daily topical IMQ (5% cream) on shaved back and right ear for 5 days as described above. Animals received oral dose of a representative compound of the disclosure or DMF (45 or 90 mg-eq MMF/kg twice daily) or vehicle from Day −5 to Day 5. Erythema score is the primary outcome measure.

The Erythema score values of the compounds tested at an oral dose of 90 mg-eq MMF/kg BID for 10 days in male Balb/C mice are set forth in Table 3, below. The data shows that the compounds of the disclosure are equipotent to DMF.

TABLE 3

Efficacy of Exemplary Compounds in Psoriasis Model

| Compound ID | Erythema Score (% Relative to IMQ)* |
|---|---|
| 2 | 69 |
| 4 | 73.3 |
| 6 | 57.1 |
| 8 | 59.3 |
| 10 | 66.7 |
| DMF | 74.1 |

*oral dose of 90 mg-eq MMF/kg BID for 10 days in male Balb/C mice

Description 5

Animal Model for Assessing Therapeutic Efficacy of Morpholinoalkyl Fumarates for Treating Multiple Sclerosis Experiments are conducted on female mice aged 4-6 weeks belong to the C57BL/6 strain weighing 17-20 g. Experimental autoimmune encephalomyelitis (EAE) is actively induced using ≥95% pure synthetic myelin oligodendrocyte glycoprotein peptide 35-55 ($MOG_{35-55}$) (synthesized by Invitrogen). Each mouse is anesthetized and receives 200 μg of $MOG_{35-55}$ peptide and 15 μg of Saponin extract from Quilija bark emulsified in 100 μL of phosphate-buffered saline. A 25 μL volume is injected subcutaneously over four flank areas. Mice are also intraperitoneally injected with 200 ng of pertussis toxin in 200 μL of PBS. A second, identical injection of pertussis toxin is given after 48 h.

A compound of the disclosure is administered at varying doses. Control animals receive 25 μL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hind limbs); 2, unilateral partial hind limb paralysis; 2.5, bilateral hind limb paralysis; 3, complete bilateral hindlimb paralysis; 3.5, complete hindlimb paralysis and unilateral forelimb paralysis; 4, total paralysis of hind limbs and forelimbs (Eugster et al., *Eur J Immunol* 2001, 31, 2302-2312).

Inflammation and demyelination are assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then re-suspended in PBS and counted. Cells at a density of about $3 \times 10^6$ cells/mL are incubated overnight with 20 μg/mL of MOG peptide. Supernatants from stimulated cells are assayed for IFN-γ protein levels using an appropriate mouse IFN-γ immunoassay system.

Description 6

Use of an Animal Model to Assess Efficacy in Treating Inflammatory Bowel Disease Animal models of inflammatory bowel disease are described by Jurjus et al., *J Pharmaocol Toxicol Methods* 2004, 50, 81-92; Villegas et al., *Int'l Immunopharmacol* 2003, 3, 1731-1741; and Murakami et al., *Biochemical Pharmacol* 2003, 66, 1253-1261. For example, the following protocol can be used to assess the efficacy of a compound of the disclosure for treating inflammatory bowel disease.

Female ICR mice are used. Mice are divided into treatment groups. Groups are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are sacrificed and the large intestine is removed. Colonic mucosa samples are obtained and homogenized. Proinflammatory mediators (e.g., IL-1α, IL-1β, TNF-α, PGE2, and PGF2α) and protein concentrations are quantified. Each excised large intestine is histologically examined and the damage to the colon scored.

Description 7

Clinical Trial for Assessing Efficacy in Treating Asthma

Adult subjects (nonsmokers) with stable mild-to-moderate asthma are enrolled (see, e.g., Van Schoor and Pauwels, *Eur Respir J* 2002, 19, 997-1002). A randomized, double-blind, placebo-controlled, two-period crossover design is used. On screening day 1, patients undergo a methacholine challenge (<8 mg/mL). The baseline forced expiratory volume in one second (FEV1) prior to each subsequent challenge must be within 15% of the screening baseline FEV1 obtained at the first visit. A neurokinin challenge ($1\times10^{-6}$ mol/mL) on screening day 2 is performed 24-72 h later. Study-period one commences within 10 days after visit two. First, a methacholine and a neurokinin-A (NKA) challenge is performed on days 1 and 0, respectively. At visit four, test compound is administered at an appropriate dose and for an appropriate period of time. On the last 2 days of the treatment period, methacholine and NKA challenges are repeated. Following treatment-period one, there is a washout period of about 5 weeks, following which the patients crossed over to another medication or placebo in study period two, which is identical to period one. Pulmonary function tests are performed using a spirometer. The metacholine challenge is performed by inhaling doubling concentrations of methacholine until the FEV1 falls by >20% of the post-diluent baseline FEV1 of that day as described by Cockcroft et al., *Clin Allergy* 1977, 7, 235-243. NKA challenge is performed by inhaling increasing concentrations of NKA as described by Van Schoor et al., *Eur Respir J* 1998, 12, 17-23. The effect of a treatment on airway responsiveness is determined using appropriate statistical methods.

Description 8

Use of an Animal Model to Assess Efficacy in Treating Chronic Obstructive Pulmonary Disease An animal model using mice chronically exposed to cigarette smoke can be used for assessing efficacy in treating emphysema (see, e.g., Martorana et al., *Am J Respir Crit Care Med* 2005, 172, 848-835; and Cavarra et al., *Am J Respir Crit Care Med* 2001, 164, 886-890). Six-week old C57B1/6J male mice are used. In the acute study, the mice are exposed either to room air or to the smoke of five cigarettes for 20 minutes. In the chronic study, the mice are exposed to either room air or to the smoke of three cigarettes/day, for 5 days/week, for 7 months.

For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

For the chronic study, five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are sacrificed and the lungs fixed intratracheally with formalin. Lung volume is measured by water displacement. Lungs are stained. Assessment of emphysema includes mean linear intercept and internal surface area. The volume density of macrophages, marked immunohistochemically with anti-mouse Mac-3 monoclonal antibodies is determined by point counting. A mouse is considered to have goblet cell metaplasia when at least one or more midsize bronchi/lung showed a positive periodic acid-Schiff staining. For the determination of desmosine, fresh lungs are homogenized, processed, and analyzed by high-pressure liquid chromatography.

Description 9

Animal Models for Assessing Therapeutic Efficacy of Morpholinoalkyl Fumarates for Treating Parkinson's Disease MPTP Induced Neurotoxicity MPTP, or 1-methyl-4-phenyl-1,2,3,6-tetrahydropyridine is a neurotoxin that produces a Parkinsonian syndrome in both humans and experimental animals. Studies of the mechanism of MPTP neurotoxicity show that it involves the generation of a major metabolite, MPP$^+$, formed by the activity of monoamine oxidase on MPTP. Inhibitors of monoamine oxidase block the neurotoxicity of MPTP in both mice and primates. The specificity of the neurotoxic effects of MPP for dopaminergic neurons appears to be due to the uptake of MPP by the synaptic dopamine transporter. Blockers of this transporter prevent MPP neurotoxicity. MPP has been shown to be a relatively specific inhibitor of mitochondrial complex I activity, binding to complex I at the retenone binding site and impairing oxidative phosphorylation. In vivo studies have shown that MPTP can deplete striatal ATP concentrations in mice. It has been demonstrated that MPP administered intrastriatally to rats produces significant depletion of ATP as well as increased lactate concentration confined to the striatum at the site of the injections. Compounds that enhance ATP production can protect against MPTP toxicity in mice.

A compound of the disclosure is administered to animals such as mice or rats for three weeks before treatment with MPTP. MPTP is administered at an appropriate dose, dosing interval, and mode of administration for 1 week before sacrifice. Control groups receive either normal saline or MPTP hydrochloride alone. Following sacrifice the two striate are rapidly dissected and placed in chilled 0.1 M perchloric acid. Tissue is subsequently sonicated and aliquots analyzed for protein content using a fluorometer assay. Dopamine, 3,4-dihydroxyphenylacetic acid (DOPAC), and homovanillic acid (HVA) are also quantified. Concentrations of dopamine and metabolites are expressed as nmol/mg protein.

Compounds of the disclosure that protect against DOPAC depletion induced by MPTP, HVA, and/or dopamine depletion are neuroprotective and therefore can be useful for the treatment of Parkinson's disease.

Haloperidol-Induced Hypolocomotion

The ability of a compound to reverse the behavioral depressant effects of dopamine antagonists, such as haloperidol, in rodents is considered a valid method for screening drugs with potential anti-Parkinsonian effects (Mandhane, et al., *Eur. J. Pharmacol* 1997, 328, 135-141). Hence, the ability of compounds of Formula (I) or Formula (II) to block haloperidol-induced deficits in locomotor activity in mice can be used to assess both in vivo and potential anti-Parkinsonian efficacy.

Mice used in the experiments are housed in a controlled environment and allowed to acclimatize before experimental use. One and one-half (1.5) hours before testing, mice are administered 0.2 mg/kg haloperidol, a dose that reduces baseline locomotor activity by at least 50%. A test compound is administered 5-60 min prior to testing. The animals are then placed individually into clean, clear polycarbonate cages with a flat perforated lid. Horizontal locomotor activity is determined by placing the cages within a frame containing a 3×6 array of photocells interfaced to a computer to tabulate beam interrupts. Mice are left undisturbed to explore for 1 h, and the number of beam interruptions made during this period serves as an indicator of locomotor activity, which is compared with data for control animals for statistically significant differences.

6-Hydroxydopamine Animal Model

The neurochemical deficits seen in Parkinson's disease can be reproduced by local injection of the dopaminergic neurotoxin, 6-hydroxydopamine (6-OHDA) into brain regions containing either the cell bodies or axonal fibers of the nigrostriatal neurons. By unilaterally lesioning the nigrostriatal pathway on only one-side of the brain, a behavioral asymmetry in movement inhibition is observed. Although unilaterally-lesioned animals are still mobile and capable of self-maintenance, the remaining dopamine-sensitive neurons on the lesioned side become supersensitive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has been shown to be a sensitive model to predict drug efficacy in the treatment of Parkinson's disease.

Male Sprague-Dawley rats are housed in a controlled environment and allowed to acclimatize before experimental use. Fifteen minutes prior to surgery, animals are given an intraperitoneal injection of the noradrenergic uptake inhibitor desipramine (25 mg/kg) to prevent damage to nondopamine neurons. Animals are then placed in an anesthetic chamber and anesthetized using a mixture of oxygen and isoflurane. Once unconscious, the animals are transferred to a stereotaxic frame, where anesthesia is maintained through a mask. The top of the head is shaved and sterilized using an iodine solution. Once dry, a 2 cm long incision is made along the midline of the scalp and the skin retracted and clipped back to expose the skull. A small hole is then drilled through the skull above the injection site. In order to lesion the nigrostriatal pathway, the injection cannula is slowly lowered to position above the right medial forebrain bundle at −3.2 mm anterior posterior, −1.5 mm medial lateral from the bregma, and to a depth of 7.2 mm below the dura mater. Two minutes after lowering the cannula, 6-OHDA is infused at a rate of 0.5 µL/min over 4 min, to provide a final dose of 8 µg. The cannula is left in place for an additional 5 min to facilitate diffusion before being slowly withdrawn. The skin is then sutured shut, the animal removed from the sterereotaxic frame, and returned to its housing. The rats are allowed to recover from surgery for two weeks before behavioral testing.

Rotational behavior is measured using a rotameter system having stainless steel bowls (45 cm dia×15 cm high) enclosed in a transparent Plexiglas cover around the edge of the bowl and extending to a height of 29 cm. To assess rotation, rats are placed in a cloth jacket attached to a spring tether connected to an optical rotameter positioned above the bowl, which assesses movement to the left or right either as partial (45°) or full (360°) rotations.

To reduce stress during administration of a test compound, rats are initially habituated to the apparatus for 15 min on four consecutive days. On the test day, rats are given a test compound, e.g., a compound of Formula (I) or Formula (II). Immediately prior to testing, animals are given a subcutaneous injection of a sub-threshold dose of apomorphine, and then placed in the harness and the number of rotations recorded for one hour. The total number of full contralateral rotations during the hour test period serves as an index of anti-Parkinsonian drug efficacy.

Description 10

Animal Model for Assessing Therapeutic Efficacy of Morpholinoalkyl Fumarates for Treating Alzheimer's Disease Heterozygous transgenic mice expressing the Swedish AD mutant gene, hAPPK670N, M671L (Tg2576; Hsiao, *Learning & Memory* 2001, 8, 301-308) are used as an animal model of Alzheimer's disease. Animals are housed under standard conditions with a 12:12 light/dark cycle and food and water available ad libitum. Beginning at 9 months of age, mice are divided into three groups. The first two groups of animals receive increasing doses of a compound of Formula (I) or Formula (II), over six weeks. The remaining control group receives daily saline injections for six weeks.

Behavioral testing is performed at each drug dose using the same sequence over two weeks in all experimental groups: (1) spatial reversal learning, (2) locomotion, (3) fear conditioning, and (4) shock sensitivity.

Acquisition of the spatial learning paradigm and reversal learning are tested during the first five days of test compound administration using a water T-maze as described in Bardgett et al., *Brain Res Bull* 2003, 60, 131-142. Mice are habituated to the water T-maze during days 1-3, and task acquisition begins on day 4. On day 4, mice are trained to find the escape platform in one choice arm of the maze until 6 to 8 correct choices are made on consecutive trails. The reversal learning phase is then conducted on day 5. During the reversal learning phase, mice are trained to find the escape platform in the choice arm opposite from the location of the escape platform on day 4. The same performance criteria and inter-trial interval are used as during task acquisition.

Large ambulatory movements are assessed to determine that the results of the spatial reversal learning paradigm are not influenced by the capacity for ambulation. After a rest period of two days, horizontal ambulatory movements, excluding vertical and fine motor movements, are assessed in a chamber equipped with a grid of motion-sensitive detectors on day 8. The number of movements accompanied by simultaneous blocking and unblocking of a detector in the horizontal dimension are measured during a one-hour period.

The capacity of an animal for contextual and cued memory is tested using a fear conditioning paradigm beginning on day 9. Testing takes place in a chamber that contains a piece of absorbent cotton soaked in an odor-emitting solution such as mint extract placed below the grid floor. A 5-min, 3 trial 80 db, 2800 Hz tone-foot shock sequence is administered to train the animals on day 9. On day 10, memory for context is tested by returning each mouse to the chamber without exposure to the tone and foot shock, and recording the presence or absence of freezing behavior every 10 seconds for 8 minutes. Freezing is defined as no movement, such as ambulation, sniffing or stereotypy, other than respiration.

On day 11, the response of the animal to an alternate context and to the auditory cue is tested. Coconut extract is placed in a cup and the 80 dB tone is presented, but no foot shock is delivered. The presence or absence of freezing in response to the alternate context is then determined during the first 2 minutes of the trial. The tone is then presented continuously for the remaining 8 minutes of the trial, and the presence or absence of freezing in response to the tone is determined.

On day 12, the animals are tested to assess their sensitivity to the conditioning stimulus, i.e., foot shock.

Following the last day of behavioral testing, animals are anesthetized and the brains removed, post-fixed overnight, and sections cut through the hippocampus. The sections are stained to image β-amyloid plaques.

Data is analyzed using appropriate statistical methods.

Description 11

Animal Model for Assessing Therapeutic Efficacy of Morpholinoalkyl Fumarates for Treating Huntington's Disease Neuroprotective Effects in a Transgenic Mouse Model of Huntington's Disease Transgenic HD mice of the N171-82Q strain and non-transgenic littermates are treated with a compound of Formula (I), a compound of Formula (II), or a vehicle from 10 weeks of age. The mice are placed on a rotating rod ("rotarod"). The length of time at which a mouse falls from the rotarod is recorded as a measure of motor coordination. The total distance traveled by a mouse is also recorded as a measure of overall locomotion. Mice administered compounds of the disclosure that are neuroprotective in the N171-82Q transgenic HD mouse model remain on the rotarod for a longer period of time and travel farther than mice administered vehicle.

Malonate Model of Huntington's Disease

A series of reversible and irreversible inhibitors of enzymes involved in energy generating pathways has been used to generate animal models for neurodegenerative diseases such as Parkinson's and Huntington's diseases. In particular, inhibitors of succinate dehydrogenase, an enzyme that impacts cellular energy homeostasis, has been used to generate a model for Huntington's disease.

To evaluate the effect of compounds of Formula (I) or Formula (II) in this malonate model for Huntington's disease, a compound of Formula (I) or Formula (II) is administered at an appropriate dose, dosing interval, and route, to male Sprague-Dawley rats. A compound of Formula (I) or Formula (II) is administered for two weeks prior to the administration of malonate and then for an additional week prior to sacrifice. Malonate is dissolved in distilled deionized water and the pH adjusted to 7.4 with 0.1 M HCl. Intrastriatal injections of 1.5 µL of 3 µmol malonate are made into the left striatum at the level of the Bregma, 2.4 mm lateral to the midline and 4.5 mm ventral to the dura. Animals are sacrificed at 7 days by decapitation and the brains quickly removed and placed in ice cold 0.9% saline solution. Brains are sectioned at 2 mm intervals in a brain mold. Slices are then placed posterior side down in 2% 2,3,5-tiphenyltetrazolium chloride. Slices are stained in the dark at room temperature for 30 min and then removed and placed in 4% paraformaldehyde pH 7.3. Lesions, noted by pale staining, are evaluated on the posterior surface of each section. The measurements are validated by comparison with measurements obtained on adjacent Nissl stain sections. Compounds exhibiting a neuroprotective effect and therefore potentially useful in treating Huntington's disease show a reduction in malonate-induced lesions.

Description 12

Animal Model for Assessing Therapeutic Efficacy of Morpholinoalkyl Fumarates for Treating Amyotrophic Lateral Sclerosis A murine model of SOD1 mutation-associated ALS has been developed in which mice express the human superoxide dismutase (SOD) mutation glycine→alanine at residue 93 (SOD1). These SOD1 mice exhibit a dominant gain of the adverse property of SOD, and develop motor neuron degeneration and dysfunction similar to that of human ALS. The SOD1 transgenic mice show signs of posterior limb weakness at about 3 months of age and die at 4 months. Features common to human ALS include astrocytosis, microgliosis, oxidative stress, increased levels of cyclooxygenase/prostaglandin, and, as the disease progresses, profound motor neuron loss.

Studies are performed on transgenic mice overexpressing human Cu/Zn-SOD G93A mutations (B6SJL-TgN (SOD1-G93A) 1 Gur) and non-transgenic B6/SJL mice and their wild litter mates. Mice are housed on a 12-hr day/light cycle and (beginning at 45 d of age) allowed ad libitum access to either test compound-supplemented chow, or, as a control, regular formula cold press chow processed into identical pellets. Genotyping can be conducted at 21 days of age as described in Gurney et al., Science 1994, 264(5166), 1772-1775. The SOD1 mice are separated into groups and treated with a test compound, e.g., compound of Formula (I) or Formula (II), or serve as controls.

The mice are observed daily and weighed weekly. To assess health status mice are weighed weekly and examined for changes in lacrimation/salivation, palpebral closure, ear twitch and pupillary responses, whisker orienting, postural and righting reflexes and overall body condition score. A general pathological examination is conducted at the time of sacrifice.

Motor coordination performance of the animals can be assessed by one or more methods known to those skilled in the art. For example, motor coordination can be assessed using a neurological scoring method. In neurological scoring, the neurological score of each limb is monitored and recorded according to a defined 4-point scale: 0—normal reflex on the hind limbs (animal will splay its hind limbs when lifted by its tail); 1—abnormal reflex of hind limbs (lack of splaying of hind limbs when animal is lifted by the tail); 2—abnormal reflex of limbs and evidence of paralysis; 3—lack of reflex and complete paralysis; and 4—inability to right when placed on the side in 30 seconds or found dead. The primary end point is survival with secondary end points of neurological score and body weight. Neurological score observations and body weight are made and recorded five days per week. Data analysis is performed using appropriate statistical methods.

The rotarod test evaluates the ability of an animal to stay on a rotating dowel allowing evaluation of motor coordination and proprioceptive sensitivity. The apparatus is a 3 cm diameter automated rod turning at, for example, 12 rounds per min. The rotarod test measures how long the mouse can maintain itself on the rod without falling. The test can be stopped after an arbitrary limit, for example at 120 sec. If the animal falls down before 120 sec, the performance is recorded and two additional trials are performed. The mean time of 3 trials is calculated. A motor deficit is indicated by a decrease of walking time.

In the grid test, mice are placed on a grid (length: 37 cm, width: 10.5 cm, mesh size: 1×1 cm$^2$) situated above a plane support. The number of times the mice put their paws through the grid is counted and serves as a measure for motor coordination.

The hanging test evaluates the ability of an animal to hang on a wire. The apparatus is a wire stretched horizontally 40 cm above a table. The animal is attached to the wire by its forepaws. The time needed by the animal to catch the string with its hind paws is recorded (60 sec max) during three consecutive trials.

Electrophysiological measurements (EMG) can also be used to assess motor activity condition. Electromyographic recordings are performed using an electromyography apparatus. During EMG monitoring mice are anesthetized. The measured parameters are the amplitude and the latency of the compound muscle action potential (CMAP). CMAP is measured in gastrocnemius muscle after stimulation of the sciatic nerve. A reference electrode is inserted near the Achilles tendon and an active needle placed at the base of the tail. A ground needle is inserted on the lower back of the mice. The sciatic nerve is stimulated with a single 0.2 msec pulse at supramaximal intensity (12.9 mA). The amplitude (mV) and the latency of the response (ms) are measured. The amplitude is indicative of the number of active motor units, while distal latency reflects motor nerve conduction velocity.

The efficacy of test compounds can also be evaluated using biomarker analysis. To assess the regulation of protein biomarkers in SOD1 mice during the onset of motor impairment, samples of lumbar spinal cord (protein extracts) are applied to ProteinChip Arrays with varying surface chemical/biochemical properties and analyzed, for example, by surface enhanced laser desorption ionization time of flight mass spectrometry. Then, using integrated protein mass profile analysis methods data is used to compare protein expression profiles of the various treatment groups. Analysis can be performed using appropriate statistical methods.

Description 13

Animal Model for Assessing GI Irritation of Morpholinoalkyl Fumarates

At least one MMF prodrug, e.g., dimethyl fumarate, is known to cause gastrointestinal irritation. The Annamalai-Ma gastrointestinal irritation rat model is predictive of gastrointestinal irritation of MMF prodrugs in humans. This animal model has several common features of other published GI irritation animal models including the Whiteley-Dalrymple model described in Models of Inflammation: Measuring Gastrointestinal Ulceration in the Rat, Pharmacology (1998) 10.2.1-10.2.4; as well as the animal models disclosed in Joseph J. Bertone, DVM, MS, DipACVIM. Prevalence of Gastric Ulcers in Elite, Heavy Use Western Performance Horses, AAEP Proceedings/Vol. 46/2000; and İsbíl Büyükcoskun N., Central Effects of Glucagon-like Peptide-1 on Cold Restraint Stress-induced Gastric Mucosal Lesions, Physiol. Res. 48: 451-455, 1999.

In order to assess gastrointestinal irritation using this model, rats are treated orally with either vehicle or the MMF prodrug of the present disclosure (n=10 per group) at 180 mg-equivalents MMF/kg of animal body weight, dosed once per day for 4 days, followed by necropsy and gastrointestinal evaluation at 24 hrs after the final dose. Evans Blue dye is injected IV (tail vein) to visually emphasize any lesions in the gastrointestinal tissue.

Accordingly, rats are dosed once per day for 4 consecutive days with 180 mg-equivalents MMF/kg body weight per day. The animals are fasted overnight prior to necropsy. On Day 5, to help visualize lesions, 1 mL of 1% Evan's blue in saline is injected into the tail vein 30 minutes prior to euthanasia. The animals are euthanized by inhalation of carbon dioxide. A partial necropsy, limited to the abdominal cavities, is then performed. The stomach and small intestine are removed. Residual material is washed away, using an irrigation syringe filled with saline. The stomach is cut along the larger curvature and washed gently with normal saline, and is examined for any lesions. The stomachs are scored in accordance with the scoring system outlined in Table 4.

TABLE 4

Scoring System for Stomach Lesions in the Rat

| Score | Characteristics |
|---|---|
| 0 | Normal mucosa. |
| 1 | Non-erosive mucosal changes. Swelling and reddening without any apparent mucosal defect. |
| 2 | Apparent mucosal erosions. |
| 3 | Mild ulceration 1-5 small lesions (1-2 mm). |
| 4 | Moderate ulceration: More than 5 small lesions or 1 intermediate lesion (3-4 mm). |
| 5 | Severe ulceration: two or more intermediate lesions or gross lesions (longer than 4 mm). |

The GI irritation score values of the compounds tested are set forth in Table 5, below and in FIG. 1. The GI data given below clearly shows a several fold improvement over dimethyl fumarate (DMF) and a Comparative Compound. Moreover, the representative compounds of the disclosure showed normal mucosa or almost no stomach irritation.

TABLE 5

GI Effect of Exemplary Compounds

| Compound ID | Structure | Stomach Irritation Score |
|---|---|---|
| 2 | 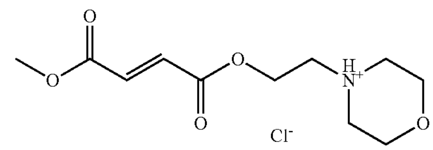 | 0 |
| 4 | 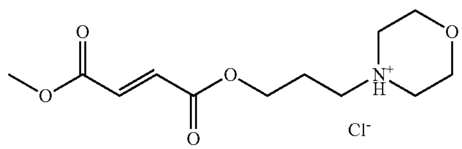 | 0 |
| 6 | 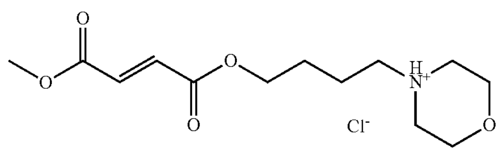 | 0.6 |
| 8 | 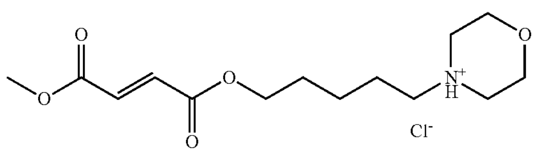 | 0 |
| 10 | 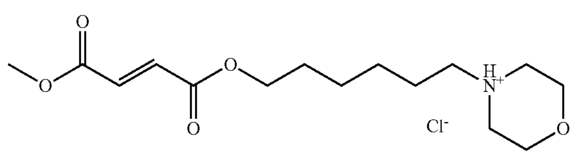 | 0 |
| CC-1 | 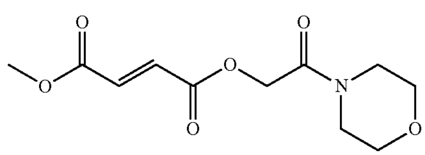 [SMILES: COC(=O)/C=C/C(=O)OCC(=O)N1CCOCC1] | 2.9 |
| DMF | 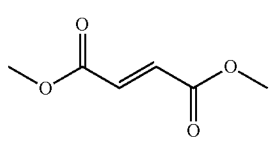 | 4.6 |

Finally, it should be noted that there are alternative ways of implementing the embodiments disclosed herein. Accordingly, the present embodiments are to be considered as illustrative and not restrictive, and the claims are not to be limited to the details given herein, but may be modified within the scope and equivalents thereof.

From the foregoing description, various modifications and changes in the compositions and methods of this disclosure will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

At least some of the chemical names of compounds of the disclosure as given and set forth in this application, may have been generated on an automated basis by use of a commercially available chemical naming software program, and have not been independently verified. In the instance where the indicated chemical name and the depicted structure differ, the depicted structure will control.

Chemical structures shown herein were prepared using ChemDraw or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A compound according to Formula (I):

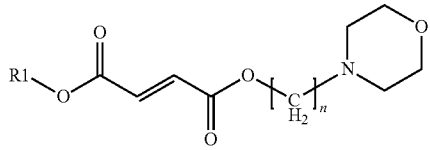

or a pharmaceutically acceptable salt thereof;
wherein:
n is an integer from 2 to 6; and
R¹ is selected from H, methyl, ethyl, and $C_{3-6}$ alkyl,
provided that when R¹ is H, then n is 4, 5, or 6.

2. The compound according to claim 1, wherein R¹ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl, or 3,3-dimethylbutyl.

3. The compound according to claim 1, wherein R¹ is methyl.

4. The compound according to claim 1, wherein the compound is a pharmaceutically acceptable salt.

5. The compound according to claim 1, wherein the compound is a HCl salt.

6. A compound selected from the group consisting of:

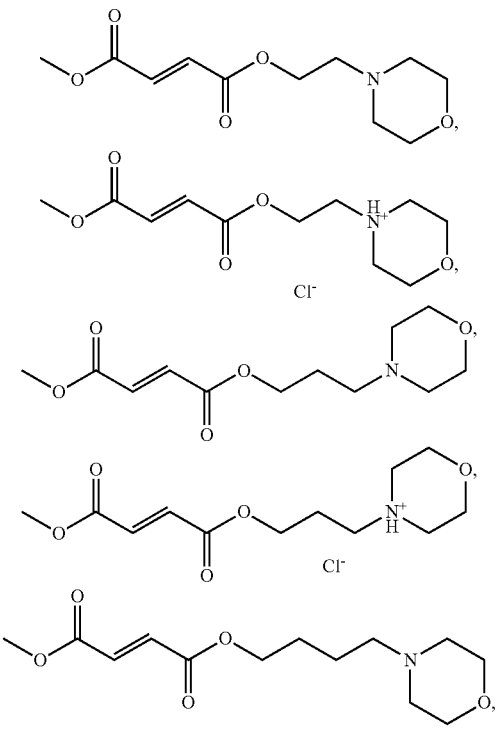

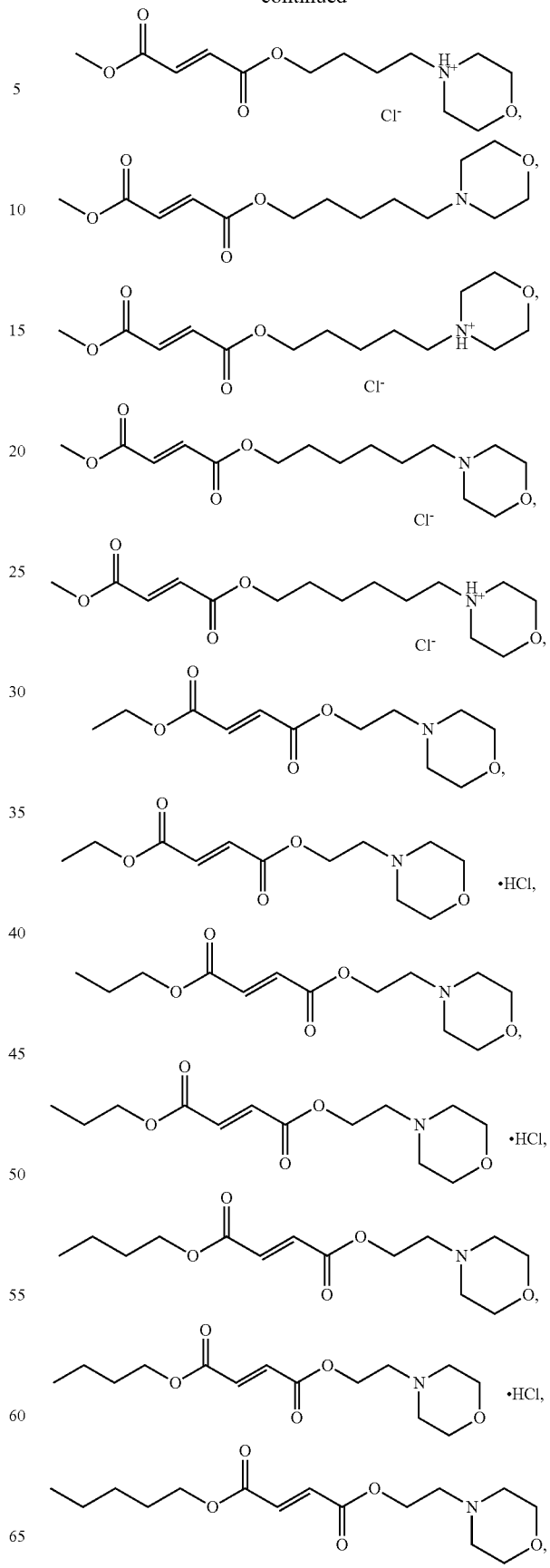

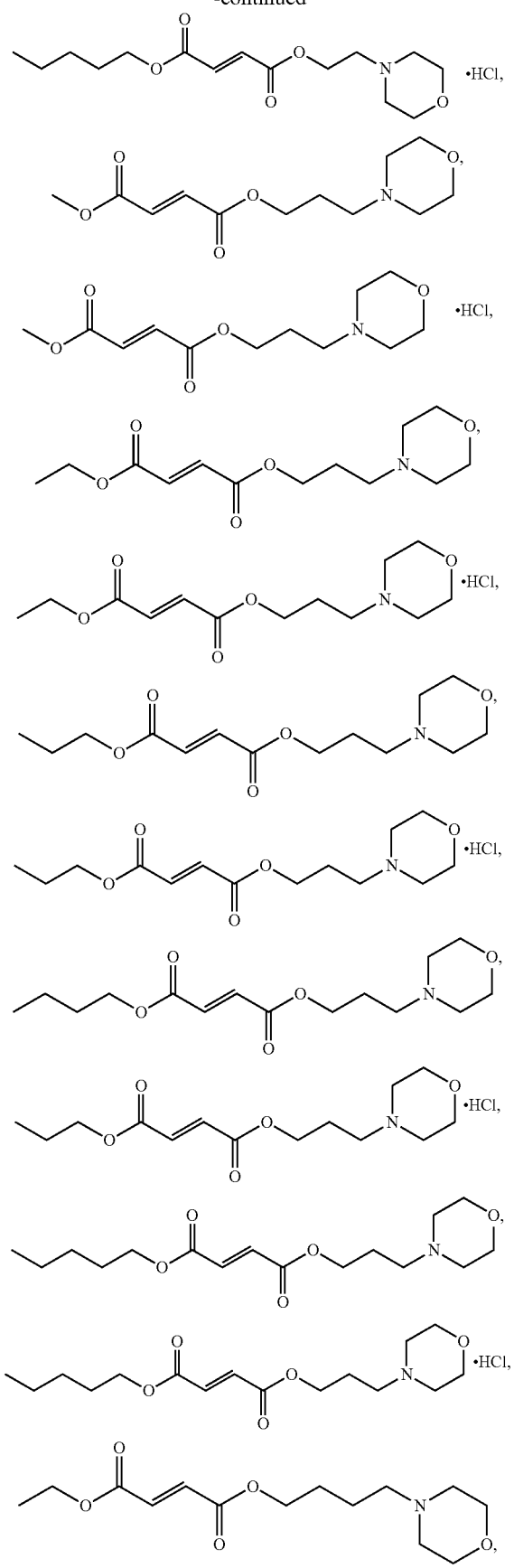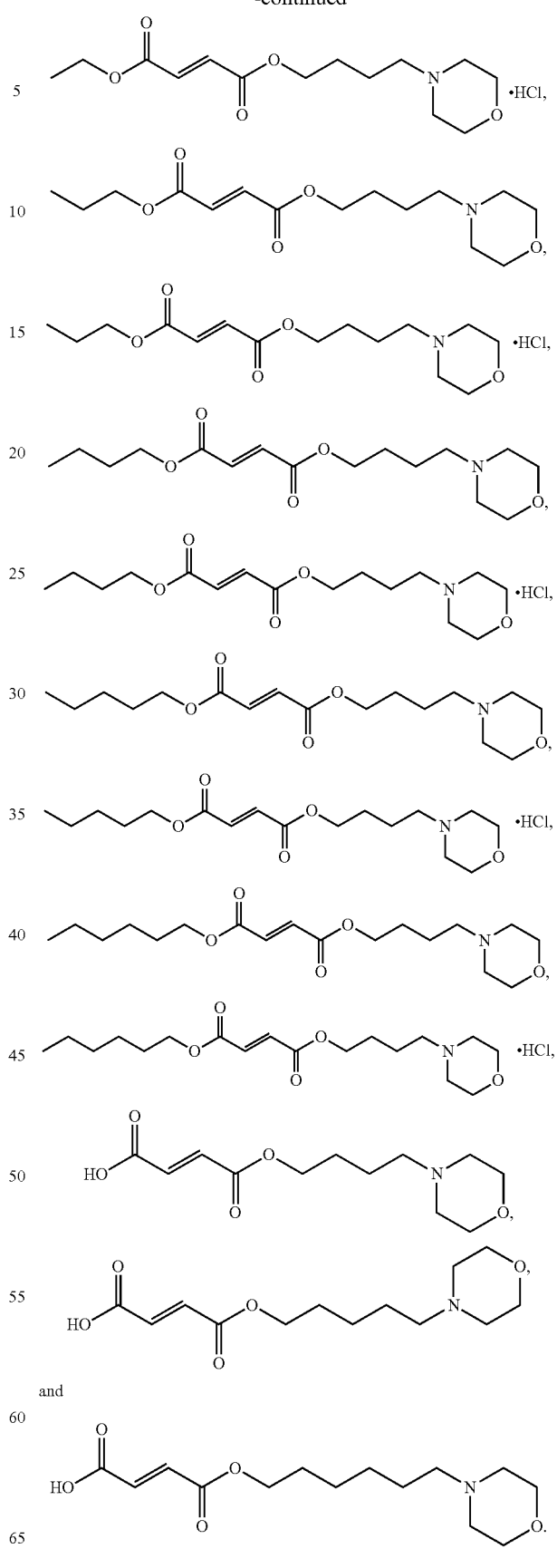

7. A compound according to Formula (IIIc):

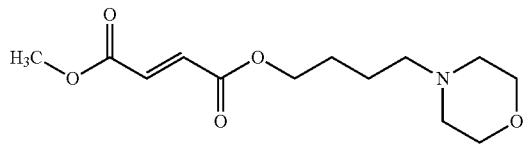

or a pharmaceutically acceptable salt thereof.

8. The compound according to claim 7, wherein the compound is a HCl salt.

9. A pharmaceutical composition comprising a pharmaceutically acceptable vehicle and a therapeutically effective amount of a compound of Formula (I):

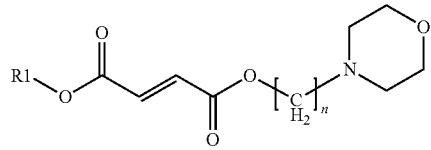

or a pharmaceutically acceptable salt thereof;
wherein:
n is an integer from 2 to 6; and
$R^1$ is selected from H methyl, ethyl, and $C_{3-6}$ alkyl.

10. The pharmaceutical composition according to claim 9, wherein $R^1$ is methyl.

11. The pharmaceutical composition according to claim 9, wherein $R^1$ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl, or 3,3-dimethylbutyl.

12. The pharmaceutical composition according to claim 9, wherein the compound is a pharmaceutically acceptable salt.

13. The pharmaceutical composition according to claim 9, wherein the compound is a HCl salt.

14. A pharmaceutical composition comprising a pharmaceutically acceptable vehicle and a therapeutically effective amount of a compound selected from the group consisting of:

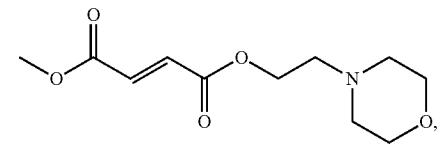

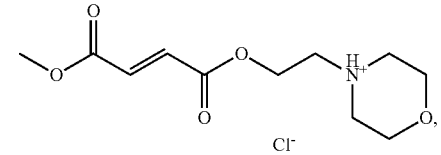

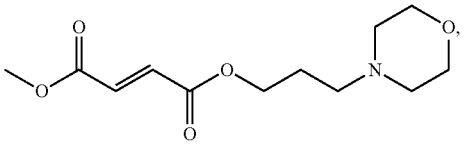

-continued

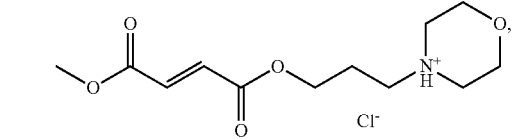

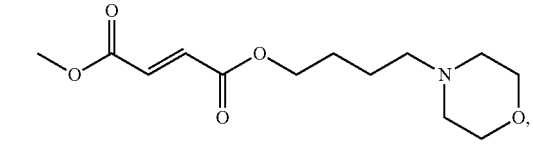

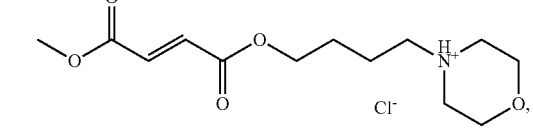

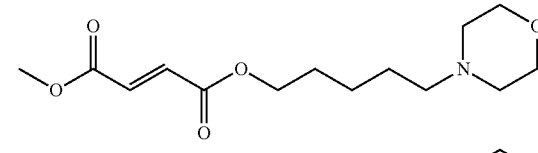

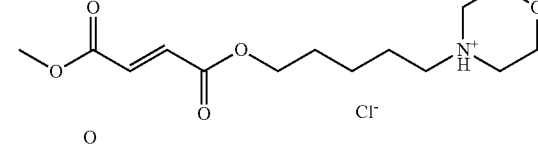

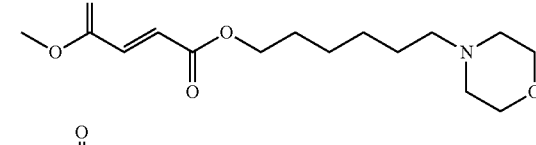

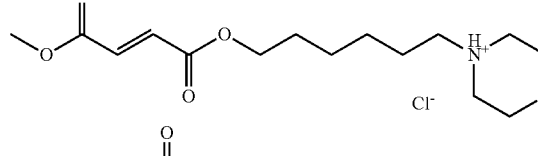

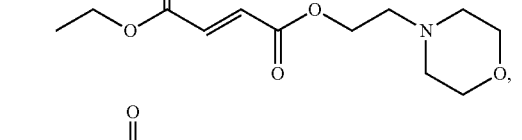

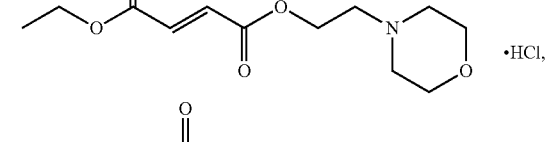

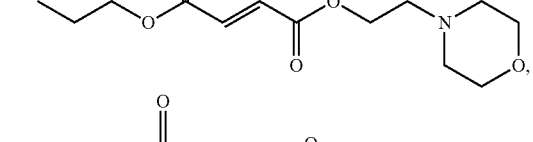

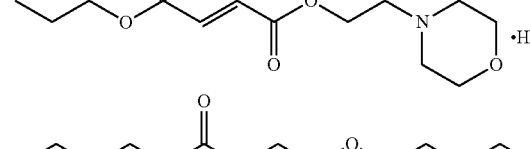

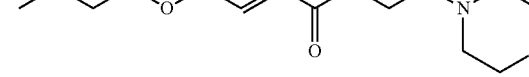

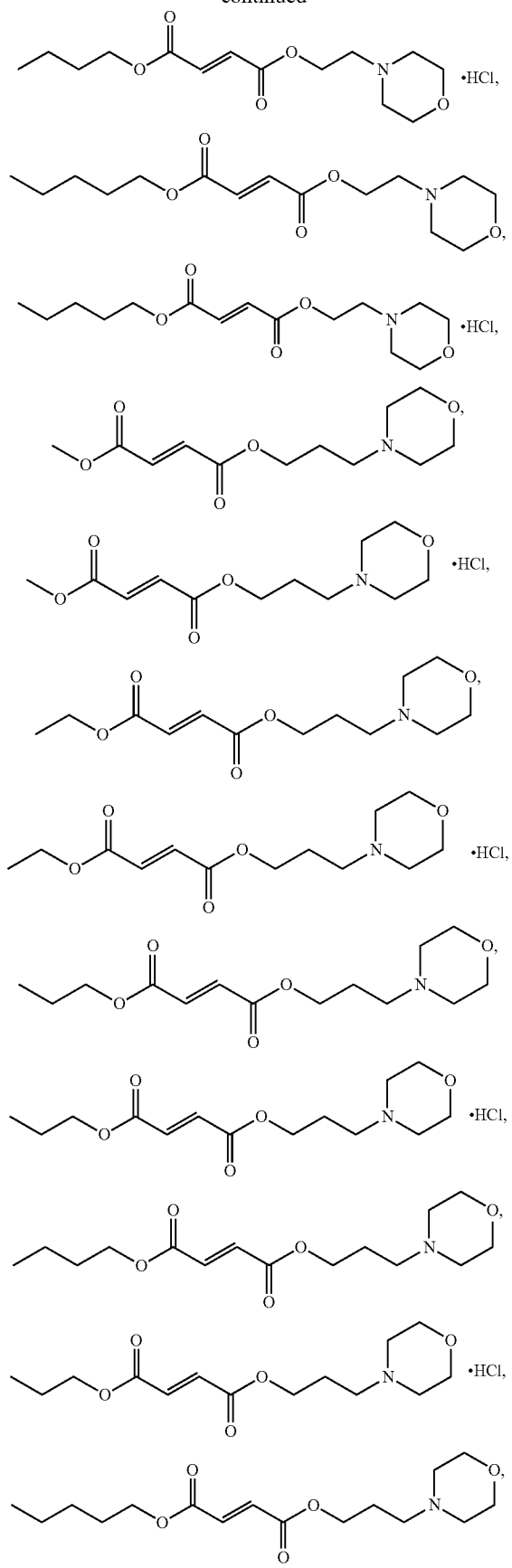
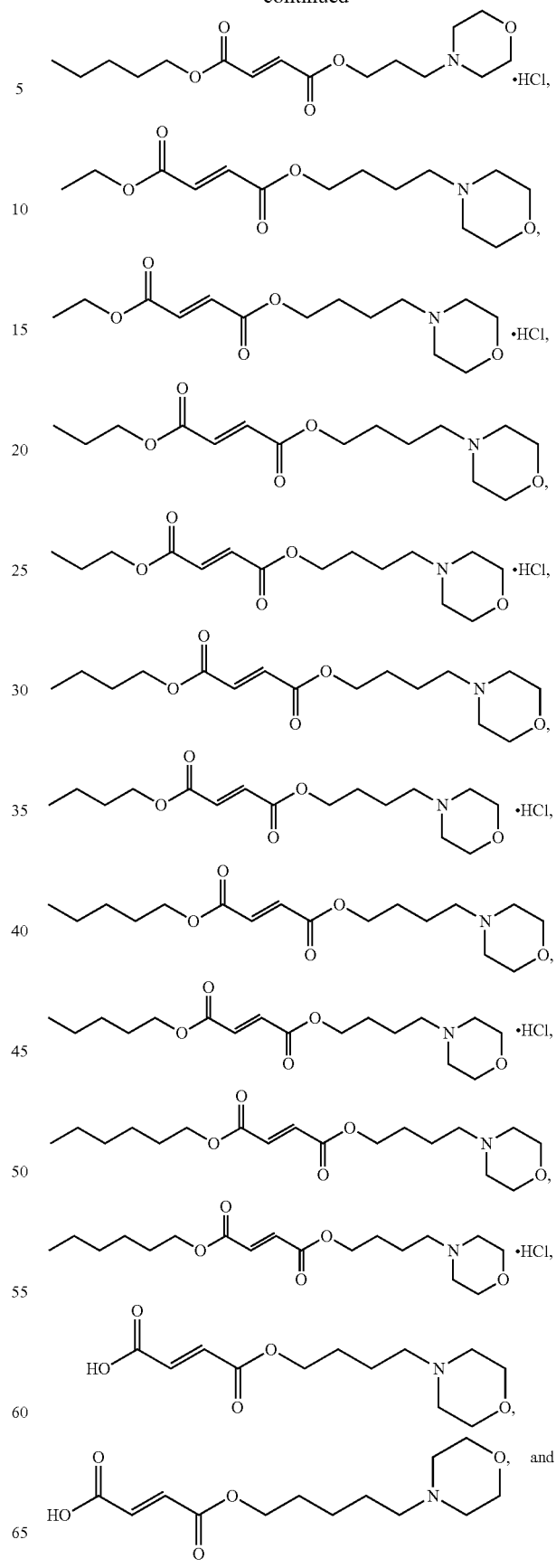

-continued

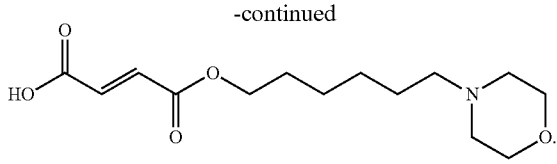

15. A pharmaceutical composition comprising a pharmaceutically acceptable vehicle and a therapeutically effective amount of a compound of Formula (IIIc):

(IIIc)

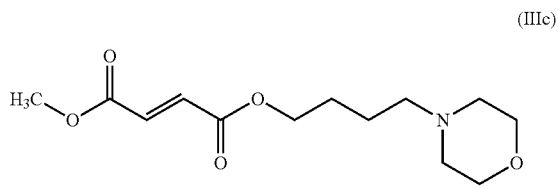 [SMILES: COC(=O)/C=C/C(=O)OCCCCN1CCOCC1]

or a pharmaceutically acceptable salt thereof.

16. The pharmaceutical composition according to claim 15, wherein the compound is a HCl salt.

17. The pharmaceutical composition according to claim 9, wherein the composition is suitable for oral administration.

18. The pharmaceutical composition according to claim 9, wherein the compound is present in an amount that is effective for the treatment of a disease chosen from multiple sclerosis, psoriasis, irritable bowel disorder, ulcerative colitis, arthritis, chronic obstructive pulmonary disease, asthma, Parkinson's disease, Huntington's disease, and amyotrophic lateral sclerosis.

19. A method for treating in a mammal in need thereof a disease or condition which comprises administering to the mammal an effective disease-treating or condition-treating amount of a compound according to Formula (I):

(I)

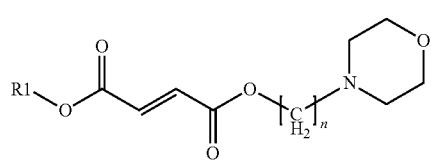

or a pharmaceutically acceptable salt thereof;
wherein:
n is an integer from 2 to 6; and
$R^1$ is selected from H, methyl, ethyl, and $C_{3-6}$ alkyl, and wherein the disease or condition is chosen from psoriasis, psoriasis vulgaris, guttate psoriasis, hyperkeratosis, arthritis, inflammatory arthritis, rheumatoid arthritis, juvenile rheumatoid arthritis, juvenile idiopathic arthritis, psoriatic arthritis, ankylosing spondylitis, inflammatory bowel disease (IBD), irritable bowel disorder, Crohn's disease, ulcerative colitis, collagenous colitis, lymphocytic colitis, ischemic colitis, diversion colitis, Bechet's colitis, indeterminate colitis, asthma, chronic obstructive pulmonary disease (COPD), chronic bronchitis, emphysema, asbestosis, pneumoconiosis, pulmonary neoplasms, multiple sclerosis, Parkinson's disease, Alzheimer's disease, Huntington's disease, amyotrophic lateral sclerosis, retinopathia pigmentosa, mitochondrial encephalomyopathy, cardiac insufficiency, left ventricular insufficiency, myocardial infarction, angina pectoris, ischemia and reperfusion injury, transplantation rejection, AGE-induced genome damage, NF-κB mediated diseases, rheumatic, eczema, sarcoidosis, granuloma annulare, autoimmune carditis, acute disseminated encephalomyelitis, Addison's disease, alopecia greata, ankylosing spondylitis, antiphospholipid antibody syndrome, autoimmune hemolytic anemia, autoimmune hepatitis, autoimmune inner ear disease, bullous pemphigoid, Bechet's disease, celiac disease, Chagas disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, myasthenia gravis, narcolepsy, neuromyotonia, pemphigus vulgaris, pernicious anemia, polymyositis, primary biliary cirrhosis, schizophrenia, scleroderma, Sjogren's syndrome, stiff person syndrome, temporal arteritis, ulcerative colitis, vasculitis, vitiligo, myasthenia gravis, or Wegener's granulomatosis.

20. The method according to claim 19, wherein $R^1$ is methyl.

21. The method according to claim 19, wherein $R^1$ is methyl, ethyl, n-propyl, isopropyl, n-butyl, isobutyl, tert-butyl, n-pentyl, pentyl-2-yl, 2-methylbutyl, isopentyl, 3-methylbutan-2-yl, neopentyl, tert-pentyl, n-hexyl, hexan-2-yl, 2-methylpentyl, 3-methylpentyl, 4-methylpentyl, 3-methylpentan-2-yl, 4-methylpentan-2-yl, 2,3-dimethylbutyl or 3,3-dimethylbutyl.

22. The method according to claim 19, wherein the compound is a pharmaceutically acceptable salt.

23. The method according to claim 19, wherein the compound is a HCl salt.

24. A method for treating in a mammal in need thereof a disease or condition which comprises administering to the mammal an effective disease-treating or condition-treating amount of a compound according to Formula (IIIc):

(IIIc)

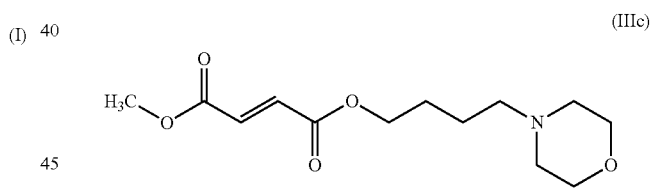

or a pharmaceutically acceptable salt thereof,
wherein the disease or condition is chosen from psoriasis, psoriasis vulgaris, guttate psoriasis, hyperkeratosis, arthritis, inflammatory arthritis, rheumatoid arthritis, juvenile rheumatoid arthritis, juvenile idiopathic arthritis, psoriatic arthritis, ankylosing spondylitis, inflammatory bowel disease (IBD), irritable bowel disorder, Crohn's disease, ulcerative colitis, collagenous colitis, lymphocytic colitis, ischemic colitis, diversion colitis, Bechet's colitis, indeterminate colitis, asthma, chronic obstructive pulmonary disease (COPD), chronic bronchitis, emphysema, asbestosis, pneumoconiosis, pulmonary neoplasms, multiple sclerosis, Parkinson's disease, Alzheimer's disease, Huntington's disease, amyotrophic lateral sclerosis, retinopathia pigmentosa, mitochondrial encephalomyopathy, cardiac insufficiency, left ventricular insufficiency, myocardial infarction, angina pectoris, ischemia and reperfusion injury, transplantation rejection, AGE-induced genome damage, NF-κB mediated diseases, rheumatic, eczema, sarcoidosis, granuloma annulare, autoimmune carditis, acute disseminated encephalomyelitis, Addison's disease, alopecia greata, ankylosing spondylitis, antiphospholipid antibody syndrome, autoimmune hemolytic anemia, autoimmune hepatitis, autoimmune inner ear disease, bullous pemphigoid, Bechet's disease, celiac disease, Chagas disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, myasthenia gravis, narcolepsy, neuromyotonia, pemphigus vulgaris, pernicious anemia, polymyositis, primary biliary cirrhosis, schizophrenia, scleroderma, Sjogren's syndrome, stiff person syndrome, temporal arteritis, ulcerative colitis, vasculitis, vitiligo, myasthenia gravis, or Wegener's granulomatosis.

25. The method according to claim 24, wherein the compound is a HCl salt.

26. The method according to claim 24, wherein the disease or condition is chosen from multiple sclerosis, psoriasis, irritable bowel disorder, ulcerative colitis, arthritis, chronic obstructive pulmonary disease, asthma, Parkinson's disease, Huntington's disease, or amyotrophic lateral sclerosis.

27. The method according to claim 19, wherein the disease or condition is chosen from psoriasis, psoriasis vulgaris, guttate psoriasis, hyperkeratosis, arthritis, inflammatory arthritis, rheumatoid arthritis, juvenile rheumatoid arthritis, juvenile idiopathic arthritis, psoriatic arthritis, ankylosing spondylitis, multiple sclerosis, inflammatory bowel disease (IBD), irritable bowel syndrome, Crohn's Disease, Ulcerative Colitis, collagenous colitis, lymphocytic colitis, ischemic colitis, diversion colitis, Bechet's colitis, indeterminate colitis, asthma, chronic obstructive pulmonary disease (COPD), chronic bronchitis, emphysema, asbestosis, pneumoconiosis, pulmonary neoplasms, multiple sclerosis, Parkinson's disease, Alzheimer's disease, Huntington's disease, or amyotrophic lateral sclerosis.

28. The method according to claim 24, wherein the disease or condition is chosen from psoriasis, psoriasis vulgaris, guttate psoriasis, hyperkeratosis, arthritis, inflammatory arthritis, rheumatoid arthritis, juvenile rheumatoid arthritis, juvenile idiopathic arthritis, psoriatic arthritis, ankylosing spondylitis, multiple sclerosis, inflammatory bowel disease (IBD), irritable bowel syndrome, Crohn's Disease, Ulcerative Colitis, collagenous colitis, lymphocytic colitis, ischemic colitis, diversion colitis, Bechet's colitis, indeterminate colitis, asthma, chronic obstructive pulmonary disease (COPD), chronic bronchitis, emphysema, asbestosis, pneumoconiosis, pulmonary neoplasms, multiple sclerosis, Parkinson's disease, Alzheimer's disease, Huntington's disease, or amyotrophic lateral sclerosis.

29. The method according to claim 19, wherein the disease or condition is chosen from multiple sclerosis, psoriasis, irritable bowel disorder, ulcerative colitis, arthritis, chronic obstructive pulmonary disease, asthma, Parkinson's disease, Huntington's disease, or amyotrophic lateral sclerosis.

* * * * *

UNITED STATES PATENT AND TRADEMARK OFFICE
CERTIFICATE OF CORRECTION

PATENT NO. : 8,952,006 B2
APPLICATION NO. : 13/761864
DATED : February 10, 2015
INVENTOR(S) : Cundy et al.

It is certified that error appears in the above-identified patent and that said Letters Patent is hereby corrected as shown below:

In the claims,

(Claim 6) Column 83, line 36, delete the "-" before "group";
(Claim 6) Column 84, line 23, delete "Cl⁻";
(Claim 9) Column 87, line 31, replace "H methyl" with --H, methyl--.

Signed and Sealed this
Twenty-second Day of September, 2015

Michelle K. Lee
*Director of the United States Patent and Trademark Office*